United States Patent
Cai et al.

(10) Patent No.: US 6,579,896 B2
(45) Date of Patent: Jun. 17, 2003

(54) METHOD FOR TREATING ALLERGIES USING SUBSTITUTED PYRAZOLES

(75) Inventors: Hui Cai, San Diego, CA (US); James P. Edwards, San Diego, CA (US); Yin Gu, San Diego, CA (US); Lars Karlsson, La Jolla, CA (US); Steven P. Meduna, San Diego, CA (US); Barbara A. Pio, San Diego, CA (US); Siquan Sun, San Diego, CA (US); Robin L. Thurmond, San Diego, CA (US); Jianmei Wei, San Diego, CA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/946,713

(22) Filed: Sep. 5, 2001

(65) Prior Publication Data

US 2002/0147189 A1 Oct. 10, 2002

Related U.S. Application Data

(60) Provisional application No. 60/230,407, filed on Sep. 6, 2000.

(51) Int. Cl.$^7$ .................... A61K 31/415; A61K 31/445; A61K 31/38; A61K 31/36
(52) U.S. Cl. ..................... 514/406; 514/315; 514/415; 514/438; 514/444; 514/461; 514/464
(58) Field of Search .................. 514/406, 315, 514/415, 438, 444, 461, 464

(56) References Cited

U.S. PATENT DOCUMENTS

| | | | |
|---|---|---|---|
| 4,500,525 A | 2/1985 | Winters et al. | |
| 5,264,576 A | 11/1993 | Shutske et al. | |
| 5,776,718 A | 7/1998 | Palmer et al. | |
| 5,976,858 A | 11/1999 | Palmer et al. | |
| 6,030,946 A | 2/2000 | Klaus et al. | |
| 6,214,813 B1 * | 4/2001 | Zhang et al. | 514/150 |
| 6,287,840 B1 | 9/2001 | Palmer et al. | |

FOREIGN PATENT DOCUMENTS

| | | | |
|---|---|---|---|
| EP | 0254241 A | | 1/1988 |
| EP | 382637 B1 | | 7/1993 |
| EP | 502786 B1 | | 4/1996 |
| EP | 747049 | * | 12/1996 |
| EP | 655248 B1 | | 9/1999 |
| WO | WO 95/23222 A1 | | 8/1995 |
| WO | WO 96/30353 A1 | | 10/1996 |
| WO | WO 97/21439 A1 | | 6/1997 |
| WO | WO 97/40066 A1 | | 10/1997 |
| WO | WO 9856785 A | | 12/1998 |
| WO | WO 99/48911 A | | 3/1999 |
| WO | WO 99/24460 A2 | | 5/1999 |
| WO | WO 99/58153 A1 | | 11/1999 |
| WO | WO 00/49008 A | | 8/2000 |
| WO | WO 00/51998 A | | 9/2000 |
| WO | WO 00/55144 A | | 9/2000 |
| WO | WO 01/09110 A | | 2/2001 |
| WO | WO 01/19796 A | | 3/2001 |
| WO | WO 01/40204 A | | 6/2001 |

OTHER PUBLICATIONS

Nakatsuka, Masashi Et Al.; "Preparation of pyrazole derivatives as immunosuppressants"; retreived from STN Database accession No. 130:52417, XP002193692 abstract; Chemical Abstracts Service, Columbus, Ohio, US.

PCT International Search Report PCT/US01/27480 dated Apr. 5, 2002.

PCT Search Report for PCT/US 01/27441 dated Jul. 18, 2002.

Allen, E.M. et al; "Reversible Cathepsin S (CATS) Inhibitors Block Invariant Chain Degradation Both In Vitro and In Vivo" Inflammation Research (2001) Sup 3, vol. 50, p S159 abstr. 10/04.

Bromme, D. et al.; "Peptidyl vinyl sulphones: a new class of potent and selective cysteine protease inhibitors"; Biochem. J. (1996) 315:85–89.

Chapman, H.A. et al.; "Emerging Roles For Cysteine Proteases in Human Biology"; Annu. Rev. Physiol. (1997) 59:63–88.

Chapman, H.A. "Endosomal Proteolysis and MHC Class II Function"; Curr. Opin. Immunol. (1998) 10:93–102.

Honey, K. et al.; "Role of Lysosomal Cysteine Proteinases in Antigen Presentation to CD4 T Cells"; Inflammation Research (2001) Sup. 3, vol. 50, pS159 abstr. 10/01.

Li, W. et al.; "Tissue Specific Expression of Cathepsins and Antigen Presentation"; Inflammation Research (2001) Sup 3, vol. 50 p S159 abstr. 10/02.

Magill, C. et al.; "Cysteine Proteases in Antigen Presentation and Models of Inflammation"; Inflammation Research (2001) Sup 3, vol. 50, S159, abstr. 10/03.

Maurer, D. et al.; "Fcɛ Receptor I on Dendritic Cells Delivers IgE–Bound Multivalent Antigens into a Cathepsin S–Dependent Pathway of MHC Class II Presentation" J. Immunol. (1998) 161:2731–2739.

McGrath, M.E. et al.; "Crystal structure of human cathepsin S"; Protein Science (1998) 7:1294–1302.

Nakagawa, T. Y. et al.; "Impaired Invariant Chain Degradation and Antigen Presentation and Diminished Collagen–Induced Arthritis in Cathespin S Null Mice"; Immunity (1999) 10:207–217.

Nakayama, T.Y. et al.: "The role of lysosomal proteinases in MHC class II–mediated antigen processing and presentation" Immunological Rev. (1999) 172:121–129.

Nerenberg, J. B. et al.; "Design and Synthesis of N–Alkylated Saccharins as Selective a–1A Adrenergic Receptor Antagonists"; Bioorg. Med. Chem. Lett. (1998) 8:2467–2472.

Palmer, J. T. et al.; "Vinyl Sulfones as Mechanism–Based Cysteine Protease Inhibitors"; J. Med. Chem. (1995) 38(17):3193–3196.

(List continued on next page.)

Primary Examiner—Kevin E. Weddington

(57) ABSTRACT

A method for the treatment of an allergic condition, including an an atopic allergic conditions, using substituted pyrazoles.

9 Claims, 2 Drawing Sheets

OTHER PUBLICATIONS

Podolin, P.L. et al.; "Inhibition of Cathespin S Blocks Invariant Chain Processing and Antigen–Induced Proliferation In Vitro and Reduces the Severity of Collagen–Induced, Arthritis In Vivo"; Inflammation Research (2001) Sup 3, vol. 50, p S 159 abstr. 10/05.

Riese, R. J. et al.; "Cathespin S Activity Regulates Antigen Presentation and Immunity"; J. Clin. Invest. (1998) 101 (11):2351–2363.

Riese, R.J. et al.; "Cathespins and Compartmentalization in Antigen Presentation"; Curr. Opin. Immunol. (2000) 12:107–113.

Shi, Guo–Ping, et al.; "Cathespin S Required for Normal MHC Class II Peptide Loading and Germinal Center Development"; Immunity (1999) 10:197–206.

Spero, D. et al.; "Design and Synthesis of Novel Cathespin S Inhibitors"; Inflammation Research (2001) Sup. 3, vol. 50, p S206, abstr. 079.

Villadangos, J. A. et al.; "Degradation of Mouse Invariant Chain: Roles of Cathespins S and D and the Influence of Major Histocompatibility Complex Polymorphism" J. Exp. Med. (1997) 186(4):549–560.

Villadangos, J. A. et al.; "Proteases Involved in MHC Class II Antigen Presentation" Immunological Rev. (1999)172:109–120.

Villadangos, J.A. et al.; "Proteolysis in MHC Class II Antigen Presentation: Who's in Charge?"; Immunity (2000) 12:233–239.

Andromati, S.A. et al.; "Synthesis of 1–[4–(4–phenyl–1–piperazinyl)butyl]1,2–dihydro–3H–1,4–benzodiazepin–2–ones and 1H–indazoles and their affinity for benzodiazepine receptors"; Chemical Abstracts No. (CAN) 122:314528; (1994) 8:126–131.

Bromme, D, et al.; "High level expression and crystallization of recombinant human cathespin S"; Protein Science (1996) 5:789–791.

Eberlein–Konig, et al.; "Immunohistochemical investigation of the cellular infiltrates at the sites of allergoid–induced late–phase cutaneous reactions associated with pollen allergen–specific immunotherapy".

Gaga, et al; "Eosinophil Activation and T Lymphoctye Inflitration in Allergin–Induced Late Phase Skin Reactions and Classical Delayed–Type Hypersensitivity" J. Immunol. (1991) 147:816–822.

Kirschke, H. et al.; "Cathespin S"; Handbook of Proteolytic Enzymes; Barrett, A.J.; Rawlings, N.D.; Woessner, J.F., Editors, Academic Press (1998) 621–624.

Riese, R.J. et al.; "Essential Role for Cathespin S in MHC Class II–Associated Invariant Chain Processing and Peptide Loading"; Immunity (1996) 4:357–366.

Singh, P., et al.; "Quantitative Structure–Activity Relationship Studies on a New Class of Antihypertensive Agents: Derivatives of 3–Aryl–4,5,6,7–tetrahydro–1H–pyrazolo[4,3–c]pyridine"; Quant. Struct.–Act. Relat. (1990) 9:29–32.

Winters, G. et al.; "Synthesis in Vitro [3H]Prazosin Displacement and in Vivo Activity of 3–Aryl–4,5,6,7–tetrahydropyrazolo[4,3–c]pyridines, a New Class of Antihypertensive"; J. Med. Chem. (1985)28(7):934–940.

* cited by examiner

1A.

1B.

2A.

2B.

METHOD FOR TREATING ALLERGIES USING SUBSTITUTED PYRAZOLES

CROSS REFERENCE TO RELATED APPLICATIONS

This application claims the benefit of U.S. Provisional Application No. 60/230,407 filed Sep. 6, 2000.

FIELD OF THE INVENTION

This invention relates to the treatment of an allergic condition using substituted pyrazoles.

BACKGROUND OF THE INVENTION

Atopic allergies afflict at least 20% of populations in developed countries and comprise a wide range of IgE-mediated diseases such as hay fever, asthma, atopic dermatitis, and food allergies. Exposure of an allergic subject to relevant allergens cross-links allergen specific IgE bound to mast cells, triggering degranulation and release of proinflammatory mediators, such as histamine and eicosanoids, which cause the weal-and-flare response on a skin test. Characteristically, this early response is followed by a prolonged late reaction in which inflammatory cells, particularly eosinophils and activated TH-2 CD4 T cells, are recruited to the site of allergen exposure. Inflammatory cytokines such as IL-4 and IL-5, both produced by TH-2 cells, are important for IgE production by B cells and for eosinophilia, respectively. Immunotherapies targeting CD4 T cells have been shown to be effective in reducing the production of IgE, the activation of proinflammatory cells, and the release of inflammatory mediators.

Current allergy therapies targeting CD4 T cells have met with mixed success. Desensitization with allergen extracts or vaccines is effective for many allergens, such as the Hymenoptera insect sting which can induce life-threatening allergic reactions. The mechanism may be either induction of T cell tolerance or the conversion of TH-2 to TH-1. However, such treatment requires a long-term treatment regime, frequent doctor visits and prior stabilization by other medications, and is associated with a certain morbidity rate and rare deaths. Alternatively, immunosuppressive drugs such as steroids which effectively stabilize ongoing allergy responses, are often associated with severe side effects.

The activation of CD4 T cells is a major factor in the initiation and maintenance of the allergic response. Allergens are taken up by specialized antigen presenting cells (APCs) such as dendritic cells and B cells. Protein allergens pass through the endosomal or lysosomal system where they are degraded by different proteases. These peptide fragments are bound by the MHC class II molecules which, at the cell surface, are heterotrimeric complexes consisting of two transmembrane glycoprotein chains (α and β) that form a binding scaffold for the third component, a peptide of 11–20 amino acids. The antigen-MHC class II molecule complex is recognized by CD4 T cells and leads to the activation of the T cell. Activated T cells in turn activate several other components of the immune system, such as B cells and macrophages, that are crucial for the body's response to pathogens, but also lead to the symptoms of allergies.

Class II molecules, like other transmembrane proteins, are translocated into the endoplasmic reticulum (ER) after synthesis, where they associate with a third protein, the invariant chain (Ii). The invariant chain molecule is a type II transmembrane protein that serves as a class II-specific chaperone, promoting the exit of class II-Ii complexes from the ER and preventing class II molecules from binding to peptides and unfolded proteins in the ER and in the secretory pathway. A targeting motif in the cytoplasmic tail of Ii directs the class II-Ii complexes from the secretory pathway into the endosomal system.

Before the MHC class II molecules can present antigen the Ii must be removed by a series of proteases that break down Ii. The resultant Ii peptide fragments, called class II-associated invariant chain peptides (CLIP), occupy the peptide binding groove of the class II molecule, and in most cases are not spontaneously released. The CLIP protects the class II binding pocket from collapsing both during intracellular transport and after Ii degradation in the endosomal system. Binding of antigenic peptides generated from endocytosed proteins requires an empty, and yet open binding site. The CLIP therefore must be released while the open binding site is stabilized to allow the binding of other peptides. Human Leukocyte Antigen-DM ('HLA-DM') mediates both of these functions, thus promoting the binding of antigenic peptides. After acquiring peptides, the class II molecules are transported to the cell surface via routes that are largely unknown.

In view of the above, inhibition of invariant chain proteolysis will prevent removal of Ii from the class II binding pocket, which in turn will specifically block antigen binding to the MHC class II molecule.

Cathepsin S ('CatS') is a cysteine protease expressed in lymphatic tissues. CatS mediates invariant chain proteolysis, which is a prerequisite for peptide loading of MHC class II molecules (Riese et al. (1996) Immunity 4:357). CatS has 50–60% homology with cathepsins L and K, but differs from them in that it has a broad pH optimum that extends to alkaline pH. CatS modulates antigen presentation in animal models, and inhibitors are effective in an asthma model (Riese et al. (1998) J. Clin. Invest. 101:2351). Mice deficient in cathepsin S have an impaired ability to present exogenous proteins by professional antigen presenting cells (Nakagawa et al. (1999) Immunity 10:207; Shi et al. (1999) Immunity 10:197).

Compounds that inhibit the proteolytic activity of human cathepsin S are expected to find utility in the treatment of chronic autoimmune diseases including, but not limited to, lupus and rheumatoid arthritis; and have potential utility in modulating the immune response to tissue transplantation. Methods of modulating autoimmunity with an agent that modulates cathepsin S activity, e.g., proteolysis of the Ii chain, as well as methods of treating a subject having an autoimmune disorder, methods of evaluating a treatment for its ability to modulate an immune response are described in WO 99/58153.

Compounds somewhat similar to those of the present invention are described in the following references.

Winters, et. al. (Winters, G.; Sala, A.; Barone, D.; Baldoli, E. J. Med. Chem. 1985, 28, 934–940; Singh, P.; Sharma, R. C. Quant. Struct-Act. Relat. 1990, 9, 29–32; Winters, G.; Sala, A.; Barone, D. in U.S. Pat. No. 4,500,525 (1985)) have described bicyclic pyrazoles of the type shown below. R never contains a heterocyclic ring and no protease inhibitor activity is ascribed to these molecules; they are described as α1-adrenergic receptor modulators.

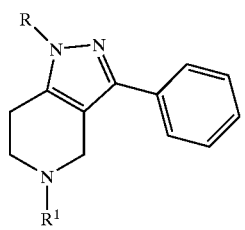

Shutske, et. al. claim the bicylic pyrazoles below. The pyridine ring is aromatic in their system (Shutske, G. M.;

Kapples, K. J.; Tomer, J. D. U.S. Pat. No. 5,264,576 (1993)). Although reference is made to R being a linker to a heterocycle, the claims specify only R=hydrogen. The compounds are referred to as serotonin reuptake inhibitors.

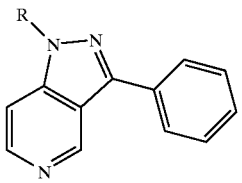

The compound 2-[4-[4-(3-methyl-5-phenyl-1H-pyrazol-1-yl)butyl]-1-piperazinyl]-pyrimidine is known from EP-382637, which describes pyrimidines having anxiolytic properties. This compound and analogs are further described in EP-502786 as cardiovascular and central nervous system agents. Pharmaceutical formulations with such compounds are disclosed in EP-655248 for use in the treatment of gastric secreation and anti-ulcer agents. WO-9721439 describes medicaments with such compounds for treating obsessive-compulsive disorders, sleep apnea, sexual dysfunctions, emesis and motion sickness.

The compounds 5-methyl-3-phenyl-1-[4-(4-phenyl-1-piperazinyl)butyl]-1H-indazole and 5-bromo-3-(2-chlorophenyl)-1-[4-(4-phenyl-1-piperazinyl)butyl]-1H-indazole, in particular the hydrochloride salts thereof, are known from WO-9853940 and CA 122:314528, where these and similar compounds are described as kinase inhibitors in the former reference and possessing affinity for benzodiazepine receptors in the latter reference.

SUMMARY OF THE INVENTION

The present invention features the use of cathepsin S inhibitors to treat allergic conditions, including but not limited to atopic allergies. Examples of an allergic condition include hay fever, asthma, atopic dermatitis and food allergies. Allergens include dust, pollen, mold, and pet dander or pet hair.

In one aspect, the invention provides a method for treating a subject suffering from an allergic condition, in particular an atopic allergic condition, said method comprising administering to said subject a therapeutically effective amount of a pharmaceutical composition comprising a cathepsin S inhibitor.

In another aspect, the invention provides a method for treating a subject suffering from an IgE-mediated allergic condition, in particular an atopic allergic condition, said method comprising administering to said subject a therapeutically effective amount of a pharmaceutical composition comprising a cathepsin S inhibitor.

A third aspect of the invention provides the use, or the use for the manufacture of a medicament, of a cathepsin S inhibitor for treating an allergic condition, more in particular for treating IgE-mediated allergic conditions, still more in particular treating hay fever, asthma, atopic dermatitis or food allergies. The invention also features anti-allergic pharmaceutical compositions comprising as active ingredient an effective amount of a cathepsin S inhibitor, and a pharmaceutically acceptable carrier. The active ingredient can be formulated in any manner suitable for the particular allergic condition, including aerosol, oral and topical formulations and time-release formulations.

The present invention concerns the treatment of an allergic condition with one or more compounds which can be represented by formula (I):

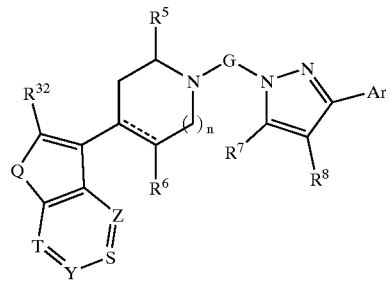

wherein:
the dashed line adjacent C—$R^6$ is absent or an $sp^2$ bond;
Y is nitrogen or $R^{20}C$;
Z is nitrogen or $R^{21}C$;
T is nitrogen or $R^2C$;
S is nitrogen or $R^3C$;
provided between 0 and 3 of S, T, Y, and Z are nitrogen; and further provided that one of S, T, Y, and Z can be $=N^+$—$O^-$ where the remaining three are not nitrogen;

$R^{20}$ is selected from hydrogen, halogen, $C_{1-5}$ alkoxy, hydroxy, $C_{1-5}$ alkyl, cyano, nitro, $C_{1-5}$ haloalkyl, $R^oR^pN$, $R^oR^pNC=O$, $C_{2-8}$ acyl, 4–7 membered heterocyclyl, (4–7 membered heterocyclyl)-$C_{1-5}$ alkylene, phenyl, (phenyl)$C_{1-5}$ alkylene, $R^{14}OC=O$, $R^{14}S$, $R^{14}SO$, and $R^{14}SO_2$;

$R^{21}$ is selected from hydrogen, halogen, $C_{1-5}$ alkoxy, hydroxy, $C_{1-5}$ alkyl, cyano, nitro, $C_{1-5}$ haloalkyl, $R^cR^dN$, $R^cR^dNC=O$, $C_{2-8}$ acyl, 4–7 membered heterocyclyl, (4–7 membered heterocyclyl)-$C_{1-5}$ alkylene, phenyl, (phenyl)$C_{1-5}$ alkylene, $R^{15}OC=O$, $R^{15}S$, $R^{15}SO$ and $R^{15}SO_2$;

$R^2$ is selected from hydrogen, halogen, $C_{1-5}$ alkoxy, hydroxy, $C_{1-5}$ alkyl, cyano, nitro, $C_{1-5}$ haloalkyl, $R^eR^fN$, $R^eR^fNC=O$, $C_{2-8}$ acyl, 4–7 membered heterocyclyl, (4–7 membered heterocyclyl)-$C_{1-5}$ alkylene, phenyl, (phenyl)$C_{1-5}$ alkylene, $R_{16}OC=O$, $R^{16}S$, $R^{16}SO$ and $R^{16}SO_2$;

$R^3$ is selected from hydrogen, halogen, $C_{1-5}$ alkoxy, hydroxy, $C_{1-5}$ alkyl, cyano, nitro, $C_{1-5}$ haloalkyl, $R^gR^hN$, $C_{2-8}$ acyl, 4–7 membered heterocyclyl, (4–7 membered heterocyclyl)-$C_{1-5}$ alkylene, phenyl, (phenyl)$C_{1-5}$ alkylene, $R^{17}OC=O$, $R'''R''NC=O$, $R'''R''NSO_2$, $R^{17}SO$ and $R^{17}SO_2$;

$R^5$ and $R^6$ are independently selected from hydrogen and $C_{1-5}$ alkyl;

$R^7$ and $R^8$ independently are hydrogen, $C_{1-5}$ alkyl, $C_{1-5}$ alkenyl, $C_{1-5}$ alkoxy, $C_{1-5}$ alkylthio, halogen, or 4–7 membered carbocyclyl or heterocyclyl; alternatively, $R^7$ and $R^8$ can be taken together to form an optionally substituted 5- to 7-membered carbocyclic or heterocyclic ring, which ring may be unsaturated or aromatic; said ring being optionally substituted with between 1 and 3 substituents independently selected from halo, hydroxy, cyano, nitro, amino, $R^1$, $R'O$—, $R'S$—, $R'O$ ($C_{1-5}$ alkylene)-, $R'O(C=O)$—, $R'(C=O)$—, $R'(C=S)$—, $R'(C=O)O$—, $R'O(C=O)(C=O)$—, $R'SO_2$, $NHR''(C=NH)$—, $NHR''SO_2$-, and $NHR''$ ($C=O$)—;

$R'$ is $C_{1-6}$ alkyl, phenyl, benzyl, phenethyl, or $C_{2-5}$ heterocyclyl, ($C_{1-5}$ heterocyclyl)$C_{1-6}$ alkylene, $NH_2$, mono- or di($C_{1-6}$ alkyl)N—, or $R^{49}OR^{50}$—, wherein $R^{49}$ is H, $C_{1-5}$ alkyl, $C_{2-5}$ alkenyl, phenyl, benzyl, phenethyl, $C_{1-5}$ heterocyclyl, or ($C_{1-5}$ heterocyclyl)$C_{1-6}$ alkylene and $R^{50}$ is $C_{1-5}$ alkylene, phenylene, or divalent $C_{1-5}$ heterocyclyl; and $R^u$ can be H in addition to the values for $R^t$;

$R^c$ is hydrogen, $C_{1-5}$ alkyl, phenyl, $C_{2-5}$ heterocyclyl, $C_{2-8}$ acyl, aroyl, $R^{10}OC=O$—, $R^iR^jNC=O$, $R^{10}SO$—, $R^{10}SO_2$-; and $R^iR^jNSO_2$;

$R^e$ is hydrogen, $C_{1-5}$ alkyl, phenyl, $C_{2-5}$ heterocyclyl, $C_{2-8}$ acyl, aroyl, $R^{40}OC=O$, $R^{43}R^{44}NC=O$, $R^{40}SO$, $R^{40}SO_2$, and $R^{43}R^{44}NSO_2$-;

$R^m$ is hydrogen, $C_{1-5}$ alkyl, phenyl, $C_{2-5}$ heterocyclyl, $C_{2-8}$ acyl, aroyl, $R^{41}OC=O$, $R^{45}R^{46}NC=O$, $R^{41}SO_2$, $R^{45}R^{46}NSO_2$;

$R^o$ is hydrogen, $C_{1-5}$ alkyl, phenyl, $C_{2-5}$ heterocyclyl, $C_{2-8}$ acyl, aroyl, $R^{42}OC=O$, $R^{47}R^{46}NC=O$, $R^{42}SO$, $R^{42}SO_2$, and $R^{47}R_{48}NSO_2$;

each of $R^d$, $R^f$, $R^n$, and $R^p$ is independently selected from hydrogen, $C_{1-5}$ alkyl, phenyl, and $C_{2-5}$ heterocyclyl; in addition, $R^c$ and $R^d$, $R^e$ and $R^f$, $R^m$ and $R^n$, or $R^o$ and $R^p$, independently, can be taken together to form an optionally substituted 4- to 7-membered heterocyclic ring, which ring may be saturated, unsaturated or aromatic;

each of $R^9$, $R^{10}$, $R^{11}$, $R^{14}$, $R^{15}$, $R^{16}$, $R^{17}$, $R^{40}$, $R^{41}$, and $R^{42}$ is independently $C_{1-5}$ alkyl, phenyl, or $C_{2-5}$ heterocyclyl;

each of $R^i$ and $R^j$, $R^k$ and $R^l$, $R^{43}$ and $R^{44}$, $R^{45}$ and $R^{46}$, $R^{47}$ and $R^{48}$ are independently hydrogen, $C_{1-5}$ alkyl, $C_{3-5}$ alkenyl, phenyl, or $C_{2-5}$ heterocyclyl; in addition, $R^i$ and $R^j$, and $R^k$ and $R^l$, $R^{43}$ and $R^{44}$, $R^{45}$ and $R^{46}$, and $R^{47}$ and $R^{48}$, independently, can be taken together to form an optionally substituted 4- to 7-membered heterocyclic ring, which ring may be saturated, unsaturated or aromatic;

$R^g$ is hydrogen, $C_{1-5}$ alkyl, phenyl, or $C_{2-5}$ heterocyclyl, $C_{2-8}$ acyl, aroyl, $R^9OC=O$, $R^{18}R^{19}NC=O$, $R^9SO$, $R^9SO_2$, or $R^{18}R^{19}NSO_2$;

$R^h$ is hydrogen, $C_{1-5}$ alkyl, phenyl, or $C_{2-5}$ heterocyclyl; alternatively, $R^g$ and $R^h$ can be taken together to form an optionally substituted 4- to 7-membered heterocyclic ring, which ring may be saturated, unsaturated or aromatic;

$R^{18}$ and $R^{19}$ independently are hydrogen, $C_{1-5}$ alkyl, phenyl, or $C_{2-5}$ heterocyclyl; alternatively, $R^{18}$ and $R^{19}$ can be taken together to form an optionally substituted 4- to 7-membered heterocyclic ring, which ring may be saturated, unsaturated or aromatic;

n is 0, or 2;

G is $C_{3-6}$ alkenediyl or $C_{3-6}$ alkanediyl, optionally substituted with hydroxy, halogen, $C_{1-5}$ alkyl, $C_{1-5}$ alkoxy, oxo, hydroximino, $CO_2R^k$, $NR^kR^l$, (L)—$C_{1-4}$ alkylene-, $R^kR^lNCO_2$, [(L)—$C_{1-5}$ alkylene]amino, $N_3$, or (L)—$C_{1-5}$ alkoxy;

L is amino, mono- or di-$C_{1-5}$ alkylamino, pyrrolidinyl, morpholinyl, piperidinyl, homopiperidinyl, or piperazinyl, wherein available ring nitrogens can be optionally substituted with $C_{1-5}$ alkyl, benzyl, $C_{2-5}$ acyl, $C_{1-5}$ alkylsulfonyl, or $C_{1-5}$ alkoxycarbonyl;

Ar represents a monocyclic or bicyclic aryl or heteroaryl ring, optionally substituted with between 1 and 3 substituents independently selected from halogen, $C_{1-5}$ alkoxy, $C_{1-5}$ alkyl, $C_{2-5}$ alkenyl, cyano, azido, nitro, $R^{22}R^{23}N$, $R^{22}S$, $R^{22}SO$, $R^{22}SO_2$, $R^{22}OC=O$, $R^{22}R^{23}NC=O$, $C_{1-5}$ haloalkyl, $C_{1-5}$ haloalkoxy, $C_{1-5}$ haloalkylthio, and $C_{1-5}$ alkylthio;

$R^{22}$ is hydrogen, $C_{1-5}$ alkyl, $C_{3-5}$ alkenyl, phenyl, benzyl, $C_{2-5}$ heterocyclyl, $C_{2-8}$ acyl, aroyl, $R^{11}OC=O$, $R^{24}R^{25}NC=O$, $R^{22}S$, $R^{11}SO_2$, or $R^{24}R^{25}NSO_2$;

$R^{23}$ is hydrogen, $C_{1-5}$ alkyl, phenyl, benzyl, or $C_{2-5}$ heterocyclyl; alternatively, $R^{22}$ and $R^{23}$ can be taken together to form an optionally substituted 4- to 7-membered heterocyclic ring, which ring may be saturated, unsaturated or aromatic;

$R^{24}$ and $R^{25}$ are independently hydrogen, $C_{1-5}$ alkyl, phenyl, benzyl, or $C_{1-5}$ heteroaryl; alternatively, $R^{24}$ and $R^{25}$ can be taken together to form an optionally substituted 4- to 7-membered carbocyclic or heterocyclic ring, which ring may be saturated, unsaturated or aromatic;

$R^{32}$ is hydrogen, $C_{1-5}$ alkyl, cyano, $C_{1-5}$ hydroxyalkyl, $C_{2-8}$ acyl, —(C=O)$NR^yR^x$, CHO, or $C_{1-6}$ alkoxycarbonyl, wherein each of $R^y$ and $R^x$ is independently selected from H, $C_{1-5}$ alkyl, $C_{1-5}$ hydroxyalkyl, $C_{1-5}$ heterocyclyl, ($C_{1-5}$ heterocyclyl) $C_{1-5}$ alkylene, $C_{1-5}$ aminoalkylene, $C_{3-8}$ acyloxy, CHO, $C_{1-6}$ alkoxycarbonyl, and cyano;

Q is $NR^{33}$, S, or O;

$R^{33}$ represents hydrogen, $C_{1-5}$ alkyl, phenyl, benzyl, phenethyl, $C_{2-5}$ heterocyclyl, ($C_{2-5}$ heterocyclyl)$C_{1-5}$ alkylene, $C_{2-8}$ acyl, aroyl, $R^{35}OC=O$, $R^{36}R^{37}NC=O$, $R^{35}SO$, $R^{35}S$, $R^{35}SO_2$ and $R^{36}R^{37}NSO_2$;

$R^{35}$ is selected from hydrogen, $C_{1-5}$ alkyl, phenyl, benzyl, phenethyl, and $C_{2-5}$ heteroaryl;

$R^{36}$ and $R^{37}$ are each independently selected from hydrogen, $C_{1-5}$ alkyl, phenyl, or $C_{2-5}$ heteroaryl; alternatively, $R^{36}$ and $R^{37}$ can be taken together to form an optionally substituted 4- to 7-membered ring heterocyclic ring, which ring may be saturated, unsaturated or aromatic;

wherein each of the above hydrocarbyl or heterocarbyl groups, unless otherwise indicated, and in addition to any specified substituents, is optionally and independently substituted with between 1 and 3 substituents selected from methyl, halomethyl, hydroxymethyl, halo, hydroxy, amino, nitro, cyano, $C_{1-5}$ alkyl, $C_{1-5}$ alkoxy, —COOH, $C_{2-6}$ acyl, [di($C_{1-4}$ alkyl)amino]$C_{2-5}$ alkylene, [di($C_{1-4}$ alkyl)amino] $C_{2-5}$ alkyl-NH—CO—, and $C_{1-5}$ haloalkoxy;

or a pharmaceutically acceptable salt, amide, or ester thereof; or a stereoisomeric form thereof.

The disclosed compounds are high-affinity inhibitors of the proteolytic activity of human cathepsin S. For use in medicine, the preparation of pharmaceutically acceptable salts of compounds of formula (I) may be desirable.

Certain compounds of the present invention may have one stereogenic atom and may exist as two enantiomers. Certain compounds of the present invention may have two or more stereogenic atoms and may further exist as diastereomers. It is to be understood by those skilled in the art that all such stereoisomers and mixtures thereof in any proportion are encompassed within the scope of the present invention.

Another aspect of the invention provides pharmaceutical anti-allergic compositions comprising a compound of formula (I) and a pharmaceutically acceptable carrier. A further embodiment of the invention is a process for making an anti-allergic pharmaceutical composition comprising mixing a disclosed compound as described above, with a suitable pharmaceutically acceptable carrier.

The invention also contemplates pharmaceutical compositions comprising more than one compound of formula (I) and compositions comprising a compound of formula (I) and another pharmaceutically active agent.

The invention features a method of treating allergic disorders or conditions mediated by the cathepsin S enzyme, in a subject in need thereof, comprising administering to the subject a therapeutically effective amount of any of the compounds or pharmaceutical compositions described above. If more than one active agent is administered, the therapeutically effective amount may be a jointly effective amount. The compounds described herein inhibit the protease activity of human cathepsin S, an enzyme involved in the immune response. In preferred embodiments, cathepsin S inhibition is selective.

Additional features and advantages of the invention will become apparent from the detailed description below, including examples, and the appended claims.

BRIEF DESCRIPTION OF THE FIGURES

FIG. 1A: Dilution curve for purified PBMC from an allergy donor were cultured with titrated doses of allergen extracts prepared from Derp and Der f for seven days. Proliferation of T cells was scored by measuring $^3$H-thymidine incorporation for 18 h at the end of culture. Bottom panel, FIG. 1B: Effect of titrated doses of LHVS on proliferative responses of T cells to dust mite extracts.

FIG. 2A: Dilution curve for purified PBMC from an allergy donor were cultured with titrated doses of allergen extracts prepared from Ragweed short and Ragweed giant for seven days. Proliferation of T cells was scored by measuring $^3$H-thymidine incorporation for 18 h at the end of culture. Bottom panel, FIG. 2B: Effect of titrated doses of LHVS on proliferative responses of T cells to ragweed extracts.

DETAILED DESCRIPTION OF THE INVENTION

Figure 1:
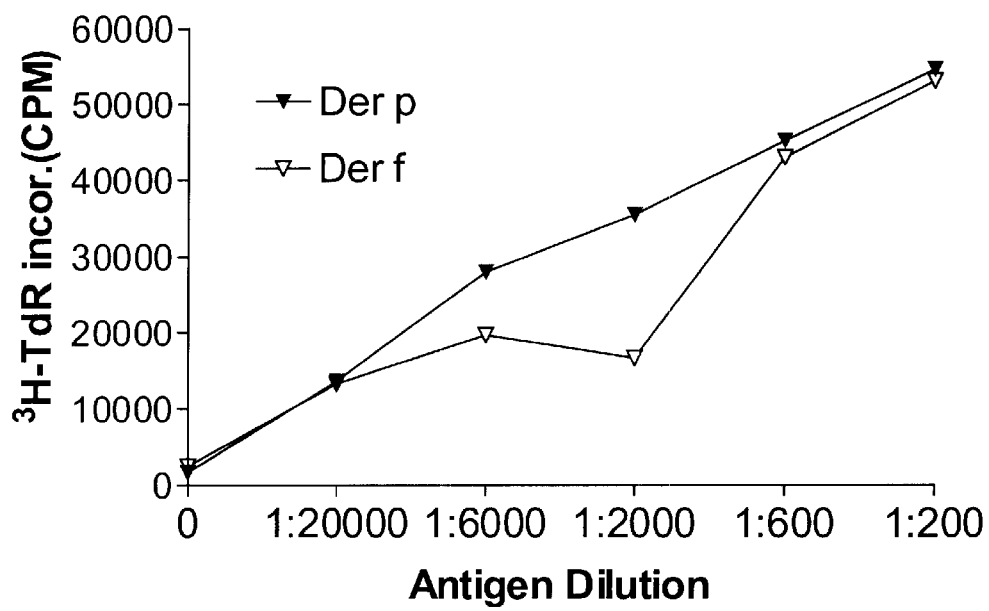
FIG. 1 shows the inhibition of human T cell proliferative responses to two species of dust mites, Der p and Der f. Top panel.
Figure 1:
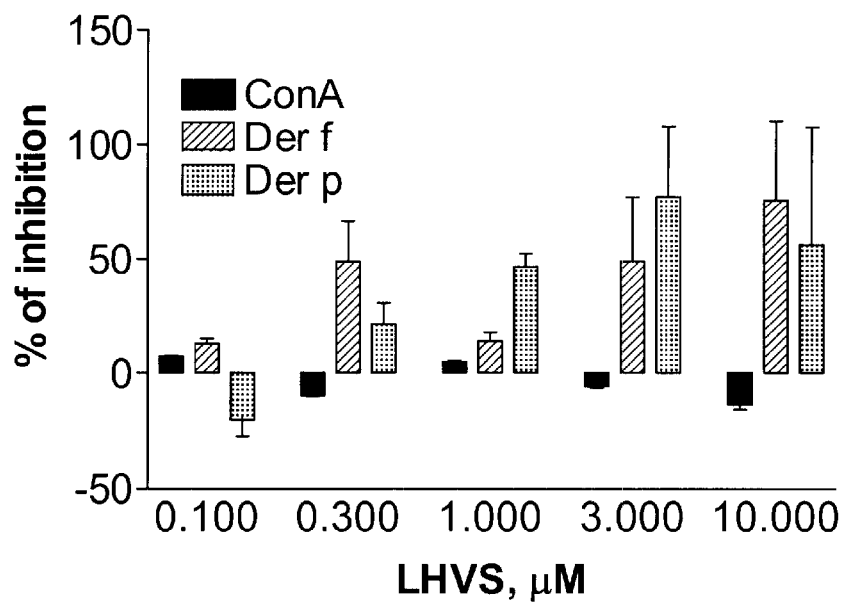

A target of the present invention was to determine whether the presentation of particular antigens in a human system is affected by the inhibition of cathepsin S. According to the invention, it now has been found that inhibitors of cathepsin S block the presentation of several crude allergen extracts in a human ex vivo assay, thereby supporting the use of cathepsin S inhibitors for the treatment of such allergic conditions.

Blocking Ii degradation should decrease antigen presentation to CD4 T cells and disrupt the normal immune response. A cathepsin S inhibitor should specifically affect the activation of CD4 T cells, thus limiting the extent of concomitant immunosuppression, an undesirable side effect of corticosteroid therapy.

By using cathepsin S inhibitors according to the methods of the present invention, the immunological component of the allergic reaction can be blocked to varying degrees, with the advantage over current therapies of being more selective, having fewer or reduced side effects, or both. The present invention is based, in part, on the finding that cathepsin S inhibitors can block the presentation of crude allergen extracts in a human ex vivo assay. This ex vivo system closely mimics the process that occurs in the whole body wherein antigens enter the blood stream,and are presented by antigen presenting cells, which in turn activate CD4 T cells. In the case of treating a subject, the inhibitor or a metabolite thereof would also be present in the blood as in the ex vivo assay.

The invention features the treatment of an allergic condition using one or more pyrazole compounds of formula (I).

A. Terms

The following terms are defined below and by their usage throughout this disclosure.

"Alkyl" includes optionally substituted straight chain and branched hydrocarbons with at least one hydrogen removed to form a radical group. Alkyl groups include methyl, ethyl, propyl, isopropyl, butyl, isobutyl, t-butyl, 1-methylpropyl, pentyl, isopentyl, sec-pentyl, hexyl, heptyl, octyl, and so on. Alkyl includes cycloalkyl, such as cyclopropyl, cyclobutyl, cyclopentyl, and cyclohexyl.

"Alkenyl" includes optionally substituted straight chain and branched hydrocarbon radicals as above with at least one carbon-carbon double bond ($sp^2$). Alkenyls include ethenyl (or vinyl), prop-1-enyl, prop-2-enyl (or allyl), isopropenyl (or 1-methylvinyl), but-1-enyl, but-2-enyl, butadienyls, pentenyls, hexa-2,4-dienyl, and so on. Hydrocarbon radicals having a mixture of double bonds and triple bonds, such as 2-penten-4-ynyl, are grouped as alkynyls herein. Alkenyl includes cycloalkenyl. Cis and trans or (E) and (Z) forms are included within the invention.

"Alkynyl" includes optionally substituted straight chain and branched hydrocarbon radicals as above with at least one carbon-carbon triple bond (sp). Alkynyls include ethynyl, propynyls, butynyls, and pentynyls. Hydrocarbon radicals having a mixture of double bonds and triple bonds, such as 2-penten-4-ynyl, are grouped as alkynyls herein. Alkynyl does not include cycloalkynyl.

"Alkoxy" includes an optionally substituted straight chain or branched alkyl group with a terminal oxygen linking the alkyl group to the rest of the molecule. Alkoxy includes methoxy, ethoxy, propoxy, isopropoxy, butoxy, t-butoxy, pentoxy and so on. "Aminoalkyl", "thioalkyl", and "sulfonylalkyl" are analogous to alkoxy, replacing the terminal oxygen atom of alkoxy with, respectively, NH (or NR), S, and $SO_2$. Heteroalkyl includes alkoxy, aminoalkyl, thioalkyl, and so on.

"Aryl" includes phenyl, naphthyl, biphenylyl, tetrahydronaphthyl, and so on, any of which may be optionally substituted. Aryl also includes arylalkyl groups such as benzyl, phenethyl, and phenylpropyl. Aryl includes a ring system containing an optionally substituted 6-membered carbocyclic aromatic ring, said system may be bicyclic, bridge, and/or fused. The system may include rings that are aromatic, or partially or completely saturated. Examples of ring systems include indenyl, pentalenyl, 1--dihydronaphthyl, indanyl, benzimidazolyl, benzothiophenyl, indoly, benzofuranyl, isoquinolinyl, and so on.

"Heterocyclyl" includes optionally substituted aromatic and nonaromatic rings having carbon atoms and at least one heteroatom (O, S, N) or heteroatom moiety ($SO_2$, CO, CONH, COO) in the ring. Unless otherwise indicated, a heterocyclic radical may have a valence connecting it to the rest of the molecule through a carbon atom, such as 3-furyl or 2-imidazolyl, or through a heteroatom, such as N-piperidyl or 1-pyrazolyl. Preferably a monocyclic heterocyclyl has between 4 and 7 ring atoms, or between 5 and 6 ring atoms; there may be between 1 and 5 heteroatoms or heteroatom moieties in the ring, and preferably between 1 and 3. A heterocyclyl may be saturated, unsaturated, aromatic (e.g., heteroaryl), nonaromatic, or fused.

Heterocyclyl also includes fused, e.g., bicyclic, rings, such as those optionally condensed with an optionally substituted carbocyclic or heterocyclic five- or six-membered aromatic ring. For example, "heteroaryl" includes an optionally substituted six-membered heteroaromatic ring containing 1, 2 or 3 nitrogen atoms condensed with an optionally substituted five- or six-membered carbocyclic or heterocyclic aromatic ring. Said heterocyclic five- or six-membered aromatic ring condensed with the said five- or six-membered aromatic ring may contain 1, 2 or 3 nitrogen atoms where it is a six-membered ring, or 1, 2 or 3 heteroatoms selected from oxygen, nitrogen and sulfur where it is a five-membered ring.

Examples of heterocyclyls include thiazoylyl, furyl, pyranyl, isobenzofuranyl, pyrrolyl, imidazolyl, pyrazolyl, isothiazolyl, isoxazolyl, pyridyl, pyrazinyl, pyrimidinyl, pyridazinyl, indolizinyl, isoindolyl, indolyl, indazolyl, purinyl, quinolyl, furazanyl, pyrrolidinyl, pyrrolinyl, imdazolidinyl, imidazolinyl, pyrazolidinyl, pyrazolinyl, piperidyl, piperazinyl, indolinyl, and morpholinyl. For example, preferred heterocyclyls or heterocyclic radicals include morpholinyl, piperazinyl, pyrrolidinyl, pyridyl, cyclohexylimino, cycloheptylimino, and more preferably, piperidyl.

Examples illustrating heteroaryl are thienyl, furanyl, pyrrolyl, imidazolyl, oxazolyl, thiazolyl, benzothienyl, benzofuranyl, benzimidazolyl, benzoxazolyl, benzothiazolyl.

"Acyl" refers to a carbonyl moiety attached to either a hydrogen atom (i.e., a formyl group) or to an optionally substituted alkyl or alkenyl chain, or heterocyclyl.

"Halo" or "halogen" includes fluoro, chloro, bromo, and iodo, and preferably chloro or bromo as a substituent.

"Alkanediyl" or "alkylene" represents straight or branched chain optionally substituted bivalent alkane radicals such as, for example, methylene, ethylene, propylene, butylene, pentylene or hexylene.

"Alkenediyl" represents, analogous to the above, straight or branched chain optionally substituted bivalent alkene radicals such as, for example, propenylene, butenylene, pentenylene or hexenylene. In such radicals, the carbon atom linking a nitrogen preferably should not be unsaturated.

"Aroyl" refers to a carbonyl moiety attached to an optionally substituted aryl or heteroaryl group, wherein aryl and heteroaryl have the definitions provided above. In particular, benzoyl is phenylcarbonyl.

As defined herein, two radicals, together with the atom(s) to which they are attached may form an optionally substituted 4- to 7-, 5- to 7-, or a 5- to 6-membered ring carbocyclic or heterocyclic ring, which ring may be saturated, unsaturated or aromatic. Said rings may be as defined above in the Summary of the Invention section. Particular examples of such rings are as follows in the next section.

"Pharmaceutically acceptable salts, esters, and amides" include carboxylate salts (e.g., $C_{1-8}$ alkyl, cycloalkyl, aryl, heteroaryl, or non-aromatic heterocyclic) amino acid addition salts, esters, and amides which are within a reasonable benefit/risk ratio, pharmacologically effective and suitable for contact with the tissues of patients without undue toxicity, irritation, or allergic response. Representative salts include hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, and laurylsulfonate. These may include alkali metal and alkali earth cations such as sodium, potassium, calcium, and magnesium, as well as non-toxic ammonium, quaternary ammonium, and amine cations such as tetramethyl ammonium, methylamine, trimethylamine, and ethylamine. See example, S. M. Berge, et al., "Pharmaceutical Salts," J. Pharm. Sci., 1977, 66:1–19 which is incorporated herein by reference. Representative pharmaceutically acceptable amides of the invention include those derived from ammonia, primary $C_{1-6}$ alkyl amines and secondary di ($C_{1-6}$ alkyl) amines. Secondary amines include 5- or 6-membered heterocyclic or heteroaromatic ring moieties containing at least one nitrogen atom and optionally between 1 and 2 additional heteroatoms. Preferred amides are derived from ammonia, $C_{1-3}$ alkyl primary amines, and di ($C_{1-2}$ alkyl)amines. Representative pharmaceutically acceptable esters of the invention include $C_{1-7}$ alkyl, $C_{5-7}$ cycloalkyl, phenyl, and phenyl($C_{1-4}$)alkyl esters. Preferred esters include methyl esters.

"Patient" or "subject" includes mammals such as humans and animals (dogs, cats, horses, rats, rabbits, mice, non-human primates) in need of observation, experiment, treatment or prevention in connection with the relevant disease or condition. Preferably, the patient or subject is a human.

"Composition" includes a product comprising the specified ingredients in the specified amounts as well as any product which results directly or indirectly from combinations of the specified ingredients in the specified amounts.

"Therapeutically effective amount" or "effective amount" means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

Concerning the various radicals in this disclosure and in the claims, three general remarks are made. The first remark concerns valency. As with all hydrocarbon radicals, whether saturated, unsaturated or aromatic, and whether or not cyclic, straight chain, or branched, and also similarly with all heterocyclic radicals, each radical includes substituted radicals of that type and monovalent, bivalent, and multivalent radicals as indicated by the context of the claims. The context will indicate that the substituent is an alkylene or hydrocarbon radical with at least two hydrogen atoms removed (bivalent) or more hydrogen atoms removed (multivalent). An example of a bivalent radical linking two parts of the molecule is G in formula (I) which links two rings.

Second, radicals or structure fragments as defined herein are understood to include substituted radicals or structure fragments. Hydrocarbyls include monovalent radicals containing carbon and hydrogen such as alkyl, alkenyl, alkynyl, cycloalkyl, and cycloalkenyl (whether aromatic or unsaturated), as well as corresponding divalent radicals such as alkylene, alkenylene, phenylene, and so on. Heterocarbyls include monovalent and divalent radicals containing carbon, hydrogen, and at least one heteroatom. Examples of monovalent heterocarbyls include acyl, acyloxy, alkoxyacyl, heterocyclyl, heteroaryl, aroyl, benzoyl, dialkylamino, hydroxyalkyl, and so on. Using "alkyl" as an example, "alkyl" should be understood to include substituted alkyl having one or more substitutions, such as between 1 and 5, 1 and 3, or 2 and 4 substituents. The substituents may be the same (dihydroxy, dimethyl), similar (chlorofluoro), or different (chlorobenzyl- or aminomethyl-substituted). Examples of substituted alkyl include haloalkyl (such as fluoromethyl, chloromethyl, difluoromethyl, perchloromethyl, 2-bromoethyl, perfluoromethyl, and 3-iodocyclopentyl), hydroxyalkyl (such as hydroxymethyl, hydroxyethyl, 2-hydroxypropyl, aminoalkyl (such as aminomethyl, 2-aminoethyl, 3-aminopropyl, and 2-aminopropyl), nitroalkyl, alkylalkyl, and so on. A di($C_1$ alkyl)amino group includes independently selected alkyl groups, to form, for example, methylpropylamino and isopropylmethylamino, in addition dialkylamino groups having two of the same alkyl group such as dimethyl amino or diethylamino.

Third, only stable compounds are intended. For example, where there is an NR'R" group, and R can be an alkenyl group, the double bond is at least one carbon removed from the nitrogen to avoid enamine formation. Similarly, where a dashed line is an optional $sp^2$ bond, if it is absent, the appropriate hydrogen atom(s) is(are) included.

Preferred substitutions for Ar include methyl, methoxy, fluoromethyl, difluoromethyl, perfluoromethyl (trifluoromethyl), 1-fluoroethyl, 2-fluoroethyl, ethoxy, fluoro, chloro, and bromo, and particularly methyl, bromo, chloro, perfluoromethyl, perfluoromethoxy, methoxy, and fluoro. Preferred substitution patterns for Ar are 4-substituted or 3,4-disubstituted phenyl. Compounds of the invention are further described in the next section.

B. Compounds

The invention features the treatment of an allergic condition using one or more compounds of formula (I) as described in the Summary section.

Preferred compounds include those wherein:

(a) one of S, T, Y, and Z is nitrogen;

(b) S and T are $CR^3$ and $CR^2$, respectively;

(c) S, T, Y, and Z are $CR^3$, $CR^2$, $CR^{20}$, and $CR^{21}$, respectively;

(d) (1)Z is N, Y is N, S is $CR^3$, and T is $CR^2$; or (2) S is N, T is N, Y is $CR^{20}$, and Z is $CR^{21}$;

(e) $R^2$ is hydrogen, halogen, $C_{1-5}$ alkoxy, cyano, $R^eR^fN$, or a 5–6 membered heterocyclyl;

(f) $R^3$ is hydrogen, halogen, $C_{1-5}$ alkoxy, $C_{1-5}$ alkyl, cyano, $R^{17}OC=O$, or $R^gR^hN$, where $R^g$ and $R^h$ are H or $C_{1-5}$ alkyl, or are taken together to form a 5–6 membered heterocyclyl;

(g) each of $R^2$ and $R^3$ is independently selected from hydrogen, halogen, and a 5–6 membered heterocyclyl;

(h) $R^5$ and $R^6$ are independently selected from hydrogen and $C_{1-3}$ alkyl;

(i) one of $R^5$ and $R^6$ is H;

(j) $R^5$ and $R^6$ are each H;

(k) one of $R^7$ and $R^8$ is H and the other is 5–7 membered carbocyclyl or heterocyclyl;

(l) $R^7$ and $R^8$ are taken together to form an optionally substituted 5- to 7-membered carbocyclic or heterocyclic ring;

(m) $R^7$ and $R^8$ are taken together to form a six-membered heterocyclyl;

(n) $R^7$ and $R^8$ taken together form a 5–7 membered heterocyclyl optionally N-substituted with $R^t(C=O)$—, $R^tSO_2$-, or $NHR''(C=O)$— wherein $R^t$ is $C_{1-6}$ alkyl, phenyl, or $C_{2-5}$ heterocyclyl and $R''$ is H, $C_{1-6}$ alkyl, phenyl, or $C_{2-5}$ heterocyclyl;

(o) each of $R^c$, $R^e$, $R^m$, and $R^o$ is independently selected from hydrogen, $C_{1-5}$ alkyl, $C_{2-8}$ acyl, ($C_{1-5}$ alkyl)OC=O, and the respective RRNC=O, RSO, $RSO_2$, and $RRNSO_2$ groups;

(p) each of $R^c$, $R^d$, $R^g$, $R^h$, $R^o$, $R^f$, and $R^p$ is independently selected from hydrogen and $C_{1-5}$ alkyl; or, independently, $R^e$ and $R^f$, $R^g$ and $R^h$, or $R^o$ and $R^p$ taken together form an optionally substituted 4- to 7-membered carbocyclic or heterocyclic ring;

(q) $R^e$ and $R^f$ taken together are morpholinyl, piperidinyl, or pyrrolidinyl;

(r) each of $R^{43}$, $R^{44}$, $R^{45}$, $R^{46}$, $R^{47}$, $R^{48}$, $R^i$, $R^j$, $R^k$ and $R^l$ independently is hydrogen or $C_{1-5}$ alkyl;

(s) each of $R^9$, $R^{11}$, $R^{14}$, $R^{15}$, $R^{16}$ and $R^{17}$ is independently $C_{1-5}$ alkyl;

(t) $R^g$ is $C_{1-5}$ alkyl, $C_{2-8}$ acyl, $R^9OC=O$, $R^{18}R^{19}NC=O$, $R^9SO$, $R^9SO_2$, or $R^{18}R^{19}NSO_2$; and $R^h$ is H or $C_{1-5}$ alkyl; alternatively, $R^9$ and $R^h$ can be taken together to form an optionally substituted 5- to 6-membered heterocyclyl;

(u) $R^9$ and $R^h$ are each $C_{1-3}$ alkyl;

(v) $R^{18}$ and $R^{19}$ independently are hydrogen or $C_{1-5}$ alkyl;

(w) n is 0 or 1; or n is 1;

(x) G is $C_{3-4}$ alkanediyl, optionally substituted with hydroxy, halogen, [(L)—$C_{1-5}$ alkylene]amino, or (L)—$C_{1-5}$ alkyloxy;

(y) G is $C_3$ alkanediyl, optionally substituted with hydroxy;

(z) $R^{20}$ and $R^{21}$ are independently selected from hydrogen, halogen, $C_{1-5}$ alkoxy, $C_{1-5}$ alkyl, cyano, nitro, 4–7 membered heterocyclyl, and $R^oR^pN$ or $R^cR^dN$, respectively;

(aa) $R^{20}$ and $R^{21}$ are independently selected from hydrogen, halogen, 5- to 6-membered heterocyclyl, and $R^oR^pN$ or $R^cR^dN$, respectively;

(bb) Ar represents a monocyclic ring, optionally substituted with 1 to 2 substituents selected from halogen, $C_{1-5}$ alkyl, cyano, nitro, $R^{22}R^{23}N$, $C_{1-3}$ haloalkyl, and $C_{1-3}$ haloalkoxy;

(cc) Ar is a six-membered aromatic ring monosubstituted at the 4-position with halogen, methyl, $CF_3$, or $OCF_3$, or disubstituted at the 3-and 4-positions with substituents independently selected from halogen, $CF_3$, methyl, and $OCF_3$;

(dd) each of $R^{22}$, $R^{23}$, and $R^{24}$ is independently hydrogen or $C_{1-5}$ alkyl;

(ee) $R^{25}$ and $R^{26}$ independently are hydrogen or $C_{1-5}$ alkyl, or, alternatively, $R^{25}$ and $R^{26}$ are taken together to form an optionally substituted 4- to 7-membered heterocyclic ring, which ring may be saturated, unsaturated or aromatic;

(ff) $R^{25}$ and $R^{26}$ independently are hydrogen or $C_{1-5}$ alkyl;

(gg) Q is $NR^{33}$ or S;

(hh) Q is $NR^{33}$, $R^{33}$ is H or $C_{2-5}$ heterocyclyl, and $R^{32}$ is H, $C_{1-5}$ alkyl, $C_{1-5}$ hydroxyalkyl, —(C=O)$NR^vR^x$, CHO, or $C_{1-6}$ alkoxycarbonyl, wherein each of $R^v$ and $R^x$ is independently selected from H, $C_{1-5}$ hydroxyalkyl, ($C_{1-5}$ heterocyclyl)-$C_{1-5}$ alkylene, and $C_{1-5}$ aminoalkylene;

(ii) wherein Q is S and $R^{33}$ is $NR^{36}R^{37}(C=O)$— where each of $R^{36}$ and $R^{37}$ are independently selected from hydrogen and $C_{1-5}$ alkyl;

(jj) $R^{35}$ is selected from hydrogen and $C_{1-5}$ alkyl; $R^{36}$ and $R^{37}$ are each independently selected from hydrogen, $C_{1-5}$ alkyl, or, alternatively, $R^{36}$ and $R^{37}$ can be taken together to form an optionally substituted 4- to 7-membered heterocyclic ring;

(kk) Y is nitrogen or $R^{20}C$; Z is nitrogen or $R^{21}C$; T is nitrogen or $R^2C$; S is nitrogen or $R^3C$; provided between 0 and 2 of S, T, Y, and Z are nitrogen; for example 1 of them is N;

(ll) $R^2$ is hydrogen, halogen, hydroxy, $C_{1-5}$ alkoxy, $C_{1-5}$ alkyl, 5- to 6-membered heterocyclyl, or $R^eR^fN$;

(mm) $R^3$ is hydrogen, halogen, $C_{1-5}$ alkoxy, hydroxy, $C_{1-5}$ alkyl, , 5- to 6-membered heterocyclyl, or $R^gR^hN$;

(nn) $R^7$ and $R^8$ independently are taken together to form an optionally substituted 5- to 7-membered unsaturated heterocyclic ring;

(oo) each of $R^a$ $R^e$, $R^m$, and $R^o$ is independently selected from hydrogen, $C_{1-5}$ alkyl, $C_{2-8}$ acyl, ($C_{1-5}$ alkyl)OC=O, and the respective RRNC=O, RSO, $RSO_2$, and $RRNSO_2$ groups;

(pp) each of $R^b$, $R^f$, $R^n$, and $R^p$, is independently selected from hydrogen and $C_{1-5}$ alkyl; each of $R^9$, $R^{11}$, $R^{14}$, $R^{15}$, $R^{16}$, $R^{17}$, $R^{40}$, $R^{41}$ and $R^{42}$ is independently $C_{1-5}$ alkyl; and each of $R^c$, $R^d$, $R^i$, $R^j$, $R^{43}$, $R^{44}$, $R^{45}$, $R^{46}$, $R^{47}$, $R^k$ and $R^l$ are independently are hydrogen or $C_{1-5}$ alkyl;

(qq) $R^g$ is hydrogen, or $C_{1-5}$ alkyl, $C_{2-8}$ acyl, $R^9OC=O$, $R^{18}R^{19}NC=O$, $R^9SO$, $R^9SO_2$, or $R^{18}R^{19}NSO_2$; $R^h$ is hydrogen or $C_{1-5}$ alkyl; alternatively, $R^g$ and $R^h$ can be taken together to form an optionally substituted 4- to 7-membered carbocyclic or heterocyclic ring, which ring may be saturated, unsaturated or aromatic; $R^{18}$ and $R^{19}$ independently are hydrogen or $C_{1-5}$ alkyl; n is 0 or 1;

(rr) G is $C_{3-4}$ alkenediyl or $C_{3-4}$ alkanediyl, optionally substituted with hydroxy, halogen, $C_{1-5}$ alkyloxy, oxo, hydroximino, $CO_2R^k$, $R^kR^lNCO_2$, or (L)—$C_{1-5}$ alkoxy; L is amino, mono- or di-$C_{1-5}$ alkylamino, pyrrolidinyl, morpholinyl, piperidinyl homopiperidinyl, or piperazinyl, available ring nitrogens being optionally with $C_{1-5}$ alkyl, benzyl, $C_{2-5}$ acyl, or $C_{1-5}$ alkyloxycarbonyl;

(ss) $R^{20}$ and $R^{21}$ are independently selected from hydrogen, halogen, $C_{1-5}$ alkoxy, $C_{1-5}$ alkyl, cyano, nitro, and $R^oR^pN$; alternatively, $R^3$ and $R^{20}$ or $R^3$ and $R^{21}$ can be taken together to form an optionally substituted 5- or 6-membered carbocyclic or heterocyclic ring, which ring may be saturated, unsaturated or aromatic; and Ar represents a monocyclic or bicyclic aryl or heteroaryl ring, optionally substituted with hydrogen, halogen, $C_{1-5}$ alkoxy, $C_{1-5}$ alkyl, cyano, nitro, $R^{22}R^{23}N$, $R^{24}SO_2$, $R^{24}OC=O$, $R^{25}R^{26}NC=O$, $CF_3$, $OCF_3$, $SCF_3$, or $C_{1-5}$ alkylthio; $R^{22}$ is hydrogen, $C_{2-5}$ alkyl, phenyl, benzyl, phenethyl, $C_{2-5}$ heteroaryl, $C_{2-8}$ acyl, aroyl, $R^{24}OC=O$, $R^{25}R^{26}NC=O$, $R^{24}SO$, $R^{24}SO_2$, or $R^{25}R^{26}NSO_2$; $R^{23}$ is hydrogen or $C_{1-5}$ alkyl; alternatively, $R^{22}$ and $R^{23}$ can be taken together to form an optionally substituted 4- to 7-membered carbocyclic or heterocyclic ring, which ring may be saturated, unsaturated or aromatic; $R^{24}$ is hydrogen or $C_{1-5}$ alkyl; $R^{25}$ and $R^{26}$ are independently hydrogen or $C_{1-5}$ alkyl; or, alternatively, $R^{25}$ and $R^{26}$ can be taken together to form an optionally substituted 4- to 7-membered carbocyclic or heterocyclic ring, which ring may be saturated, unsaturated or aromatic;

(tt) $R^{32}$ is hydrogen, $C_{1-5}$ alkyl, $C_{1-5}$ hydroxyalkyl, CHO, $C_{2-6}$ acyl, $C_{1-6}$ alkoxycarbonyl, or —(C=O)$NR^yR^x$, wherein each of $R^y$ $R^x$ is independently selected from H, $C_{1-5}$ alkyl, $C_{1-5}$ hydroxyalkyl, $C_{3-8}$ acyloxy, (amino)$C_{1-6}$ alkylene, ($C_{1-5}$ heterocyclyl)$C_{1-5}$ alkylene, or $C_{1-6}$ alkoxycarbonyl; and Q is $NR^{33}$ or S; $R^{33}$ represents hydrogen, $C_{1-5}$ alkyl, phenyl, benzyl, ($C_{2-5}$ heterocyclyl)$C_{1-5}$ alkylene, $C_{2-8}$ acyl, aroyl, $R^{35}OC=O$, $R^{36}R^{37}NC=O$, $R^{35}SO_2$ and $R^{36}R^{37}NSO_2$; $R^{35}$ is selected from hydrogen and $C_{1-5}$ alkyl; $R^{36}$ and $R^{37}$ are each independently selected from hydrogen and $C_{1-5}$ alkyl;

(uu) one of $R^5$ and $R^6$ is H, $R^7$ and $R^8$ are taken together to form an optionally substituted 6-membered carbocyclic or heterocyclic ring; and Ar represents a monocyclic ring, optionally substituted with 1 to 2 substituents selected from halogen, $C_{1-5}$ alkyl, cyano, nitro, $R^{22}R^{23}N$, $CF_3$ and $OCF_3$;

(vv) both $R^5$ and $R^6$ are each H, and (ww) Ar is a six membered ring substituted with halogen, $CF_3$, methyl, halomethyl, or $OCF_3$, at the 3- or 4-position, or disubstituted at the 3- and 4-positions;

(xx) $R^7$ and $R^8$ taken together form pyridinyl, pyrimidinyl, or piperazinyl, optionally N-substituted with —(C=O)$R^t$, $SO_2$—$R^t$, or —(C=O)$NHR''$;

(yy) $R^e$ and $R^f$ taken together are independently morpholinyl, piperidyl, or pyrrolidinyl, optionally substituted;

(zz) the dashed line adjacent C—$R^6$ is absent;

(aaa) or combinations of the above.

Specific preferred compounds include those in the Examples below, such as:

1-[1-{2-Hydroxy-3-[4-(1H-indol-3-yl)-piperidin-1-yl]-propyl}-3-(4-trifluoromethyl-phenyl)-1,4,6,7-tetrahydro-pyrazolo[4,3-c]pyridin-5-yl]-ethanone; 1-[4-(5-Fluoro-1H-indol-3-yl)-piperidin-1-yl]-3-[5-methanesulfonyl-3-(4-trifluoromethyl-phenyl)-4,5,6,7-tetrahydro-pyrazolo[4,3-c]pyridin-1-yl]-propan-2-ol; 1-[3-(4-Bromo-phenyl)-5-methanesulfonyl-4,5,6,7-tetrahydro-pyrazolo[4,3-c]pyridin-1-yl]-3-[4-(5-chloro-1H-indol-3-yl)-piperidin-1-yl]-propan-2-ol; 1-[3-(4-Bromo-phenyl)-5-methanesulfonyl-4,5,6,7-tetrahydro-pyrazolo[4,3-c]pyridin-1-yl]-3-[4-(5-chloro-2-methyl-1H-indol-3-yl)-piperidin-1-yl]-propan-2-ol; 1-[5-Methanesulfonyl-3-(4-trifluoromethyl-phenyl)-4,5,6,7-tetrahydro-pyrazolo[4,3-c]pyridin-1-yl]-3-[4-(5-methyl-1H-indol-3-yl)-piperidin-1-yl]-propan-2-ol; 3-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1H-indole-5-carbonitrile; 1-[5-Methanesulfonyl-3-(4-trifluoromethyl-phenyl)-4,5,6,7-tetrahydro-pyrazolo[4,3-c]pyridin-1-yl]-3-[4-(5-methoxy-1H-indol-3-yl)-piperidin-1-yl]-propan-2-ol; 3-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1H-indole-5-carboxylic acid ethyl ester; 1-[4-(6-Chloro-1H-indol-3-yl)-piperidin-1-yl]-3-[5-methanesulfonyl-3-(4-trifluoromethyl-phenyl)-4,5,6,7-tetrahydro-pyrazolo[4,3-c]pyridin-1-yl]-propan-2-ol; 1-[1-(3-{4-[6-Chloro-1-(2-morpholin-4-yl-ethyl)-1H-indol-3-yl]-piperidin-1-yl}-2-hydroxy-propyl)-3-(4-trifluoromethyl-phenyl)-1,4,6,7-tetrahydro-pyrazolo[4,3-c]pyridin-5-yl]-ethanone; 1-[5-Methanesulfonyl-3-(4-trifluoromethyl-phenyl)-4,5,6,7-tetrahydro-pyrazolo[4,3-c]pyridin-1-yl]-3-[4-(1H-pyrrolo[3,2-b]pyridin-3-yl)-piperidin-1-yl]-propan-2-ol; 1-[5-Methanesulfonyl-3-(4-trifluoromethyl-phenyl)-4,5,6,7-tetrahydro-pyrazolo[4,3-c]pyridin-1-yl]-3-[4-(1H-pyrrolo

[2,3-c]pyridin-3-yl)-piperidin-1-yl]-propan-2-ol; 1-[5-Methanesulfonyl-3-(4-trifluoromethyl-phenyl)-4,5,6,7-tetrahydro-pyrazolo[4,3-c]pyridin-1-yl]-3-[4-(5-oxy-1H-pyrrolo[3,2-c]pyridin-3-yl)-piperidin-1-yl]-propan-2-ol; 1-[4-(5-Dimethylamino-1H-pyrrolo[3,2-b]pyridin-3-yl)-piperidin-1-yl]-3-[5-methanesulfonyl-3-(4-trifluoromethyl-phenyl)-4,5,6,7-tetrahydro-pyrazolo[4,3-c]pyridin-1-yl]-propan-2-ol; 1-[4-(5-Dimethylamino-1H-pyrrolo[2,3-c]pyridin-3-yl)-piperidin-1-yl]-3-[5-methanesulfonyl-3-(4-trifluoromethyl-phenyl)-4,5,6,7-tetrahydro-pyrazolo[4,3-c]pyridin-1-yl]-propan-2-ol; 3-(1-{2-Hydroxy-3-[5-methanesulfonyl-3-(4-trifluoromethyl-phenyl)-4,5,6, 7-tetrahydro-pyrazolo[4,3-c]pyridin-1-yl]-propyl}-piperidin-4-yl)-1H-pyrrolo[2,3-b]pyridine-6-carbonitrile; 1-[5-Methanesulfonyl-3-(4-trifluoromethyl-phenyl)-4,5,6,7-tetrahydro-pyrazolo[4,3-c]pyridin-1-yl]-3-{4-[1-(2-morpholin-4-yl-ethyl)-1H-pyrrolo[2,3-b]pyridin-3-yl]-piperidin-1-yl}-propan-2-ol; 1-[5-Methanesulfonyl-3-(4-trifluoromethyl-phenyl)-4,5,6,7-tetrahydro-pyrazolo[4,3-c]pyrid in-1-yl]-3-[4-(7-morpholin-4-yl-1H-pyrrolo[2,3-c]pyridin-3-yl)-piperidin-1-yl]-propan-2-ol; 1-[4-(6-Fluoro-2-hydroxymethyl-benzo[b]thiophen-3-yl)-piperidin-1-yl]-3-[5-methanesulfonyl-3-(4-trifluoromethyl-phenyl)-4,5,6,7-tetrahydro-pyrazolo[4,3-c]pyridin-1-yl]-propan-2-ol; 6-Fluoro-3-(1-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-benzo[b]thiophene-2-carbaldehyde; 6-Fluoro-3-(1-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-benzo[b]thiophene-2-carboxylic acid methyl ester; 6-Fluoro-3-(1-{3-[5-methanesulfonyl-3-(4-trifluoromethyl-phenyl)-4,5,6,7-tetrahydro-pyrazolo[4,3-c]pyridin-1-yl]-propyl}-piperidin-4-yl)benzo[b]thiophene-2-carboxylic acid amide; and 6-Fluoro-3-(1-{3-[5-methanesulfonyl-3-(4-trifluoromethyl-phenyl)-4,5,6,7-tetrahydro-pyrazolo[4,3-c]pyridin-1-yl]-propyl}-piperidin-4-yl)benzo[b]thiophene-2-carboxylic acid ethylamide.

Furthermore, preferred compounds include those wherein Ar is selected from 4-trifluoromethylphenyl, 4-bromophenyl, 4-chlorophenyl, 4-chloro-3-methylphenyl and 3,4-dichlorophenyl.

More preferred compounds include those in Examples 4, 9, 13, and 26.

Related Compounds

The invention provides the disclosed compounds and closely related, pharmaceutically acceptable forms of the disclosed compounds, such as salts, esters, amides, acids, hydrates or solvated forms thereof; masked or protected forms; and racemic mixtures, or enantiomerically or optically pure forms. Related compounds also include compounds of the invention that have been modified to be detectable, e.g., isotopically labelled with $^{18}F$ for use as a probe in positron emission tomography (PET) or single-photon emission computed tomography (SPECT).

The invention also includes disclosed compounds having one or more functional groups (e.g., hydroxyl, amino, or carboxyl) masked by a protecting group. See, e.g., Greene and Wuts, *Protective Groups in Organic Synthesis*, $3^{rd}$ ed., (1999) John Wiley & Sons, NY. Some of these masked or protected compounds are pharmaceutically acceptable; others will be useful as intermediates. Synthetic intermediates and processes disclosed herein, and minor modifications thereof, are also within the scope of the invention.

Hydroxyl Protecting Groups

Protection for the hydroxyl group includes methyl ethers, substituted methyl ethers, substituted ethyl ethers, substitute benzyl ethers, and silyl ethers.

Substituted Methyl Ethers

Examples of substituted methyl ethers include methyoxymethyl, methylthiomethyl, t-butylthiomethyl, (phenyldimethylsilyl)methoxymethyl, benzyloxymethyl, p-methoxybenzyloxymethyl, (4-methoxyphenoxy)methyl, guaiacolmethyl, t-butoxymethyl, 4-pentenyloxymethyl, siloxymethyl, 2-methoxyethoxymethyl, 2,2,2-trichloroethoxymethyl, bis(2-chloroethoxy)methyl, 2-(trimethylsilyl)ethoxymethyl, tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S,S-dioxido, 1-[(2-chloro-4-methyl)phenyl]-4-methoxypiperidin-4-yl, 1,4-dioxan-2-yl, tetrahydrofuranyl, tetrahydrothiofuranyl and 2,3,3a,4,5,6,7,7a-octahydro-7,8, 8-trimethyl-4,7-methanobenzofuran-2-yl.

Substituted Ethyl Ethers

Examples of substituted ethyl ethers include 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, and benzyl.

Substituted Benzyl Ethers

Examples of substituted benzyl ethers include p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxy)phenyldiphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(Imidazol-1-ylmethyl)bis(4', 4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, and benzisothiazolyl S,S-dioxido.

Silyl Ethers

Examples of silyl ethers include trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, and t-butylmethoxyphenylsilyl.

Esters

In addition to ethers, a hydroxyl group may be protected as an ester. Examples of esters include formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, p-P-phenylacetate, 3-phenylpropionate, 4-oxopentanoate(levulinate), 4,4-(ethylenedithio)pentanoate, pivaloate, adamantoate, crotonate, 4-methoxycrotonate, benzoate, p-phenylbenzoate, 2,4,6-trimethylbenzoate(mesitoate)

Carbonates

Examples of carbonate protecting groups include methyl, 9-fluorenylmethyl, ethyl, 2,2,2-trichloroethyl, 2-(trimethylsilyl)ethyl, 2-(phenylsulfonyl)ethyl, 2-(triphenylphosphonio)ethyl, isobutyl, vinyl, allyl, p-nitrophenyl, benzyl, p-methoxybenzyl, 3,4- dimethoxybenzyl, o-nitrobenzyl, p-nitrobenzyl, S-benzyl thiocarbonate, 4-ethoxy-1-naphthyl, and methyl dithiocarbonate.

Assisted Cleavage

Examples of assisted cleavage include 2-iodobenzoate, 4-azidobutyrate, 4-nitro4-methylpentanoate, o-(dibromomethyl)benzoate, 2-formylbenzenesulfonate, 2-(methylthiomethoxy)ethyl carbonate, 4-(methylthiomethoxy) butyrate, and 2-(methylthiomethoxymethyl)benzoate.

Miscellaneous Esters

Examples of miscellaneous esters include 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate (tigloate), o-(methoxycarbonyl)benzoate, p-P-benzoate, α-naphthoate, nitrate, alkyl N,N,N',N'-tetramethylphosphorodiamidate, N-phenylcarbamate, borate, dimethylphosphinothioyl, and 2,4-dinitrophenylsulfenate.

Sulfonates

Examples of sulfonates include sulfate, methanesulfonate (mesylate), benzylsulfonate, and tosylate.

Amino Protecting Groups

Protection for the amino group includes carbamates, amides, and special —NH protective groups.

Examples of carbamates include methyl and ethyl carbamates, substituted ethyl carbamates, assisted cleavage carbamates, photolytic cleavage carbamates, urea-type derivatives, and miscellaneous carbamates.

Carbamates

Examples of methyl and ethyl carbamates include methyl and ethyl, 9-fluorenylmethyl, 9-(2-sulfo)fluorenylmethyl, 9-(2,7-dibromo)fluorenylmethyl, 2,7-di-t-butyl-[9-(10,10-dioxo-10,10,10,10-tetrahydrothioxanthyl)]methyl, and 4-methoxyphenacyl.

Substituted Ethyl

Examples of substituted ethyl carbamates include 2,2,2-trichloroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'- and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl and diphenylmethyl.

Assisted Cleavage

Examples of assisted cleavage include 2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 2-triphenylphosphonioisopropyl, 1,1-dimethyl-2-cyanoethyl, m-chloro-p-acyloxybenzyl, p-(dihydroxyboryl)benzyl, 5-benzisoxazolylmethyl, and 2-(trifluoromethyl)-6-chromonylmethyl.

Photolytic Cleavage

Examples of photolytic cleavage include m-nitrophenyl, 3,5-dimethoxybenzyl, o-nitrobenzyl, 3,4-dimethoxy-6-nitrobenzyl, and phenyl(o-nitrophenyl)methyl.

Urea-Type Derivatives

Examples of urea-type derivatives include phenothiazinyl-(10)-carbonyl derivative, N'-p-toluenesulfonylaminocarbonyl, and N'-phenylaminothiocarbonyl.

Miscellaneous Carbamates

Examples of miscellaneous carbamates include t-amyl, S-benzyl thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-d imethylcarboxamido) benzyl, 1,1-dimethyl-3-(N,N-dimethylcarboxamido)propyl, 1,1-dimethylpropynyl, di(2-pyridyl)methyl, 2-furanylmethyl, 2-iodoethyl, isobornyl, isobutyl, isonicotinyl, p-(p'-methoxyphenylazo)benzyl, 1-methylcyclobutyl, 1-methylcyclohexyl, 1-methyl-1-cyclopropylmethyl, 1-methyl-1-(3,5-dimethoxyphenyl) ethyl, 1-methyl-1-(p-phenylazophenyl)ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl, and 2,4,6-trimethylbenzyl.

Examples of amides include:

Amides

N-formyl, N-acetyl, N-chloroacetyl, N-trichloroacetyl, N-trifluoroacetyl, N-phenylacetyl, N-3-phenylpropionyl, N-picolinoyl, N-3-pyridylcarboxamide, N-benzoylphenylalanyl derivative, N-benzoyl, N-p-phenylbenzoyl.

Assisted Cleavage

N-o-nitrophenylacetyl, N-o-nitrophenoxyacetyl, N-acetoacetyl, (N'-dithiobenzyloxycarbonylamino)acetyl, N-3-(p-hydroxyphenyl)propionyl, N-3-(o-nitrophenyl) propionyl, N-2-methyl-2-(o-nitrophenoxy)propionyl, N-2-methyl-2-(o-phenylazophenoxy)propionyl, N-4-chlorobutyryl, N-3-methyl-3-nitrobutyryl, N-o-nitrocinnamoyl, N-acetylmethionine derivative, N-o-nitrobenzoyl, N-o-(benzoyloxymethyl)benzoyl, and 4,5-diphenyl-3-oxazolin-2-one.

Cyclic Imide Derivatives

N-phthalimide, N-dithiasuccinoyl, N-2,3-diphenylmaleoyl, N-2,5-dimethylpyrrolyl, N-1,1,4,4-tetramethyidisilylazacyclopentane adduct, 5-substituted 1,3-dimethyl-1,3,5-triazacyclohexan-2-one, 5-substituted 1,3-dibenzyl-1,3,5-triazacyclohexan-2-one, and 1-substituted 3,5-dinitro-4-pyridonyl.

Special —NH Protective Groups

Examples of special NH protective groups include

N-Alkyl and N-Aryl Amines

N-methyl, N-allyl, N-[2-(trimethylsilyl)ethoxy]methyl, N-3-acetoxypropyl, N-(1-isopropyl-4-nitro-2-oxo-3-pyrrolin-3-yl), quaternary ammonium salts, N-benzyl, N-di (4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, and N-2-picolylamine N'-oxide.

Imine Derivatives

N-1,1-dimethylthiomethylene, N-benzylidene, N-p-methoxybenzylidene, N-diphenylmethylene, N-[(2-pyridyl) mesityl]methylene, and N-(N',N'-dimethylaminomethylene).

Protection for the Carbonyl Group

Acyclic Acetals and Ketals

Examples of acyclic acetals and ketals include dimethyl, bis(2,2,2-trichloroethyl), dibenzyl, bis(2-nitrobenzyl) and diacetyl.

Cyclic Acetals and Ketals

Examples of cyclic acetals and ketals include 1,3-dioxanes, 5-methylene-1,3-dioxane, 5,5-dibromo-1,3- dioxane, 5-(2-pyridyl)-1,3-dioxane, 1,3-dioxolanes, 4-bromomethyl-1,3-dioxolane, 4-(3-butenyl)-1,3-dioxolane, 4-phenyl-1,3-dioxolane, 4-(2-nitrophenyl)-1,3-dioxolane, 4,5-dimethoxymethyl-1,3-dioxolane, O,O'-phenylenedioxy and 1,5-dihydro-3H-2,4-benzodioxepin.

Acyclic Dithio Acetals and Ketals

Examples of acyclic dithio acetals and ketals include S,S'-dimethyl, S,S'-diethyl, S,S'-dipropyl, S,S'-dibutyl, S,S'-dipentyl, S,S'-diphenyl, S,S'-dibenzyl and S,S'-diacetyl.

Cyclic Dithio Acetals and Ketals

Examples of cyclic dithio acetals and ketals include 1,3-dithiane, 1,3-dithiolane and 1,5-dihydro-3H-2,4-benzodithiepin.

Acyclic Monothio Acetals and Ketals

Examples of acyclic monothio acetals and ketals include O-trimethylsilyl-S-alkyl, O-methyl-S-alkyl or -S-phenyl and O-methyl-S-2-(methylthio)ethyl.

Cyclic Monothio Acetals and Ketals

Examples of cyclic monothio acetals and ketals include 1,3-oxathiolanes.

Miscellaneous Derivatives

O-Substituted Cyanohydrins

Examples of O-substituted cyanohydrins include O-acetyl, O-trimethylsilyl, O-1-ethoxyethyl and O-tetrahydropyranyl.

Substituted Hydrazones

Examples of substituted hydrazones include N,N-dimethyl and 2,4-dinitrophenyl.

Oxime Derivatives

Examples of oxime derivatives include O-methyl, O-benzyl and O-phenylthiomethyl.

Imines

Substituted Methylene Derivatives, Cyclic Derivatives

Examples of substituted methylene and cyclic derivatives include oxazolidines, 1-methyl-2-(1'-hydroxyalkyl) imidazoles, N,N'-dimethylimidazolidines, 2,3-dihydro-1,3-benzothiazoles, diethylamine adducts, and methylaluminum bis(2,6-di-t-butyl-4-methylphenoxide)(MAD)complex.

Protection for the Carboxyl Group

Esters

Substituted Methyl Esters

Examples of substituted methyl esters include 9-fluorenylmethyl, methoxymethyl, methylthiomethyl, tetrahydropyranyl, tetrahydrofuranyl, methoxyethoxymethyl, 2-(trimethylsilyl)ethoxymethyl, benzyloxymethyl, phenacyl, p-bromophenacyl, α-methylphenacyl, p-methoxyphenacyl, carboxamidomethyl, and N-phthalimidomethyl.

2-Substituted Ethyl Esters

Examples of 2-substituted ethyl esters include 2,2,2-trichloroethyl, 2-haloethyl, ω-chloroalkyl, 2-(trimethylsilyl)ethyl, 2-methylthioethyl, 1,3-dithianyl-2-methyl, 2-(p-nitrophenylsulfenyl)ethyl, 2-(p-toluenesulfonyl)ethyl, 2-(2'-pyridyl)ethyl, 2-(diphenyl phosphino)ethyl, 1-methyl-1-phenylethyl, t-butyl, cyclopentyl, cyclohexyl, allyl, 3-buten-1-yl, 4-(trimethylsilyl)-2-buten-1-yl, cinnamyl, α-methylcinnamyl, phenyl, p-(methylmercapto)phenyl and benzyl.

Substituted Benzyl Esters

Examples of substituted benzyl esters include triphenylmethyl, diphenylmethyl, bis(o-nitrophenyl)methyl, 9-anthrylmethyl, 2-(9,10-dioxo)anthrylmethyl, 5-dibenzosuberyl, 1-pyrenylmethyl, 2-(trifluoromethyl)-6-chromylmethyl, 2,4,6-trimethylbenzyl, p-bromobenzyl, o-nitrobenzyl, p-nitrobenzyl, p-methoxybenzyl, 2,6-dimethoxybenzyl, 4-(methylsulfinyl)benzyl, 4-sulfobenzyl, piperonyl, 4-picolyl and p-P-benzyl.

Silyl Esters

Examples of silyl esters include trimethylsilyl, triethylsilyl, t-butyldimethylsilyl, i-propyldimethylsilyl, phenyldimethylsilyl and di-t-butylmethylsilyl.

Activated Esters

Examples of activated esters include thiols.

Miscellaneous Derivatives

Examples of miscellaneous derivatives include oxazoles, 2-alkyl-1,3-oxazolines, 4-alkyl-5-oxo-1,3-oxazolidines, 5-alkyl-4-oxo-1,3-dioxolanes, ortho esters, phenyl group and pentaaminocobalt(III) complex.

Stannyl Esters

Examples of stannyl esters include triethylstannyl and tri-n-butylstannyl.

Amides and Hydrazides

Amides

Examples of amides include N,N-dimethyl, pyrrolidinyl, piperidinyl, 5,6-dihydrophenanthridinyl, o-nitroanilides, N-7-nitroindolyl, N-8-Nitro-1,2,3,4-tetrahydroquinolyl, and p-P-benzenesulfonamides.

Hydrazides

Examples of hydrazides include N-phenyl and N,N'-diisopropyl hydrazides.

C. Synthesis

The compounds of the present invention may be prepared by conventional synthetic organic chemistry and by matrix or combinatorial methods according to Schemes 1 to 12 below, and Examples 1 to 13. Those of ordinary skill in the art will be able to modify and adapt the guidance provided herein to make the disclosed compounds.

Scheme 1

P = H, tert-butoxycarbonyl (BOC), EtOCO, Ac, etc.

Scheme 2
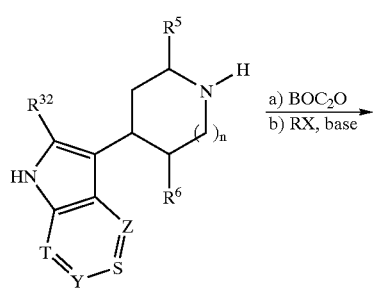
a) BOC₂O
b) RX, base
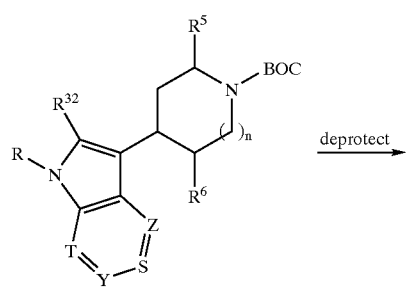
deprotect
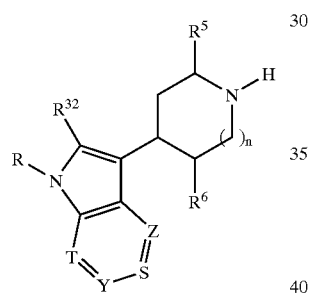
Scheme 3
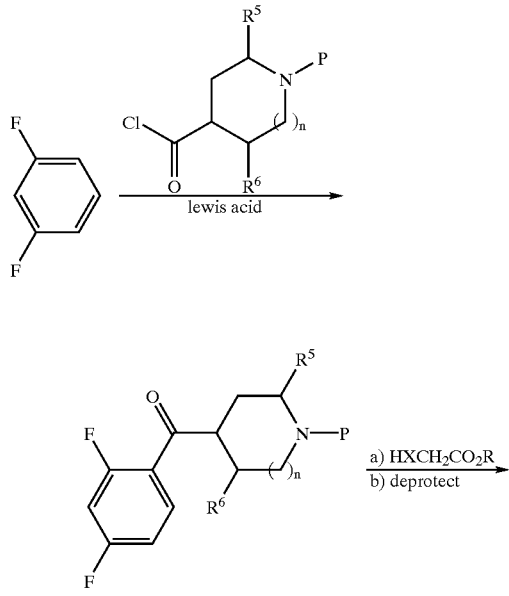
a) HXCH₂CO₂R
b) deprotect
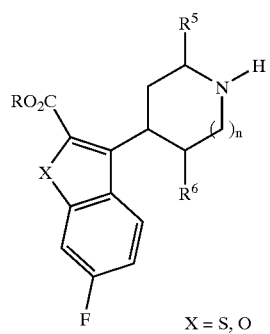
X = S, O
Scheme 4
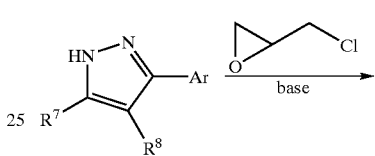
base
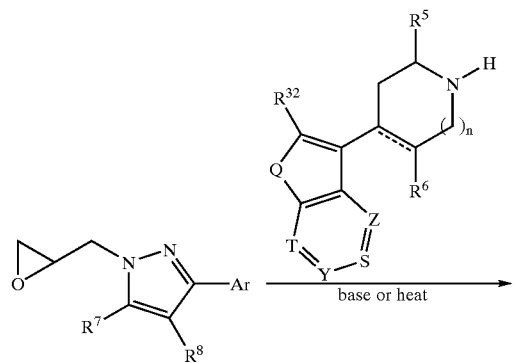
base or heat
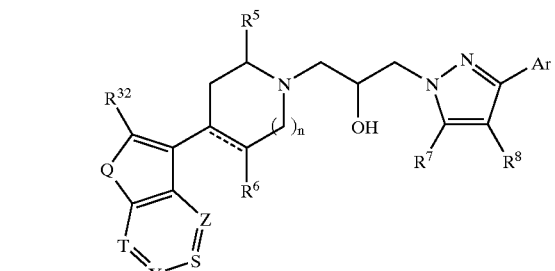

Scheme 5
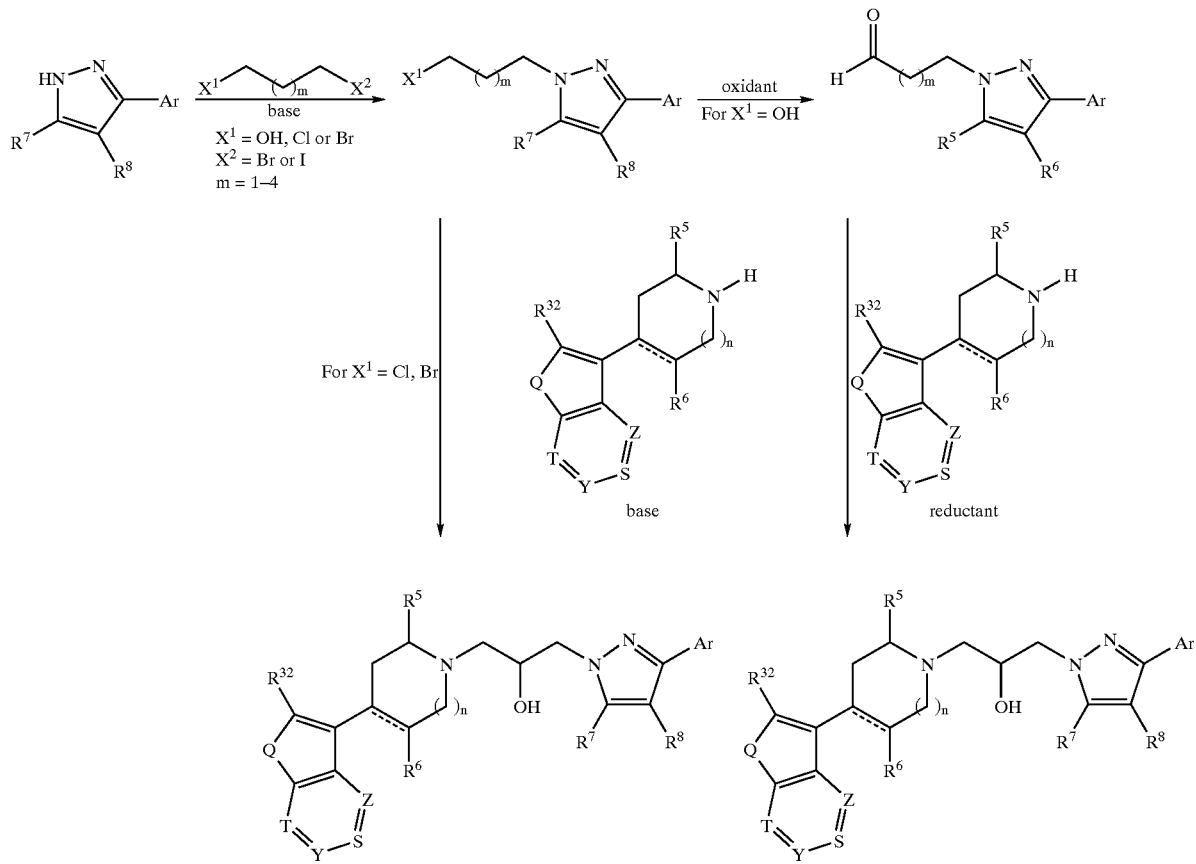
Scheme 6
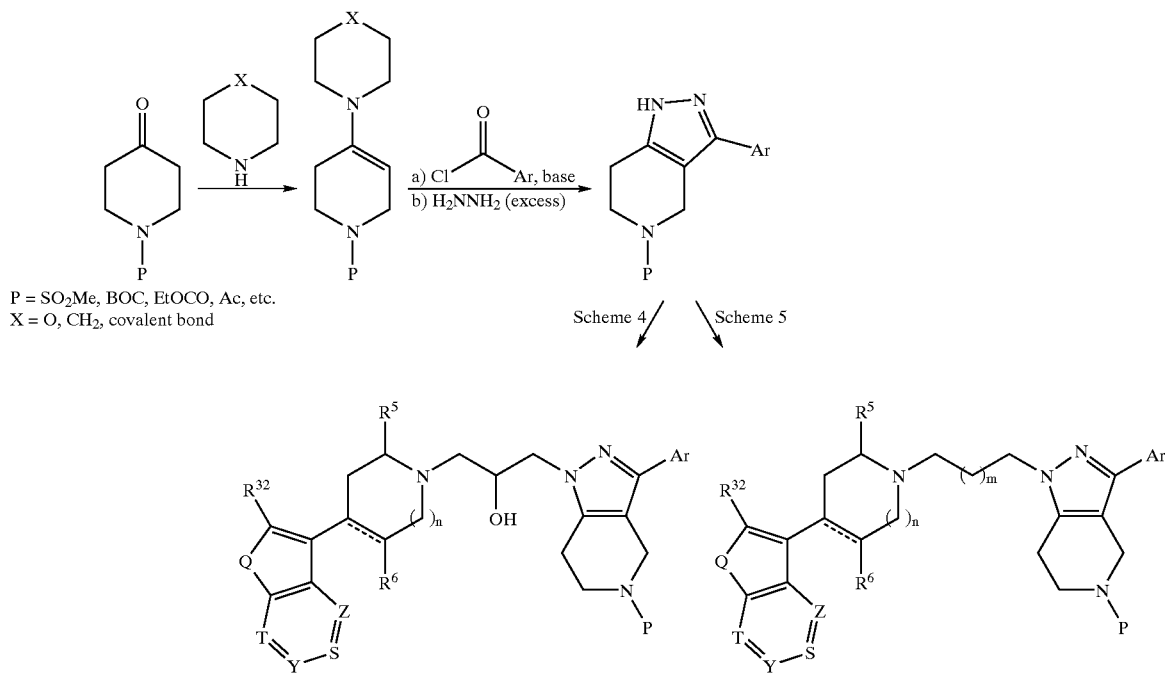
P = SO₂Me, BOC, EtOCO, Ac, etc.
X = O, CH₂, covalent bond Scheme 7
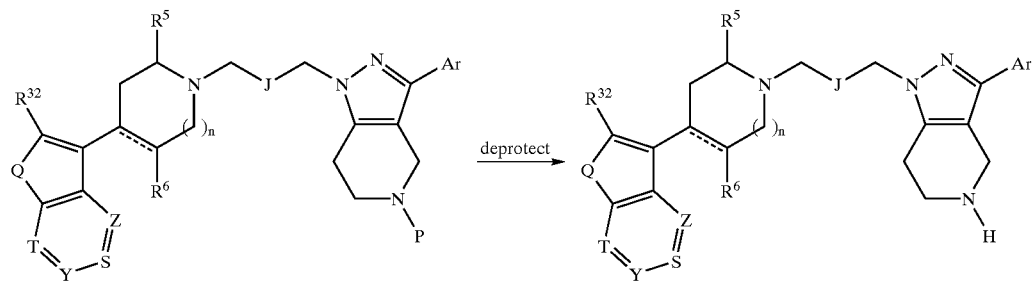
P = BOC, EtOCO, Ac, etc.
J = (CH$_2$)$_m$ or CHOH
m = 1–4
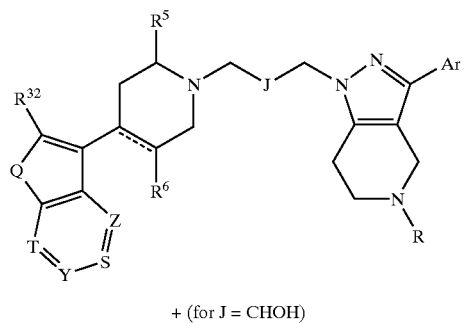
+ (for J = CHOH)
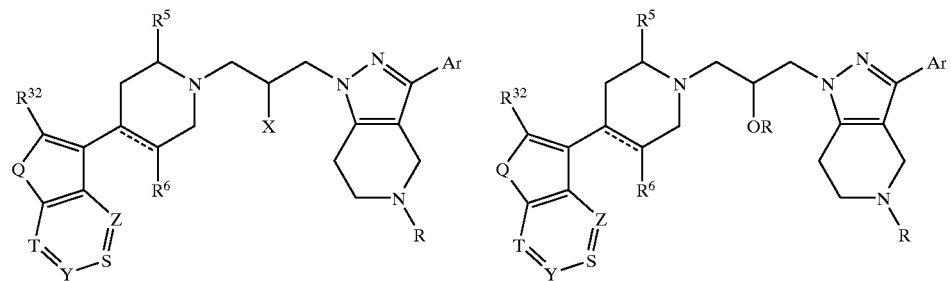
Scheme 8
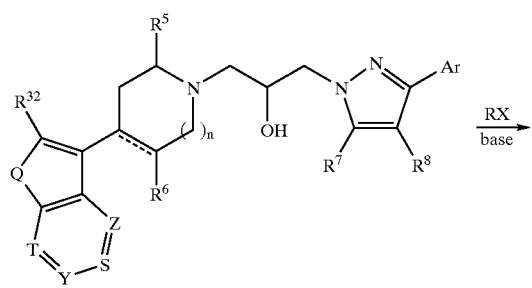
-continued
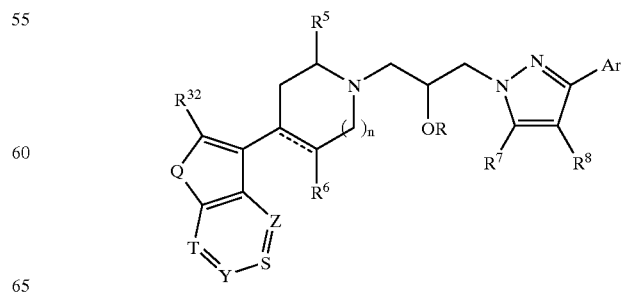

Scheme 9
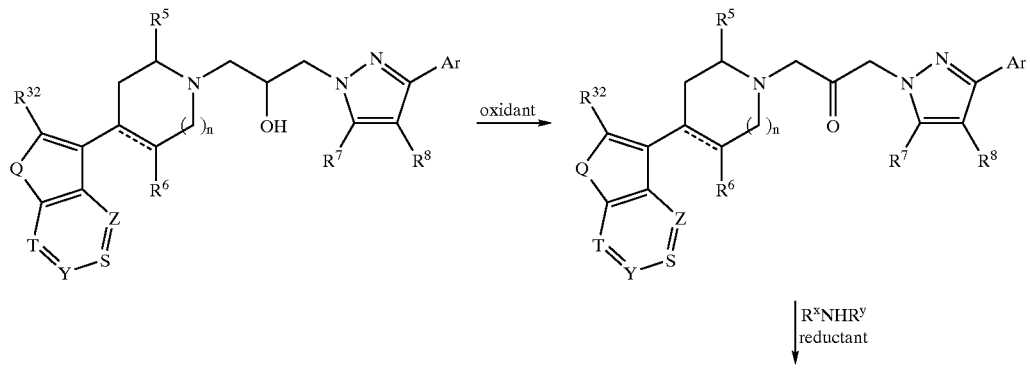
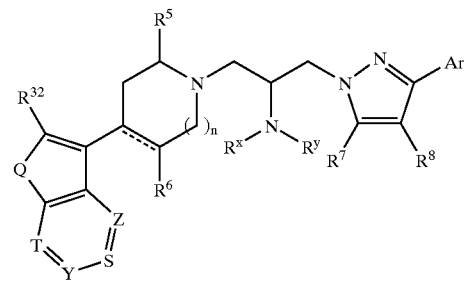
Scheme 10
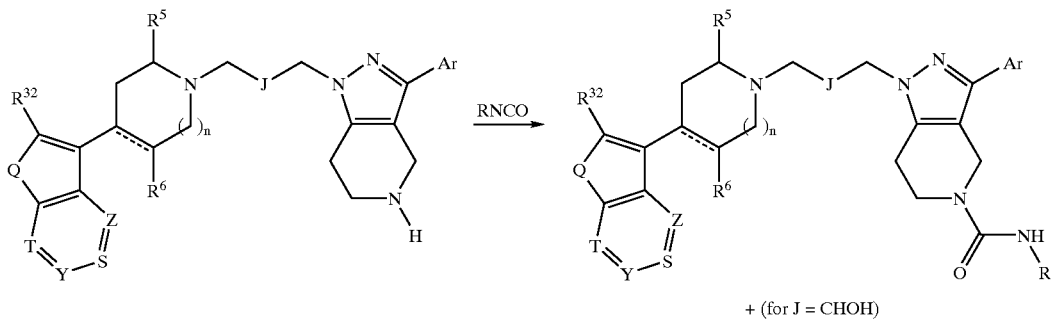
+ (for J = CHOH)
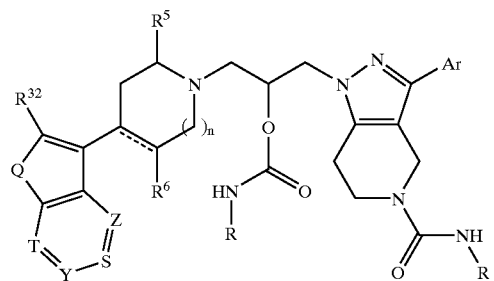

Scheme 11
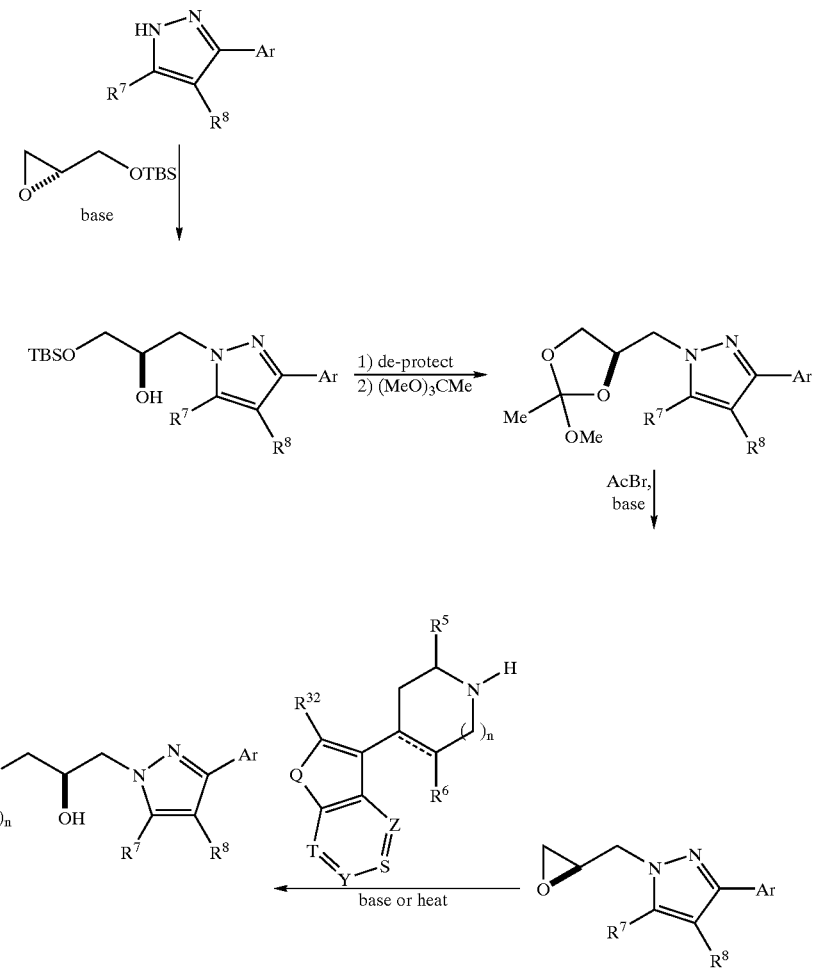
Scheme 12
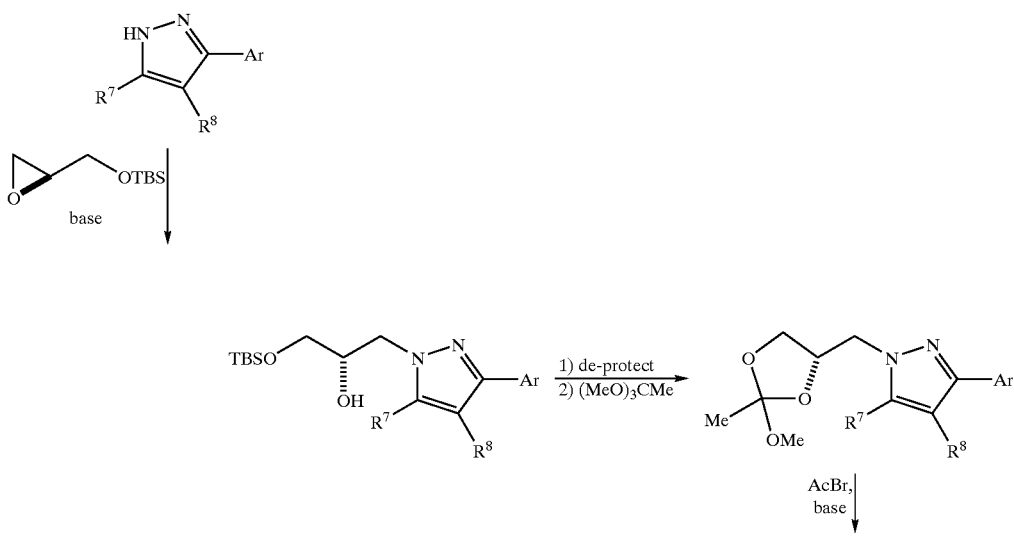

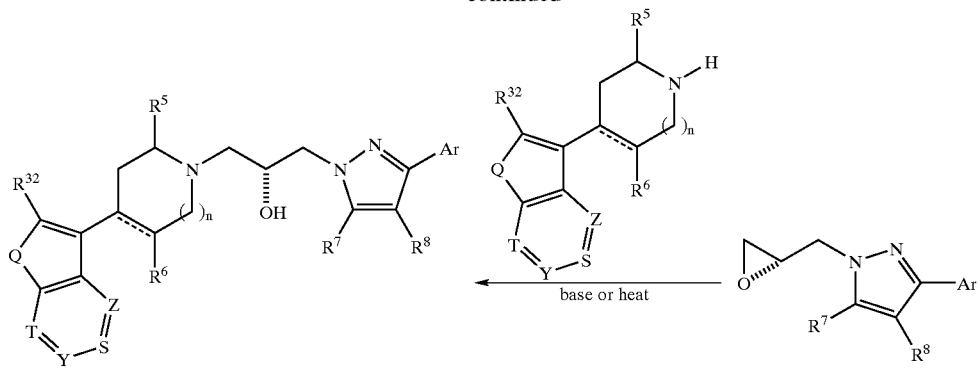

D. Formulation and Administration

The present compounds inhibit the proteolytic activity of human cathepsin S and therefore are useful as a medicine especially in methods for treating patients suffering from allergic disorders or conditions which are modulated or regulated by the inhibition of cathepsin S activity.

The invention features a method for treating a subject with an allergic condition mediated by cathepsin S, said method comprising administering to the subject a therapeutically effective amount of a pharmaceutical composition comprising a compound of the invention. The invention also provides a method for inhibiting cathepsin S activity in a subject, wherein the method comprises administering to the subject a therapeutically effective amount of a pharmaceutical composition comprising a compound of the invention.

In view of their inhibitory effect on the proteolytic activity of human cathepsin S the compounds of the present invention may be formulated into various pharmaceutical forms for administration purposes. To prepare these pharmaceutical compositions, an effective amount of a particular compound, in base or acid addition salt form, as the active ingredient is intimately mixed with a pharmaceutically acceptable carrier.

A carrier may take a wide variety of forms depending on the form of preparation desired for administration. These pharmaceutical compositions are desirably in unitary dosage form suitable, preferably, for oral administration or parenteral injection. For example, in preparing the compositions in oral dosage form, any of the usual pharmaceutical media may be employed. These include water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. In view of their ease in administration, tablets and capsules represent the most advantageous oral dosage unit form, in which case solid pharmaceutical carriers are generally employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Such additives may facilitate the administration to the skin and/or may be helpful for preparing the desired compositions. These compositions may be administered in various ways, e.g., as a transdermal patch, as a spot-on, as an ointment. Acid addition salts of the compounds of formula I, due to their increased water solubility over the corresponding base form, are more suitable in the preparation of aqueous compositions.

It is especially advantageous to formulate the aforementioned pharmaceutical compositions in dosage unit form for ease of administration and uniformity of dosage. Dosage unit form as used in the specification herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Pharmaceutically acceptable acid addition salts include the therapeutically active non-toxic acid addition salt forms which the disclosed compounds are able to form. The latter can conveniently be obtained by treating the base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, palmoic and the like acids. The term addition salt also comprises the solvates which the disclosed compounds, as well as the salts thereof, are able to form. Such solvates are for example hydrates, alcoholates and the like. Conversely the salt form can be converted by treatment with alkali into the free base form.

Stereoisomeric forms defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, sterogenic centers may have the (R)- or (S)-configuration; substituents on bivalent cyclic saturated radicals may have either the cis- or trans-configuration. The invention encompasses stereochemically isomeric forms including diastereoisomers, as well as mixtures thereof in any proportion of the disclosed compounds. The disclosed compounds may also exist in their tautomeric forms. Such forms although not explicitly indicated in the above and following formulae are intended to be included within the scope of the present invention.

Those of skill in the treatment of disorders or conditions mediated by the cathepsin S enzyme could easily determine the effective daily amount from the test results presented hereinafter and other information. In general it is contemplated that a therapeutically effective dose would be from 0.001 mg/kg to 5 mg/kg body weight, more preferably from 0.01 mg/kg to 0.5 mg/kg body weight. It may be appropriate to administer the therapeutically effective dose as two, three, four or more sub-doses at appropriate intervals throughout the day. Said sub-doses may be formulated as unit dosage forms, for example, containing 0.05 mg to 250 mg, and in particular 0.5 to 50 mg of active ingredient per unit dosage form. Examples include 2 mg, 4 mg, 7 mg, 10 mg, 15 mg, 25 mg, and 35 mg dosage forms. Compounds of the invention may also be prepared in time-release or subcutaneous or transdermal patch formulations. Disclosed compound may also be formulated as a spray or other topical or inhalable formulations.

The exact dosage and frequency of administration depends on the particular compound of formula (I) used, the particular condition being treated, the severity of the condition being treated, the age, weight and general physical condition of the particular patient as well as other medication the patient may be taking, as is well known to those skilled in the art. Furthermore, it is evident that said effective daily amount may be lowered or increased depending on the response of the treated patient and/or depending on the evaluation of the physician prescribing the compounds of the instant invention. The effective daily amount ranges mentioned herein are therefore only guidelines.

The next section includes detailed information relating to the preparation, characterization, and use of the disclosed compounds.

E. EXAMPLES

Example 1

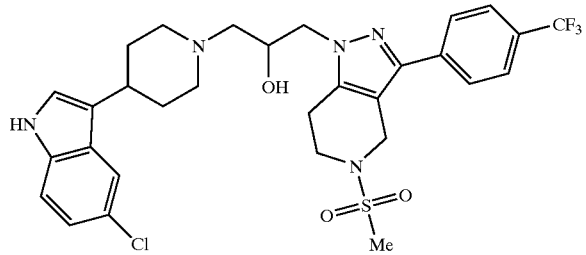

1-[4-(5-Chloro-1H-indol-3-yl)-piperidin-1-yl]-3-[5-methanesulfonyl-3-(4-trifluoromethyl-phenyl)-4,5,6,7-tetrahydro-pyrazolo[4,3-c]pyridin-1-yl]-propan-2-ol A. 1-Methanesulfonyl-piperidin-4-one Potassium carbonate (324 g, 2340 mmol) was added to a solution of 4-piperidone monohydrate hydrochloride (90 g, 586 mmol) in chloroform (300 mL) and water (300 mL). The slurry was cooled to 0° C. and treated with methylsulfonyl chloride (136 mL, 1760 mmol) by dropwise addition over a 1 h period (gas evolution was observed). The reaction mixture was allowed to shake for 72 h and was partitioned between $CH_2Cl_2$ (500 mL) and saturated aqueous $NaHCO_3$ (500 mL). The aqueous layer was extracted with $CH_2Cl_2$ (3×200 mL). The organic layer was washed with 1% $KHSO_4$ (250 mL), dried ($Na_2SO_4$), and concentrated to afford 90.5 g (87%) of a white solid. MS (electrospray): exact mass calculated for $C_6H_{11}NO_3S$, 177.1; m/z found, 178.1 [M+H]$^+$. HPLC (reverse phase conditions): $t_R$=2.19 min. $^1$H NMR (400 MHz, CDCl$_3$): 3.60 (t, J=6.5 Hz, 4H), 2.89 (s, 3H), 2.59 (t, J=6.3 Hz, 4H).

B. 5-Methanesulfonyl-3-(4-trifluoromethyl-phenyl)-4,5,6,7-tetrahydro-1H-pyrazolo[4,3-c]pyridine p-Toluenesulfonic acid (1.34 g, 7.0 mmol) and morpholine (25.83 mL, 296 mmol) were added to a solution of 1-methanesulfonyl-piperidin-4-one (50.0 g, 282 mmol) in benzene (282 mL). The reaction mixture was heated in a flask equipped with a condenser and a Dean-Stark trap at reflux for 15 h. The reaction mixture was cooled and concentrated in vacuo to give the enamine which was used without further purification. The enamine was dissolved in $CH_2Cl_2$ (200 mL) and cooled to 0° C. To this was added triethylamine (47.2 mL, 339 mmol) followed by dropwise addition of 4-trifluoromethylbenzoyl chloride (42.3 mL, 285 mmol) dissolved in $CH_2Cl_2$ (82 mL). The reaction mixture was allowed to warm to room temperature and stirred for 20 h. The reaction mixture was washed with 1 N aqueous HCl (250 mL) and the $CH_2Cl_2$ layer was separated, dried ($Na_2SO_4$), and concentrated. The resulting oil was taken up in ethanol (300 mL) and treated with hydrazine (44.3 mL, 1.41 mol) at 0° C. The reaction mixture was allowed to warm to room temperature and stirred for 24 h. The mixture was concentrated and the resulting solid was filtered with ethanol wash and dried in vacuo to afford 70 g (72%) of 5-methanesulfonyl-3-(4-trifluoromethyl-phenyl)-4,5,6,7-tetrahydro-1H-pyrazolo[4,3-c]pyridine as a white solid. MS (electrospray): exact mass calculated for $C_{14}H_{14}F_3N_3O_2S$, 345.0; m/z found, 346.0 [M+H]$^+$. HPLC (reverse phase conditions): $t_R$=6.33 min. $^1$H NMR (400 MHz, CDCl$_3$): 7.72 (s, 4H), 4.58 (s, 2H), 3.69 (t, J=5.7 Hz, 2H), 2.99 (t, J=5.7 Hz, 2H), 2.92 (s, 3H).

C. 5-Methanesulfonyl-1-oxiranylmethyl-3-(4-trifluoromethyl-phenyl)-4,5,6,7-tetrahydro-1H-pyrazolo[4,3-c]pyridine 5-Methanesulfonyl-3-(4-trifluoromethyl-phenyl)-4,5,6,7-tetrahydro-1H-pyrazolo[4,3-c]pyridine (10.0 g, 29.0 mmol) and epichlorohydrin (24 mL, 307 mmol) were set stirring in DMF (150 mL) containing $Cs_2CO_3$ (10.4 g, 31.9 mmol). After stirring at room temperature for 4 days the mixture was evaporated, brought up in EtOAc and washed with water. The organics were dried (MgSO$_4$) and evaporated to give a light yellow solid. Column chromatography (silica, 5% acetone/$CH_2Cl_2$) gave 4.1 g (35%) of a white solid. TLC (silica, 5% acetone/$CH_2Cl_2$): R$_f$=0.28. MS (electrospray): exact mass calculated for $C_{17}H_{18}F_3N_3O_3S$, 401.10; m/z found, 402.1 [M+H]$^+$. $^1$H NMR (400 MHz, CDCl$_3$); 7.84 (d, J=8.3 Hz, 2H), 7.79 (d, J=8.3 Hz, 2H), 4.70–4.62 (m, 3H), 4.25 (d, J=5.4 Hz, 1H), 3.90–3.70 (m, 2H), 3.47 (m, 1H), 3.10–2.9 (m, 6H), 2.65–2.60 (m, 1H).

D. 4-(5-Chloro-1H-indol-3-yl)-3,6-dihydro-2H-pyridine-1-carboxylic acid tert-butyl ester 5-Chloro-1H-indole (3.2 g, 20 mmol), 4-oxo-piperidine-1-carboxylic acid tert-butyl ester (7.97 g, 40 mmol) and potassium hydroxide (4.5 g, 80 mmol) were added in MeOH (40 mL) and heated to reflux for 16 h. The reaction mixture was then cooled to room temperature and poured into ice water (200 mL). The mixture were extracted with 10% MeOH/CH$_2$Cl$_2$ (5×100 mL). The organic extracts was dried over Na$_2$SO$_4$ and concentrated to form a solid. The solid was washed with MeOH (100 mL), filtered and dried to give a light yellow solid 6.3 g (94%). TLC (silica, 5% MeOH/CH$_2$Cl$_2$): R$_f$=0.8. MS (electrospray): exact mass calculated for $C_{18}H_{21}ClN_2O_2$, 332.12; m/z found, 355.0 [M$^+$+Na]. $^1$H NMR (CDCl$_3$, 400 MHz): 8.26 (br s, 1H), 7.83 (d, J=1.76 Hz, 1H), 7.28 (d, J=8.80 Hz, 1H), 7.19–7.14 (m, 2H), 6.09 (br s, 1H), 4.15–4.10 (m, 2H), 3.66 (t, J=5.67 Hz, 2H), 2.56–2.49 (m, 2H), 1.50 (s, 9H).

E. 4-(5-Chloro-1H-indol-3-yl)-piperidine-1-carboxylic acid tert-butyl ester 4-(5-Chloro-1H-indol-3-yl)-3,6-dihydro-2H-pyridine-1-carboxylic acid tert-butyl ester (6.3 g, 18.9 mmol) in EtOH (125 mL) containing PtO$_2$ (1 g) was placed on a Parr hydrogenator at 60 psi H$_2$. After 18 h the mixture was filtered through celite and evaporated to give a white solid 6.0 g (94%). TLC (silica, 5% MeOH/CH$_2$Cl$_2$): R$_f$=0.8. MS (electrospray): exact mass calculated for C$_{18}$H$_{23}$ClN$_2$O$_2$, 334.14; m/z found, 335.1 [M$^+$+H]. $^1$H NMR (CDCl$_3$, 400 MHz) 8.46 (br s, 1H), 7.51 (d, J=8.41 Hz, 1H), 7.32 (d, J=1.57 Hz, 1H), 7.06 (dd, J=6.46 Hz, 2.15 Hz, 1H), 6.92 (d, J=2.35 Hz, 1H), 4.24 (d, J=13.11 Hz, 2H), 2.98–2.84 (m, 3H), 2.00 (d, J=12.72 Hz, 2H), 1.69–1.55 (m, 2H), 1.50 (s, 9H).

F. 5-Chloro-3-piperidin-4-yl-1H-indole 4-(5-Chloro-1H-indol-3-yl)-piperidine-1-carboxylic acid tert-butyl ester (3.4 g, 10.2 mmol) was set stirring in 1:1 TFA/CH$_2$Cl$_2$. After 45 min the mixture was evaporated and the golden oil brought up in Et$_2$O. A solid formed and was filtered, washed with Et$_2$O and air dried to give 3.5 g (97%) of a white solid as a TFA salt. MS (electrospray): exact mass calculated for C$_{12}$H$_{15}$ClN$_2$, 234.09; m/z found, 235.1 [M$^+$+H].

G. 1-[4-(5-Chloro-1H-indol-3-yl)-piperidin-1-yl]-3-[5-methanesulfonyl-3-(4-trifluoromethyl-phenyl)-4,5,6,7-tetrahydro-pyrazolo[4,3-c]pyridin-1-yl]-propan-2-ol 5-Chloro-3-piperidin-4-yl-1H-indole (350 mg, 1.00 mmol) and 5-methanesulfonyl-1-oxiranylmethyl-3-(4-trifluoromethyl-phenyl)-4,5,6,7-tetrahydro-1H-pyrazolo[4,3-c]pyridine (401 mg, 1.00 mmol) were set stirring in EtOH (20 mL) containing Et$_3$N (215 μL, 1.54 mmol) at 80° C. After 16 h the mixture was cooled, evaporated, brought up in CH$_2$Cl$_2$ and washed with water. The organics were dried over Na$_2$SO$_4$ and concentrated. Column chromatography (silica, 0–10% MeOH/CH$_2$Cl$_2$) provided 551 mg (88%) of a white solid. TLC (silica, 10% MeOH/CH$_2$Cl$_2$): R$_f$=0.8. MS (electrospray): exact mass calculated for C$_{30}$H$_{33}$ClF$_3$N$_5$O$_3$S, 635.19; m/z found, 636.2 [M$^+$+H]. $^1$H NMR (CDCl$_3$, 400 MHz): 8.82 (br s, 1H), 7.68 (d, J=8.41 Hz, 2H), 7.61 (d, J=8.6 Hz, 2H), 7.54 (br s, 1H), 7.16 (d, J=8.41 Hz, 1H), 7.03 (dd, J=7.0 Hz, 1.6 Hz, 1H), 6.85 (br s, 1H), 4.43 (dd, J=25.2 Hz, 14.6 Hz, 2H), 4.30–4.05 (m, 3H), 4.00–3.88 (m, 1H), 3.62–3.50 (m, 1H), 3.47–3.35 (m, 1H), 3.02–2.89 (m, 2H), 2.88–2.81 (m, 2H), 2.79 (s, 3H), 2.72–2.60 (m, 1H), 2.47–2.28 (m, 3H), 2.12–2.00 (m, 1H), 1.96–1.85 (m, 2H), 1.74–1.50 (m, 2H).

Example 2

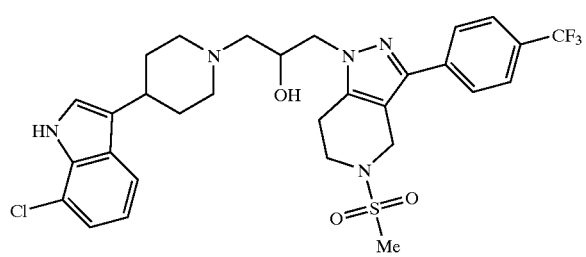

1-[4-(7-Chloro-1H-indol-3-yl)-piperidin-1-yl]-3-[5-methanesulfonyl-3-(4-trifluoromethyl-phenyl)-4,5,6,7-tetrahydro-pyrazolo[4,3-c]pyridin-1-yl]-propan-2-ol A. 4-(7-Chloro-1H-indol-3-yl)-3,6-dihydro-2H-pyridine-1-carboxylic acid tert-butyl ester 7-Chloro-1H-indole (3.2 g, 20 mmol), 4-oxo-piperidine-1-carboxylic acid tert-butyl ester (7.97 g, 40 mmol) and potassium hydroxide (4.5 g, 80 mmol) were added in MeOH (40 mL) and heated to reflux for 16 h. The reaction mixture was then cooled to room temperature and poured into ice water (200 mL). The mixture was extracted with 10% MeOH/CH$_2$Cl$_2$ (5×100 mL). The organic extracts was dried over Na$_2$SO$_4$ and concentrated to form a solid. The solid was washed with MeOH (100 mL), filtered and dried to give a light yellow solid 6.3 g (94%). TLC (silica, 5% MeOH/CH$_2$Cl$_2$): R$_f$=0.8. MS (electrospray): exact mass calculated for C$_{18}$H$_{21}$ClN$_2$O$_2$, 332.12; m/z found, 355.0 [M$^+$+Na]. $^1$H NMR (CDCl$_3$, 400 MHz): 8.26 (br s, 1H), 7.83 (d, J=1.76 Hz, 1H), 7.28 (d, J=8.80 Hz, 1H), 7.19–7.14 (m, 2H), 6.09 (br s, 1H), 4.15–4.10 (m, 2H), 3.66 (t, J=5.67 Hz, 2H), 2.56–2.49 (m, 2H), 1.50 (s, 9H).

B. 4-(7-Chloro-1H-indol-3-yl)-piperidine-1-carboxylic acid tert-butyl ester 4-(7-Chloro-1H-indol-3-yl)-3,6-dihydro-2H-pyridine-1-carboxylic acid tert-butyl ester (6.3 g, 18.9 mmol) in EtOH (125 mL) containing PtO$_2$ (1 g) was placed on a Parr hydrogenator at 60 psi H$_2$. After 18 h the mixture was filtered through celite and evaporated to give a white solid 6.0 g (94%). TLC (silica, 5% MeOH/CH$_2$Cl$_2$): R$_f$=0.8. MS (electrospray): exact mass calculated for C$_{18}$H$_{23}$ClN$_2$O$_2$, 334.14; m/z found, 335.1 [M$^+$+H]. $^1$H NMR (CDCl$_3$, 400 MHz): 8.46 (br s, 1H), 7.51 (d, J=8.41 Hz, 1H), 7.32 (d, J=1.57 Hz, 1H), 7.06 (dd, J=6.46 Hz, 2.15 Hz, 1H), 6.92 (d, J=2.35 Hz, 1H), 4.24 (d, J=13.11 Hz, 2H), 2.98–2.84 (m, 3H), 2.00 (d, J=12.72 Hz, 2H), 1.69–1.55 (m, 2H), 1.50 (s, 9H).

C. 7-Chloro-3-piperidin-4-yl-1H-indole 4-(7-Chloro-1H-indol-3-yl)-piperidine-1-carboxylic acid tert-butyl ester (3.4 g, 10.2 mmol) was set stirring in 1:1 TFA/CH$_2$Cl$_2$. After 45 min the mixture was evaporated and the golden oil brought up in Et$_2$O. A solid formed and was filtered, washed with Et$_2$O and air dried to give 3.5 g (97%) of a white solid. MS (electrospray): exact mass calculated for C$_{12}$H$_{15}$ClN$_2$, 234.09; m/z found, 235.1 [M$^+$+H].

D. 1-[4-(7-Chloro-1H-indol-3-yl)-piperidin-1-yl]-3-[5-methanesulfonyl-3-(4-trifluoromethyl-phenyl)-4,5,6,7-tetrahydro-pyrazolo[4,3-c]pyridin-1-yl]-propan-2-ol 7-Chloro-3-piperidin-4-yl-1H-indole (341 mg, 0.97 mmol) and 5-methane-sulfonyl-1-oxiranylmethyl-3-(4-trifluoromethyl-phenyl)-4,5,6,7-tetrahydro-1H-pyrazolo[4,3-c]pyridine (130 mg, 0.32 mmol) were set stirring in EtOH (15 mL) containing Et$_3$N (135 μL, 0.97 mmol) at 80° C. After 16 h the mixture was cooled, evaporated, brought up in CH$_2$Cl$_2$ and washed with water. The organics were dried over Na$_2$SO$_4$ and concentrated. Column chromatography (silica, 0–10% MeOH/CH$_2$Cl$_2$) gave 120 mg (65%) of a white solid. TLC (silica, 10% MeOH/CH$_2$Cl$_2$): R$_f$=0.7. MS (electrospray): exact mass calculated for C$_{30}$H$_{33}$ClF$_3$N$_5$O$_3$S, 635.19; m/z found, 636.2 [M$^+$+H]. $^1$H NMR (CDCl$_3$, 400 MHz): 8.55 (br s, 1H), 7.70 (d, J=8.22 Hz, 2H), 7.63 (d, J=8.4 Hz, 2H), 7.49 (d, J=9.4 Hz, 1H), 7.14 (d, J=7.8 Hz, 1H), 7.00 (t, J=8.02 Hz, 1H), 6.94 (br s, 1H), 4.51 (dd, J=12.5 Hz, 14.5 Hz, 2H), 4.25–4.11 (m, 3H), 4.07–3.95 (m, 1H), 3.73–3.61 (m, 1H), 3.61–3.50 (m, 1H), 3.11–2.98 (m, 2H), 2.88–2.85 (m, 2H), 2.83 (s, 3H), 2.82–2.72 (m, 1H), 2.55–2.38 (m, 3H), 2.24–2.10 (m, 1H), 2.05–1.90 (m, 2H), 1.82–1.61 (m, 2H).

Example 3

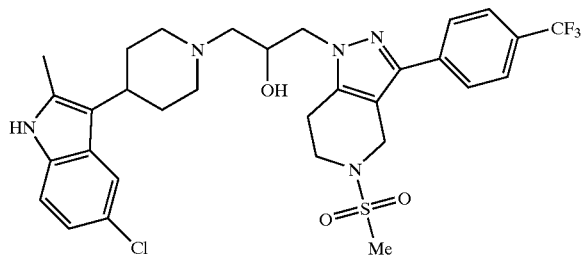

1-[4-(5-Chloro-2-methyl-1H-indol-3-yl)-piperidin-1-yl]-3-[5-methanesulfonyl-3-(4-trifluoromethyl-phenyl)-4,5,6,7-tetrahydro-pyrazolo[4,3-c]pyridin-1-yl]-propan-2-ol A. 4-(5-Chloro-2-methyl-1H-indol-3-yl)-3,6-dihydro-2H-pyridine-1-carboxylic acid tert-butyl ester 5-Chloro-2-methyl-1H-indole (3.3 g, 20 mmol), 4-oxo-piperidine-1-carboxylic acid tert-butyl ester (7.97 g, 40 mmol) and potassium hydroxide (4.5 g, 80 mmol) were added in MeOH (40 mL) and heated to reflux for 16 h. The reaction mixture was then cooled to room temperature and poured into ice water (200 mL). The mixture was extracted with 10% MeOH/$CH_2Cl_2$ (5×100 mL). The organic extracts was dried over $Na_2SO_4$ and concentrated to form a solid. The solid was washed with MeOH (100 mL), filtered and dried to give a light yellow solid 6.2 g (90%). TLC (silica, 5% MeOH/$CH_2Cl_2$): $R_f$=0.8. MS (electrospray): exact mass calculated for $C_{19}H_{23}ClN_2O_2$, 346.14; m/z found, 347.1 [$M^+$+H].

B. 4-(5-Chloro-2-methyl-1H-indol-3-yl)-piperidine-1-carboxylic acid tert-butyl ester 4-(5-Chloro-2-methyl-1H-indol-3-yl)-3,6-dihydro-2H-pyridine-1-carboxylic acid tert-butyl ester (6.2 g, 17.9 mmol) in EtOH (125 mL) containing $PtO_2$ (1 g) was placed on a Parr hydrogenator at 60 psi $H_2$. After 18 h the mixture was filtered through celite and evaporated to give a white solid 6.2 g (99%). TLC (silica, 5% MeOH/$CH_2Cl_2$): $R_f$=0.8. MS (electrospray): exact mass calculated for $C_{19}H_{25}ClN_2O_2$, 348.16; m/z found, 349.1 [$M^+$+H].

C. 5-Chloro-2-methyl-3-piperidin-4-yl-1H-indole 4-(5-Chloro-2-methyl-1H-indol-3-yl)-piperidine-1-carboxylic acid tert-butyl ester (6.2 g, 107.8 mmol) was set stirring in 1:1 TFA/$CH_2Cl_2$. After 45 min the mixture was evaporated and the golden oil brought up in $Et_2O$. A solid formed and was filtered, washed with $Et_2O$ and air dried to give 6.2 g (95%) of a white solid as a TFA salt. MS (electrospray): exact mass calculated for $C_{14}H_{17}ClN_2$, 248.11; m/z found, 249.1 [$M^+$+H].

D. 1-[4-(5-Chloro-2-methyl-1H-indol-3-yl)-piperidin-1-yl]-3-[5-methanesulfonyl-3-(4-trifluoromethyl-phenyl)-4,5,6,7-tetrahydro-pyrazolo[4,3-c]pyridin-1-yl]-propan-2-ol 5-Chloro-2-methyl-3-piperidin-4-yl-1H-indole (480 mg, 1.32 mmol) and 5-methanesulfonyl-1-oxiranylmethyl-3-(4-trifluoromethyl-phenyl)-4,5,6,7-tetrahydro-1H-pyrazolo[4,3-c]pyridine (177 mg, 0.44 mmol) were set stirring in EtOH (20 mL) containing $Et_3N$ (215 µL, 1.54 mmol) at 80° C. After 16 h the mixture was cooled, evaporated, brought up in $CH_2Cl_2$ and washed with water. The organics were dried over $Na_2SO_4$ and concentrated. Column chromatography (silica, 0–10% MeOH/$CH_2Cl_2$) gave 169 mg (62%) of a white solid. TLC (silica, 10% MeOH/$CH_2Cl_2$): $R_f$=0.6. MS (electrospray): exact mass calculated for $C_{31}H_{35}ClF_3N_5O_3S$, 649.21; m/z found, 650.2 [$M^+$+H]. $^1$H NMR ($CDCl_3$, 400 MHz): 8.00 (s, 1H), 7.70 (d, J=8.11 Hz, 2H), 7.64 (d, J=8.41 Hz, 2H), 7.57 (d, J=1.96 Hz, 1H), 7.12 (d, J=8.61 Hz, 1H), 6.99 (dd, J=6.85 Hz, 1.96 Hz, 1H), 4.53 (dd, J=14.28 Hz, 12.91 Hz, 2H), 4.26–4.14 (m, 2H), 4.09–3.99 (m, 1H), 3.75–3.65 (m, 1H), 3.64–3.54 (m, 1H), 3.14–3.02 (m, 2H), 3.00–2.89 (m, 2H), 2.86 (s, 3H), 2.76–2.63 (m, 1H), 2.54–2.45 (m, 2H), 2.45–2.36 (m, 1H), 2.34 (s, 3H), 2.25–2.00 (m, 3H), 1.77–1.63 (m, 2H).

Example 4

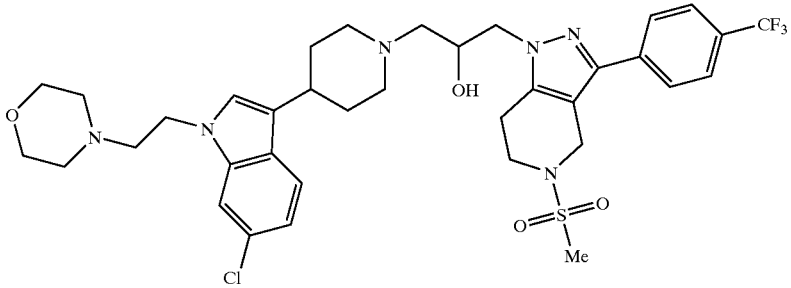

1-{4-[6-Chloro-1-(2-morpholin-4-yl-ethyl)-1H-indol-3-yl]-piperidin-1-yl}-3-[5-methanesulfonyl-3-(4-trifluoromethyl-phenyl)-4,5,6,7-tetrahydro-pyrazolo[4,3-c]pyridin-1-yl]-propan-2-ol A. 6-Chloro-3-piperidin-4-yl-1H-indole 6-Chloro-1H-indole (3.2 g, 20 mmol), piperidin-4-one monohydrate (6.1 g, 40 mmol) and potassium hydroxide (4.5 g, 80 mmol) were added in MeOH (40 mL) and heated to reflux for 16 h. The reaction mixture was then cooled to room temperature and poured into ice water (200 mL). The mixture was extracted with 10% MeOH/$CH_2Cl_2$ (5×100 mL). The organic extracts were dried over $Na_2SO_4$ and concentrated. Column chromatography (silica, 20–100% MeOH/$CH_2Cl_2$ with 2% $NH_4OH$) to obtain 5.8 9 (100%) of a yellow solid. The solid (5.8 g, 20 mmol) in EtOH (150 mL) containing $PtO_2$ (1 g) was placed on a Parr hydrogenator at 60 psi $H_2$. After 18 h the mixture was filtered through celite and evaporated to give an off white solid 4.6 g (97%). MS (electrospray): exact mass calculated for $C_{13}H_{15}ClN_2$, 234.09; m/z found, 235.0 [$M^+$+H].

B. 4-(6-Chloro-1H-indol-3-yl)-piperidine-1-carboxylic acid tert-butyl ester

To a solution of 6-chloro-3-piperidin-4-yl-1H-indole (4.6 g, 19.5 mmol) in DMF (20 mL) was added di-tert-butyl dicarbonate (4.6 g, 21.4 mmol). The reaction mixture was stirred at room temperature for 6 h. The reaction mixture was dissolved in EtOAc (400 mL), washed with water (3×50 mL), brine (1×50 mL). The organic layer was dried over $Na_2SO_4$ and concentrated. Column chromatography (silica, 20–50% EtOAc/hexanes) gave 4.2 g (64%) of the desired product. TLC (silica, 20% EtOAc/hexanes): $R_f$=0.24. MS (electrospray): exact mass calculated for $C_{18}H_{23}ClN_2O_2$, 334.14; m/z found, 335.1 [M$^+$+H]. $^1$H NMR (CDCl$_3$, 400 MHz), 8.46 (br s, 1H), 7.42 (d, J=8.61 Hz, 1H), 7.14 (d, J=1.57 Hz, 1H), 6.96 (dd, J=6.65 Hz, 1.76 Hz, 1H), 6.74 (s, 1H), 4.14 (br s, 2H), 2.89–2.70 (m, 3H), 1.90 (d, J=12.13, 2H), 1.65–1.50 (m, 2H), 1.41 (s, 9H).

C. 4-[6-Chloro-1-(2-morpholin-4-yl-ethyl)-1H-indol-3-yl]-piperidine-1-carboxylic acid tert-butyl ester 4-(6-Chloro-1H-indol-3-yl)-piperidine-1-carboxylic acid tert-butyl ester (2.0 g, 5.95 mmol) was dissolved in THF (30 mL). At 0° C., potassium bis(trimethylsilyl)amide (2.37 g, 11.9 mmol) was added. The reaction mixture was stirred at room temperature for 1 h. 4-(2-Chloro-ethyl)-morpholine hydrochloride (1.8 g, 11.9 mmol) was added and stirred at room temperature for an additional 1 h. The mixture was dissolved in EtOAC (250 mL) and washed with water (2×30 mL) and brine (30 mL). The organics were dried over $Na_2SO_4$ and concentrated. Column chromatography (silica, 0–5% MeOH/CH$_2$Cl$_2$) provided 2.6 g (97%) of a white solid. TLC (silica, 5% MeOH/CH$_2$Cl$_2$): $R_f$=0.67. MS (electrospray): exact mass calculated for $C_{24}H_{34}ClN_3O_3$, 447.23; m/z found, 448.2 [M$^+$+H]. $^1$H NMR (CDCl$_3$, 400 MHz): 7.45 (d, J=8.61 Hz, 1H), 7.27 (d, J=1.57 Hz, 1H), 6.99 (dd, J=6.65 Hz, 1.76 Hz, 1H), 6.84 (s, 1H), 4.18 (br s, 2H), 4.06 (t, J=6.85 Hz, 2H), 3.69–3.60 (m, 4H), 2.92–2.80 (m, 2H), 2.69–2.60 (m, 3H), 2.44 (t, J=4.89 Hz, 2H), 2.40 (t, J=4.30 Hz, 2H), 1.94 (d, J=12.13, 2H), 1.65–1.50 (m, 2H), 1.45 (s, 9H).

D. 6-Chloro-1-(2-morpholin-4-yl-ethyl)-3-piperidin-4-yl-1H-indole

4-[6-Chloro-1-(2-morpholin-4-yl-ethyl)-1H-indol-3-yl]-piperidine-1-carboxylic acid tert-butyl ester (2.6 g, 5.81 mmol) was set stirring in 1:1 TFA/CH$_2$Cl$_2$. After 45 min the mixture was evaporated and the golden oil brought up in Et$_2$O. A solid formed and was filtered, washed with Et$_2$O and air dried to give 2.5 g (95%) of a white solid. MS (electrospray): exact mass calculated for $C_{19}H_{26}ClN_3O$, 347.18; m/z found, 348.2 [M$^+$+H].

E. 1-{4-[6-Chloro-1-(2-morpholin-4-yl-ethyl)-1H-indol-3-yl]-piperidin-1-yl}-3-[5-methanesulfonyl-3-(4-trifluoromethyl-phenyl)-4,5,6,7-tetrahydro-pyrazolo[4,3-c]pyridin-1-yl]-propan-2-ol 6-Chloro-1-(2-morpholin-4-yl-ethyl)-3-piperidin-4-yl-1H-indole (209 mg, 0.6 mmol) and 5-methanesulfonyl-1-oxiranylmethyl-3-(4-trifluoromethyl-phenyl)-4,5,6,7-tetrahydro-1H-pyrazolo[4,3-c]pyridine (120 mg, 0.3 mmol) were set stirring in EtOH (20 mL) containing Et$_3$N (84 µL, 0.6 mmol) at 80° C. After 16 h the mixture was cooled, evaporated, brought up in CH$_2$Cl$_2$ and washed with water. The organics were dried over $Na_2SO_4$ and concentrated. Column chromatography (silica, 0–10% MeOH/CH$_2$Cl$_2$) provided 180 mg (85%) of a white solid. TLC (silica, 10% MeOH/CH$_2$Cl$_2$): $R_f$=0.54. MS (electrospray): exact mass calculated for $C_{36}H_{44}ClF_3N_6O_4S$, 748.28; m/z found, 749.3 [M$^+$+H]. $^1$H NMR (CDCl$_3$, 400 MHz): 7.70 (d, J=8.61 Hz, 2H), 7.64 (d, J=8.261 Hz, 2H), 7.47 (d, J=8.80 Hz, 1H), 7.29 (d, J=1.96, 1H), 7.02 (dd, J=6.46 Hz, 1.76 Hz, 1H), 6.81 (br s, 1H), 4.54 (dd, J=4.09 Hz, 7.43 Hz, 2H), 4.24–4.14 (m, 2H), 4.14–4.08 (m, 2H), 4.06–3.98 (m, 1H), 3.73–3.57 (m, 5H), 3.12–3.0 (m, 2H), 2.97–2.87 (m, 2H), 2.86 (s, 3H), 2.83–2.74 (m, 1H), 2.70–2.64 (t, J=7.24 Hz, 2H), 2.54–2.42 (m, 8H), 2.23–2.14 (m, 1H), 2.05–1.96 (m, 1H), 1.82–1.60 (m, 2H).

Example 5

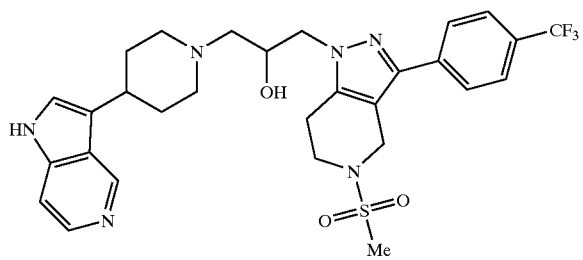

1-[5-Methanesulfonyl-3-(4-trifluoromethyl-phenyl)-4,5,6,7-tetrahydro-pyrazolo[4,3-c]pyridin-1-yl]-3-[4-(1H-pyrrolo[3,2-c]pyridin-3-yl)-piperidin-1-yl]-propan-2-ol A. 4-(1H-Pyrrolo[3,2-c]pyridin-3-yl)-3,6-dihydro-2H-pyridine-1-carboxylic acid tert-butyl ester A solution of 1.9 g (8.47 mmol) of 1H-pyrrolo[3,2-c]pyridine (synthesized following the procedure described in Synthesis, 1996, 882), 4-oxo-piperidine-1-carboxylic acid tert-butyl ester (3.4 g, 16.9 mmol) and potassium hydroxide (1.9 g, 33.9 mmol) in MeOH (20 mL) was heated to reflux for 16 h. The reaction mixture was then cooled to room temperature and poured into ice water (100 mL). The mixture was extracted with 10% MeOH/CH$_2$Cl$_2$ (5×50 mL). The organic extracts was dried over $Na_2SO_4$ and concentrated to form a solid. The solid was washed with MeOH (50 mL), filtered and dried to give a light yellow solid 2.0 g (79%). TLC (silica, 10% MeOH/CH$_2$Cl$_2$): $R_f$=0.5. MS (electrospray): exact mass calculated for $C_{17}H_{21}N_3O_2$, 299.16; m/z found, 300.1 [M$^+$+H]. $^1$H NMR (CDCl$_3$, 400 MHz): 12.26 (br s, 1H), 9.20 (s, 1H), 8.28 (d, J=5.67 Hz, 1H), 7.35 (dd, J=5.09 Hz, 0.78 Hz, 1H), 7.32 (s, 1H), 6.19 (br s, 1H), 4.14 (br s, 2H), 3.68 (t, J=5.67 Hz, 2H), 2.61–2.55 (m, 2H), 1.48 (s, 9H).

B. 4-(1H-Pyrrolo[3,2-c]pyridin-3-yl)-piperidine-1-carboxylic acid tert-butyl ester 4-(1H-Pyrrolo[3,2-c]pyridin-3-yl)-3,6-dihydro-2H-pyridine-1-carboxylic acid tert-butyl ester (2 g, 6.6 mmol) in EtOH (50 mL) containing PtO$_2$ (500 mg) was placed on a Parr hydrogenator at 60 psi H$_2$. After 18 h the mixture was filtered through celite and evaporated to give a white solid (2.0 g, 100%). TLC (silica, 10% MeOH/CH$_2$Cl$_2$): $R_f$=0.49. MS (electrospray): exact mass calculated for $C_{17}H_{23}N_3O_{22}$, 301.18; m/z found, 302.2 [M$^+$+H]. $^1$H NMR (CDCl$_3$, 400 MHz): 13.66 (br s, 1H), 8.88 (s, 1H), 8.79 (d, J=6.46 Hz, 1H), 7.69 (d, J=6.46 Hz, 1H), 7.30 (s, 1H), 4.14 (br s, 2H), 2.99–2.87 (m, 1H), 2.86–2.71 (m, 2H), 1.91 (d, J=11.54 Hz, 2H), 1.64–1.50 (m, 2H), 1.38 (s, 9H).

C. 3-Piperidin-4-yl-1H-pyrrolo[3,2-c]pyridine 4-(1H-Pyrrolo[3,2-c]pyridin-3-yl)-piperidine-1-carboxylic acid tert-butyl ester (2.0 g, 6.6 mmol) was set stirring in 1:1 TFA/CH$_2$Cl$_2$. After 45 min the mixture was evaporated and the golden oil brought up in Et$_2$O. A solid formed and was filtered, washed with Et$_2$O and air dried to give 2.1 g (100%) of a white solid as a TFA salt. MS (electrospray): exact mass calculated for $C_{12}H_{15}N_3$, 201.13; m/z found, 202.1 [M$^+$+H]. $^1$H NMR (CDCl$_3$, 400 MHz): 9.4 (br s, 1H), 8.96 (s, 1H), 8.26 (d, J=5.87 Hz, 1H), 7.24 (s, 1H), 6.99 (s, 1H), 3.22–3.16 (m, 2H), 3.05–2.95 (m, 1H), 2.86–2.77 (m, 2H), 2.05 (d, J=12.72 Hz, 2H), 1.89 (br s, 1H), 1.75–1.63 (m, 2H).

D. 1-[5-Methanesulfonyl-3-(4-trifluoromethyl-phenyl)-4,5,6,7-tetrahydro-pyrazolo[4,3-c]pyridin-1-yl]-3-[4-(1H-pyrrolo[3,2-c]pyridin-3-yl)-piperidin-1-yl]-propan-2-ol 3-Piperidin-4-yl-1H-pyrrolo[3,2-c]pyridine (159 mg, 0.5 mmol) and 5-methanesulfonyl-1-oxiranylmethyl-3-(4-trifluoromethyl-phenyl)-4,5,6,7-tetrahydro-1H-pyrazolo[4,3-c]pyridine (200 mg, 0.5 mmol) were set stirring in EtOH (10 mL) containing Et$_3$N (112 μL, 0.77 mmol) at 80° C. After 16 h the mixture was cooled, evaporated, brought up in CH$_2$Cl$_2$ and washed with water. The organics were dried over Na$_2$SO$_4$ and concentrated. Column chromatography (silica, 0–10% (2 N NH$_3$ in MeOH)/CH$_2$Cl$_2$) provided 82 mg (27%) of a white solid. TLC (silica, 10% MeOH/CH$_2$Cl$_2$): R$_f$=0.8. MS (electrospray): exact mass calculated for C$_{29}$H$_{33}$F$_3$N$_6$O$_3$S, 602.23; m/z found, 603.2 [M$^+$+H]. $^1$H NMR (CDCl$_3$, 400 MHz): 9.62 (s, 1H), 8.90 (s, 1H), 8.21 (d, J=5.87 Hz, 1H), 7.69 (d, J=7.83 Hz, 2H), 7.62 (d, J=8.41 Hz, 2H), 7.23 (d, J=5.87, 1H), 6.97 (s, 1H), 4.51 (dd, J=14.48 Hz, 8.80 Hz, 2H), 4.23–4.13 (m, 2H), 4.05–3.95 (m, 1H), 3.72–3.54 (m, 3H), 3.11–2.98 (m, 2H), 2.95–2.86 (m, 2H), 2.84 (s, 3H), 2.51–2.39 (m, 3H), 2.20–2.11 (m, 1H), 2.07–1.97 (m, 2H), 1.85–1.63 (m, 2H).

Example 6

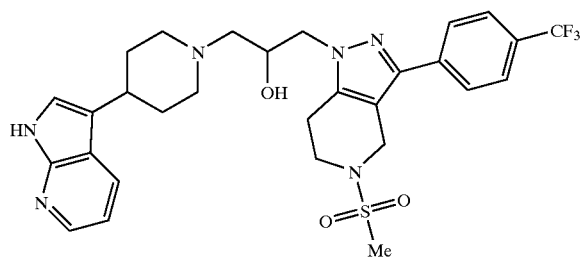

1-[5-Methanesulfonyl-3-(4-trifluoromethyl-phenyl)-4,5,6,7-tetrahydro-pyrazolo[4,3-c]pyridin-1-yl]-3-[4-(1H-pyrrolo[2,3-b]pyridin-3-yl)-piperidin-1-yl]-propan-2-ol A. 4-(1H-Pyrrolo[2,3-b]pyridin-3-yl)-3,6-dihydro-2H-pyridine-1-carboxylic acid tert-butyl ester 1H-Pyrrolo[2,3-b]pyridine (3 g, 25 mmol), 4-oxo-piperidine-1-carboxylic acid tert-butyl ester (4.2 g, 21 mmol) and potassium hydroxide (3.56 g, 63 mmol) were added in MeOH (60 mL) and heated to reflux for 16 h. The reaction mixture was then cooled to room temperature and poured into ice water (300 mL). The mixture was extracted with 10% MeOH/CH$_2$Cl$_2$ (5×150 mL). The organic extracts was dried over Na$_2$SO$_4$ and concentrated to form a solid. The solid was washed with MeOH (150 mL), filtered and dried to give a light yellow solid 5.7 g (91%). TLC (silica, 50% EtOAc/hexanes): R$_f$=0.3. MS (electrospray): exact mass calculated for C$_{17}$H$_{21}$N$_3$O$_2$, 299.16; m/z found, 300.2 [M$^+$+H]. $^1$H NMR (CDCl$_3$, 400 MHz) 10.97 (br s, 1H), 8.33 (dd, J=3.33 Hz, 1.37 Hz, 1H), 8.20 (dd, J=6.65 Hz, 1.37 Hz, 1H), 7.34 (br s, 1H), 7.25 (s, 1H), 7.13 (dd, J=4.89 Hz, 3.13 Hz, 1H), 4.14 (br s, 2H), 3.68 (t, J=5.28 Hz, 2H), 2.56 (br s, 2H), 1.49 (s, 9H).

B. 4-(1H-Pyrrolo[2,3-b]pyridin-3-yl)-piperidine-1-carboxylic acid tert-butyl ester 4-(1H-Pyrrolo[2,3-b]pyridin-3-yl)-3,6-dihydro-2H-pyridine-1-carboxylic acid tert-butyl ester (1 g, 3.3 mmol) in EtOH (25 mL) containing PtO$_2$ (250 mg) was placed on a Parr hydrogenator at 60 psi H$_2$. After 18 h the mixture was filtered through celite and evaporated to give 0.96 g (97%) of a white solid. TLC (silica, 50% EtOAc/hexanes): R$_f$=0.5.

MS (electrospray): exact mass calculated for C$_{17}$H$_{23}$N$_3$O$_{22}$, 301.18; m/z found, 302.2 [M$^+$+H]. $^1$H NMR (CDCl$_3$, 400 MHz) 10.95 (br s, 1H), 8.26 (dd, J=3.33 Hz, 1.37 Hz, 1H), 7.96 (dd, J=6.26 Hz, 1.57 Hz, 1H), 7.11 (s, 1H), 7.05 (dd, J=4.89 Hz, 3.13 Hz, 1H), 4.22 (br s, 2H), 3.00–2.79 (m, 3H), 1.99 (d, J=13.89 Hz, 2H), 1.74–1.60 (m, 2H), 1.47 (s, 9H).

C. 3-Piperidin-4-yl-1H-pyrrolo[2,3-b]pyridine 4-(1H-Pyrrolo[2,3-b]pyridin-3-yl)-piperidine-1-carboxylic acid tert-butyl ester (963 mg, 3.2 mmol) was set stirring in 1:1 TFA/CH$_2$Cl$_2$. After 45 min the mixture was evaporated and the golden oil brought up in Et$_2$O. A solid formed and was filtered, washed with Et$_2$O and air dried to give 974 mg (96%) of a white solid as a TFA salt. MS (electrospray): exact mass calculated for C$_{12}$H$_{15}$N$_3$, 201.13; m/z found, 202.1 [M$^+$+H]. $^1$H NMR (CDCl$_3$, 400 MHz): 8.09 (dd, J=3.33 Hz, 1.57 Hz, 1H), 7.89 (dd, J=6.26 Hz, 1.57 Hz, 1H), 7.01 (s, 1H), 6.99 (dd, J=4.89 Hz, 3.13 Hz, 1H), 5.04 (br s, 2H), 3.11–3.04 (m, 2H), 2.88–2.79 (m, 1H), 2.73–2.64 (m, 2H), 1.94 (d, J=12.52 Hz, 2H), 1.65–1.63 (m, 2H).

D. 1-[5-Methanesulfonyl-3-(4-trifluoromethyl-phenyl)-4,5,6,7-tetrahydro-pyrazolo[4,3-c]pyridin-1-yl]-3-[4-(1H-pyrrolo[2,3-b]pyridin-3-yl)-piperidin-1-yl]-propan-2-ol 3-Piperidin-4-yl-1H-pyrrolo[2,3-b]pyridine (443 mg, 1.4 mmol) and 5-methanesulfonyl-1-oxiranylmethyl-3-(4-trifluoromethyl-phenyl)-4,5,6,7-tetrahydro-1H-pyrazolo[4,3-c]pyridine (289 mg, 0.7 mmol) were set stirring in EtOH (10 mL) containing Et$_3$N (146 μL, mmol) at 80° C. After 16 h the mixture was cooled, evaporated, brought up in CH$_2$Cl$_2$ and washed with water. The organics were dried over Na$_2$SO$_4$ and concentrated. Column chromatography (silica, 0–10% (2 N NH$_3$ in MeOH)/CH$_2$Cl$_2$) provided 107 mg (25%) of a white solid. TLC (silica, 10% MeOH/CH$_2$Cl$_2$): R$_f$=0.45. MS (electrospray): exact mass calculated for C$_{29}$H$_{33}$F$_3$N$_6$O$_3$S, 602.23; m/z found, 603.3 [M$^+$+H]. $^1$H NMR (CDCl$_3$, 400 MHz): 10.6 (br s, 1H), 8.24 (m, 1H), 7.91 (m, 1H), 7.70 (m, 2H), 7.63 (m, 2H), 7.05 (br s, 1H), 7.02 (m, 1H), 4.52 (dd, J=4.28 Hz, 9.78 Hz, 2H), 4.24–4.16 (m, 2H), 4.06–3.98 (m, 1H), 3.72–3.64 (m, 1H), 3.64–3.55 (m, 1H), 3.11–3.00 (m, 2H), 2.96–2.87 (m, 2H), 2.85 (s, 3H), 2.82–2.74 (m, 1H), 2.53–2.40 (m, 3H), 2.22–2.12 (m, 1H), 2.05–1.95 (m, 2H), 1.85–1.64 (m, 2H).

Example 7

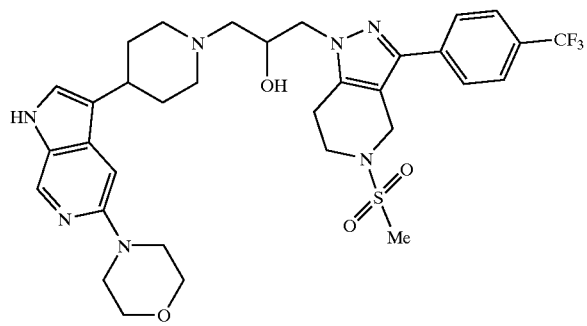

1-[5-Methanesulfonyl-3-(4-trifluoromethyl-phenyl)-4,5,6,7-tetrahydro-pyrazolo[4,3-c]pyridin-1-yl]-3-[4-(5-morpholin-4-yl-1H-pyrrolo[2,3-c]pyridin-3-yl)-piperidin-1-yl]-propan-2-ol A. [2-(2-Chloro-5-nitro-pyridin-4-yl)-vinyl]-dimethyl-amine A solution of 2-chloro-4-methyl-5-nitro-pyridine (2 g, 11.59 mmol) in DMF (11.6 mL) was treated with 3.08 mL (23.2 mmol, 2 eq) of DMF-dimethylacetal and the reaction mixture was stirred at 100° C. for 4 h. All volatiles were removed under reduced pressure. Column chromatography (silica, 20% EtOAc/hexanes) provided 2.37 g (90%) of [2-(2-chloro-5-nitro-pyridin-4-yl)-vinyl]-dimethyl-amine. TLC (silica, 20% EtOAc/hexanes): $R_f$=0.30. MS (electrospray): exact mass calculated for $C_9H_{10}ClN_3O_2$, 227.05; m/z found, 228.1 $[M+H]^+$. $^1$H NMR (400 MHz, $CDCl_3$): 8.79 (s, 1H), 8.02 (s, 1H), 7.35 (d, J=13 Hz, 1H), 5.94 (d, J=13 Hz, 1H), 2.96 (s, 3H), 2.87 (s, 3H).

B. 5-Morpholin-4-yl-1H-pyrrolo[2,3-c]pyridine

A solution of 450 mg (2 mmol) of [2-(2-chloro-5-nitro-pyridin-4-yl)-vinyl]-dimethyl-amine in a 20 mL of mixed solvent of MeOH-$CH_2Cl_2$ (1:1) was treated with 3 mL of morpholine. The reaction mixture was stirred at 65° C. for 8 h. Volatiles were then removed. $CH_2Cl_2$ (100 mL) and $H_2O$ (30 mL) were added. The organic layer was separated and washed with $H_2O$ (30 mL), brine (30 mL), dried over $Na_2SO_4$, and concentrated. The red powder was treated with 4.0 g (63 mmol, 32 eq) of ammonium formate and 10% Pd—C (120 mg). The reaction mixture was stirred at 65° C. for 30 min. The reaction mixture was then filtered through a pad of celite and concentrated to obtain a yellow solid. Column chromatography (silica, 5% MeOH/$CH_2Cl_2$) provided 210 mg (52% for 2 steps) of 5-morpholin-4-yl-1H-pyrrolo[2,3-c]pyridine as a yellow solid. TLC (silica, 5% MeOH/$CH_2Cl_2$): $R_f$=0.40. MS (electrospray): exact mass calculated for $C_{11}H_{13}N_3O$, 203.11; m/z found, 204.2 $[M+H]^+$.

C. 4-(5-Morpholin-4-yl-1H-pyrrolo[2,3-c]pyridin-3-yl)-piperidine-1-carboxylic acid tert-butyl ester A solution of 200 mg (1.0 mmol) of 5-morpholin-4-yl-1H-pyrrolo[2,3-c]pyridine and 398 mg (2.0 mmol, 2 eq) of 4-oxo-piperidine-1-carboxylic acid tert-butyl ester in 5 mL of MeOH was treated with 224 mg (4.0 mmol, 4 eq) of potassium hydroxide. The reaction mixture was stirred at 65° C. for 12 h and volatiles were removed. The crude product was partitioned between $CH_2Cl_2$ (100 mL) and 20 mL of $H_2O$. The organic layer was washed with $H_2O$ (2×20 mL), dried over $Na_2SO_4$ and concentrated. The yellow powder was treated with 630 mg (10 mmol, 10 eq) of ammonium formate and 10% Pd—C (50 mg). The reaction mixture was stirred at 65° C. for 1 h. The reaction mixture was then filtered through a pad of celite and concentrated to obtain a yellow solid. Column chromatography (silica, 5% MeOH/$CH_2Cl_2$) provided 180 mg (47% for 2 steps) of a yellow solid. TLC (silica, 5% MeOH/$CH_2Cl_2$): $R_f$=0.40. MS (electrospray): exact mass calculated for $C_{21}H_{30}N_4O_3$, 386.23; m/z found, 387.2 $[M+H]^+$.

D. 1-[5-Methanesulfonyl-3-(4-trifluoromethyl-phenyl)-4,5, 6,7-tetrahydropyrazolo[4,3-c]pyridin-1-yl]-3-[4-(5-morpholin-4-yl-1H-pyrrolo[2,3-c]pyridin-3-yl)-piperidin-1-yl]-propan-2-ol 4-(5-Morpholin-4-yl-1H-pyrrolo[2,3-c]pyridin-3-yl)-piperidine-1-carboxylic acid tert-butyl ester (180 mg, 0.47 mmol) was dissolved in 3.0 mL of $CH_2Cl_2$ and treated with 2.5 mL of trifluoroacetic acid. The reaction mixture was stirred at 25° C. for 1 h before all volatiles were removed. The solid was dissolved in MeOH (20 mL) and neutralized with DOWEX 550A OH anion exchange resin to pH 8. The resin was then filtered off and MeOH was removed under reduced pressure. The residue was dissolved in 2.5 mL of $^i$PrOH and treated with 187 mg (0.47 mmol, 1 eq) of 5-methanesulfonyl-1-oxiranylmethyl-3-(4-trifluoromethyl-phenyl)-4,5,6,7-tetrahydro-1H-pyrazolo[4,3-c]pyridine. The reaction was stirred at 85° C. for 3 h before solvent was removed. Column chromatography (silica, 5–10% MeOH/$CH_2Cl_2$ then 5–10% (2 N $NH_3$ in MeOH)/$CH_2Cl_2$) provided 97 mg (30%) of the title compound. TLC (silica, 5% MeOH/$CH_2Cl_2$): $R_f$=0.25. MS (electrospray): exact mass calculated for $C_{33}H_{40}F_3N_7O_4S$, 687.28; m/z found, 688.3 $[M+H]^+$. $^1$H NMR (400 MHz, $CDCl_3$): 8.47 (br s, 1H), 8.44 (d, J=1.0 Hz, 1H), 7.70 and 7.65 (AB pattern, J=8.4 Hz, 4H), 7.03 (d, J=2.1 Hz, 1H), 6.76 (s,1H), 4.58–4.50 (m, 2H), 4.21–4.00 (m, 3H), 3.90 (t, J=4.5 Hz, 4H), 3.72–3.58 (m, 2H), 3.40 (t, J=4.5 Hz, 4H), 3.10–2.85 (m, 4H), 2.88 (s, 3H), 2.80–2.70 (m, 1H), 2.52–2.41 (m, 3H), 2.20–2.00 (m, 3H), 1.80–1.60 (m, 2H).

Example 8

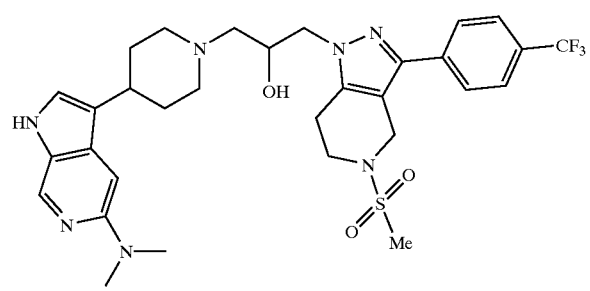

1-[4-(6-Dimethylamino-1H-pyrrolo[3,2-c]pyridin-3-yl)-piperidin-1-yl]-3-[5-methanesulfonyl-3-(4-trifluoromethyl-phenyl)-4,5,6,7-tetrahydro-pyrazolo[4,3-c]pyridin-1-yl]-propan-2-ol A. Dimethyl-(5-methyl-4-nitro-1-oxy-pyridin-2-yl)-amine A solution of 2-bromo-5-methyl-4-nitro-pyridine 1-oxide (674 mg, 2.78 mmol) in 2 M dimethylamine in methanol (20 mL) was heated at 65° C. for 16 h. The solvent was evaporated under reduced pressure. The residue was purified by column chromatography (silica, 30–80% EtOAc/hexanes) to obtain 290 mg (53%) of the desired product. TLC (silica, 50% EtOAc/hexanes): $R_f$=0.10. MS (electrospray): exact mass calculated for $C_8H_{11}N_3O_3$, 197.08; m/z found, 198.1 $[M^++H]$. $^1$H NMR ($CDCl_3$, 400 MHz): 8.04 (s, 1H), 7.50 (s, 1H), 3.00 (s, 6H), 2.44 (s, 3H).

B. Dimethyl-(1H-pyrrolo[3,2-c]pyridin-6-yl)-amine

A solution of dimethyl-(5-methyl-4-nitro-1-oxy-pyridin-2-yl)-amine (290 mg, 1.47 mmol) in DMF (3 mL) was treated with DMF-dimethylacetal (390 µL, 2.94 mmol) and the reaction mixture was stirred at 100° C. for 4 h. All volatiles were removed under reduced pressure. The red powder was treated with ammonium formate (927 mg, 14.7 mmol) and 10% Pd—C (156 mg). The reaction mixture was stirred at 65° C. for 30 min. The reaction mixture was then filtered through a pad of celite and concentrated to obtain a yellow solid. Column chromatography (silica, 5% MeOH/$CH_2Cl_2$) provided 100 mg (42% for two steps) of product as a yellow solid. TLC (silica, 10% MeOH/$CH_2Cl_2$): $R_f$=0.2. MS (electrospray): exact mass calculated for $C_9H_{11}N_3$, 161.10; m/z found, 162.1 $[M^++H]$. $^1$H NMR ($CDCl_3$, 400 MHz): 8.55 (s, 1H), 8.28 (br s, 1H), 6.96 (dd, J=1.96 Hz, 1.37 Hz, 1H), 6.45–6.43 (m, 1H), 6.39 (s, 1H), 3.08 (s, 6H).

C. 4-(6-Dimethylamino-1H-pyrrolo[3,2-c]pyridin-3-yl)-3,6-dihydro-2H-pyridine-1-carboxylic acid tert-butyl ester Dimethyl-(1H-pyrrolo[3,2-c]pyridin-6-yl)-amine (100 mg, 0.62 mmol), 4-oxo-piperidine-1-carboxylic acid tert-butyl ester (248 mg, 1.24 mmol) and potassium hydroxide (139 mg, 2.48 mmol) were added in MeOH (5 mL) and heated to reflux for 16 h. The reaction mixture was then cooled to room temperature and poured into ice water (20 mL). The mixture was extracted with 10% MeOH/CH$_2$Cl$_2$ (5×10 mL). The organic extracts was dried over Na$_2$SO$_4$ and concentrated. The residue was purified by column chromatography (silica, 0–5% MeOH/CH$_2$Cl$_2$) to obtain 180 mg (85%) of the title compound. TLC (silica, 10% MeOH/CH$_2$Cl$_2$): R$_f$=0.58. MS (electrospray): exact mass calculated for C$_{19}$H$_{26}$N$_4$O$_2$, 342.21; m/z found, 343.2 (M$^+$+H). $^1$H NMR (CDCl$_3$, 400 MHz): 9.09 (br s, 1H), 8.76 (s, 1H), 6.90 (d, J=2.15 Hz, 1H), 6.32 (s, 1H), 6.10 (br s, 1H), 4.10–4.05 (m, 2H), 3.62 (t, J=5.87 Hz, 2H), 3.03 (s, 6H), 2.52–2.44 (m, 2H), 1.46 (s, 9H).

D. 4-(6-Dimethylamino-1H-pyrrolo[3,2-c]pyridin-3-yl)-piperidine-1-carboxylic acid tert-butyl ester A solution of 4-(6-dimethylamino-1H-pyrrolo[3,2-c]pyridin-3-yl)-3,6-dihydro-2H-pyridine-1-carboxylic acid tert-butyl ester (180 mg, 0.53 mmol) in MeOH (10 mL) was treated with ammonium formate (332 mg, 5.3 mmol) and 10% Pd—C (56 mg). The reaction mixture was stirred at 65° C. for 1 h. The reaction mixture was then filtered through a pad of celite and concentrated to obtain an off white solid. Column chromatography (silica, 0–5% MeOH/CH$_2$Cl$_2$) provided 135 mg (75%) of product as a white solid. TLC (silica, 10% MeOH/CH$_2$Cl$_2$): R$_f$=0.50. MS (electrospray): exact mass calculated for C$_{19}$H$_{28}$N$_4$O$_2$, 344.22; m/z found, 345.2 [M$^+$+H]. $^1$H NMR (CDCl$_3$, 400 MHz): 8.53 (s, 1H), 8.30 (br s, 1H), 6.67 (dd, J=1.17 Hz, 0.78 Hz, 1H), 6.34 (d, J=0.78 Hz, 1H), 4.33–4.16 (m, 2H), 3.05 (s, 6H), 2.97–2.80 (m, 3H), 1.99 (d, J=12.72 Hz, 2H), 1.69–1.53 (m, 2H), 1.46 (s, 9H).

E. Dimethyl-(3-piperidin-4-yl-1H-pyrrolo[3,2-c]pyridin-6-yl)-amine

The 4-(6-dimethylamino-1H-pyrrolo[3,2-c]pyridin-3-yl)-piperidine-1-carboxylic acid tert-butyl ester (135 mg, 0.39 mmol) was set stirring in 1:1 TFA/CH$_2$Cl$_2$. After 45 min the mixture was evaporated. The residue was dissolved in MeOH (10 mL) and neutralized with DOWEX 550A OH anion exchange resin to pH 8. The resin was then filtered off and MeOH was removed under reduced pressure to give 96 mg (100%) of a yellow solid. MS (electrospray): exact mass calculated for C$_{14}$H$_{20}$N$_4$, 244.17; m/z found, 245.2 [M$^+$+H]. $^1$H NMR (CDCl$_3$, 400 MHz): 9.23 (br s, 1H), 8.54 (s, 1H), 6.67 (s, 1H), 6.31 (d, J=0.98 Hz, 1H), 3.15 (d, J=2.13 Hz, 2H), 3.02 (s, 6H), 2.91–2.81 (m, 1H), 2.81–2.72 (m, 2H), 2.01 (d, J=12.52 Hz, 2H), 1.69–1.52 (m, 2H).

F. 1-[4-(6-Dimethylamino-1H-pyrrolo[3,2-c]pyridin-3-yl)-piperidin-1-yl]-3-[5-methanesulfonyl-3-(4-trifluoromethyl-phenyl)-4,5,6,7-tetrahydro-pyrazolo[4,3-c]pyridin-1-yl]-propan-2-ol Dimethyl-(3-piperidin-4-yl-1H-pyrrolo[3,2-c]pyridin-6-yl)-amine (96 mg, 0.53 mmol) and 5-methanesulfonyl-1-oxiranylmethyl-3-(4-trifluoromethyl-phenyl)-4,5,6,7-tetrahydro-1H-pyrazolo[4,3-c]pyridine (319 mg, 0.80 mmol) were set stirring in $^i$PrOH (10 mL) at 80° C. After 16 h the mixture was cooled and concentrated. The residue was purified by column chromatography (silica, 0–10% (2 N NH$_3$ in MeOH)/CH$_2$Cl$_2$ to obtain 61 mg (18%) of a white solid. TLC (silica, 10% MeOH/CH$_2$Cl$_2$): R$_f$=0.12. MS (electrospray): exact mass calculated for C$_{31}$H$_{38}$F$_3$N$_7$O$_3$S, 645.27; m/z found, 646.3 [M$^+$+H]. $^1$H NMR (CDCl$_3$, 400 MHz): 8.53 (s, 1H), 7.93 (br s, 1H), 7.71 (d, J=8.22 Hz, 2H), 7.64 (d, J=8.22 Hz, 2H), 6.67 (br s, 1H), 6.33 (d, J=0.98 Hz, 1H), 4.54 (dd, J=14.28 Hz, 9.59 Hz, 2H), 4.22–4.10 (m, 2H), 4.04–3.97 (m, 1H), 3.74–3.57 (m, 2H), 3.13–3.06 (m, 1H), 3.05 (s, 6H), 3.03–2.87 (m, 3H), 2.85 (s, 3H), 2.82–2.71 (m, 1H), 2.50–2.37 (m, 3H), 2.20–2.11 (m, 1H), 2.06–1.97 (m, 2H), 1.82–1.61 (m, 2H).

Example 9

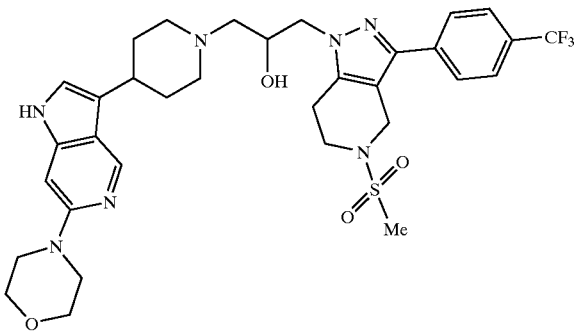

1-[5-Methanesulfonyl-3-(4-trifluoromethyl-phenyl)-4,5,6,7-tetrahydro-pyrazolo[4,3-c]pyridin-1-yl]-3-[4-(6-morpholin-4-yl-1H-pyrrolo[3,2-c]pyridin-3-yl)-piperidin-1-yl]-propan-2-ol A. 4-(5-Methyl-4-nitro-1-oxy-pyridin-2-yl)-morpholine A solution of 2-bromo-5-methyl-4-nitro-pyridine 1-oxide (500 mg, 2.14 mmol) in morpholine (15 mL) was heated at 70° C. for 16 h. The solvent was evaporated under reduced pressure. The residue was purified by column chromatography (silica, 30–80% EtOAc/hexanes) to obtain 480 mg (94%) of the desired product. TLC (silica, 50% EtOAc/hexanes): R$_f$=0.10. MS (electrospray): exact mass calculated for C$_{10}$H$_{13}$N$_3$O$_4$, 239.09; m/z found, 240.1 [M$^+$+H]. $^1$H NMR (CDCl$_3$, 400 MHz): 8.09 (s, 1H), 7.55 (s, 1H), 3.90 (t, J=4.50 Hz, 4H), 3.36 (t, J=4.70 Hz, 4H), 2.50 (s, 3H).

B. 6-Morpholin-4-yl-1H-pyrrolo[3,2-c]pyridine

A solution of 4-(5-methyl-4-nitro-1-oxy-pyridin-2-yl)-morpholine (480 mg, 2 mmol) in DMF (5 mL) was treated with DMF-dimethylacetal (533 μL, 4 mmol) and the reaction mixture was stirred at 100° C. for 4 h. All volatiles were removed under reduced pressure. The red powder was treated with ammonium formate (1.26 g, 20 mmol) and 10% Pd—C (212 mg). The reaction mixture was stirred at 65° C. for 30 min. The reaction mixture was then filtered through a pad of celite and concentrated to obtain a yellow solid. Column chromatography (silica, 5% MeOH/CH$_2$Cl$_2$) provided 197 mg (49% for two steps) of a yellow solid. TLC (silica, 10% MeOH/CH$_2$Cl$_2$): R$_f$=0.55. MS (electrospray): exact mass calculated for C$_{11}$H$_{13}$N$_3$O, 203.11; m/z found, 204.1 [M+H]$^+$. $^1$H NMR (CDCl$_3$, 400 MHz) 8.68 (br s, 1H), 8.59 (s, 1H), 7.04 (dd, J=2.15 Hz, 1.17 Hz, 1H), 6.51 (s, 1H), 6.49–6.47 (m, 1H), 3.86 (t, J=4.70 Hz, 4H), 3.40 (t, J=4.70 Hz, 4H).

C. 4-(6-Morpholin-4-yl-1H-pyrrolo[3,2-c]pyridin-3-yl)-3,6-dihydro-2H-pyridine-1-carboxylic acid tert-butyl ester 6-Morpholin-4-yl-1H-pyrrolo[3,2-c]pyridine (197 mg, 0.97 mmol), 4-oxo-piperidine-1-carboxylic acid tert-butyl ester (387 mg, 1.94 mmol) and potassium hydroxide (218 mg, 3.88 mmol) were added in MeOH (10 mL) and heated to reflux for 16 h. The reaction mixture was then cooled to room temperature and poured into ice water (50 mL). The mixture was extracted with 10% MeOH/CH$_2$Cl$_2$ (5×20 mL). The organic extracts was dried over Na$_2$SO$_4$ and concentrated. The residue was purified by column chromatography (silica, 0–5% MeOH/CH$_2$Cl$_2$) to obtain 337 mg (91%) of the desired product. TLC (silica, 5% MeOH/CH$_2$Cl$_2$): R$_f$=0.50. MS (electrospray): exact mass calculated for C$_{21}$H$_{28}$N$_4$O$_3$, 384.22; m/z found, 749.3 [M$^+$+H]. $^1$H NMR (CDCl$_3$, 400 MHz): 9.24 (brs, 1H), 8.77 (s, 1H), 6.95 (d, J=2.15 Hz, 1H), 6.45 (s, 1H), 6.09 (brs, 1H), 4.09–4.04 (m, 2H), 3.66 (t, J=6.06 Hz, 4H), 3.60 (t, J=5.28 Hz, 2H), 3.25 (t, J==5.09 Hz, 4H), 2.38 (d, J=6.26 Hz, 2H), 1.44 (s, 9H).

D. 4-(6-Morpholin-4-yl-1H-pyrrolo[3,2-c]pyridin-3-yl)-piperidine-1-carboxylic acid tert-butyl ester 4-(6-Morpholin-4-yl-1H-pyrrolo[3,2-c]pyridin-3-yl)-3,6-dihydro-2H-pyridine-1-carboxylic acid tert-butyl ester (337 mg, 0.9 mmol) in MeOH (20 mL) was treated with ammonium formate (568 mg, 9.0 mmol) and 10% Pd—C (95 mg). The reaction mixture was stirred at 65° C. for 1 h. The reaction mixture was then filtered through a pad of celite and concentrated to obtain an off-white solid. Column chromatography (silica, 0–5% MeOH/CH$_2$Cl$_2$) provided 340 mg (98%) of a white solid. TLC (silica, 5% MeOH/CH$_2$Cl$_2$): R$_f$=0.40. MS (electrospray): exact mass calculated for C$_{21}$H$_{30}$N$_4$O$_3$, 386.23; m/z found, 387.3 [M$^+$+H]. $^1$H NMR (CDCl$_3$, 400 MHz) 9.14 (br s, 1H), 8.55 (s, 1H), 6.74 (d, J=1.96 Hz, 1H), 6.45 (s, 1H), 4.27–4.08 (m, 2H), 3.80 (t, J=4.50 Hz, 4H), 3.34 (t, J=4.89 Hz, 4H), 2.96–2.77 (m, 3H), 1.97 (d, J=12.91 Hz, 2H), 1.67–1.52 (m, 2H), 1.44 (s, 9H).

E. 6-Morpholin-4-yl-3-piperidin-4-yl-1H-pyrrolo[3,2-c]pyridine 4-(6-Morpholin-4-yl-1H-pyrrolo[3,2-c]pyridin-3-yl)-piperidine-1-carboxylic acid tert-butyl ester (380 mg, 0.98 mmol) was set stirring in 1:1 TFA/CH$_2$Cl$_2$. After 45 min the mixture was evaporated. The residue was dissolved in MeOH (20 mL) and neutralized with DOWEX 550A OH anion exchange resin to pH 8. The resin was then filtered off and MeOH was removed under reduced pressure to give 281 mg (100%) of a yellow solid. MS (electrospray): exact mass calculated for C$_{16}$H$_{22}$N$_4$O, 286.18; m/z found, 287.1 [M$^+$+H].

F. 1-[5-Methanesulfonyl-3-(4-trifluoromethyl-phenyl)-4,5,6,7-tetrahydro-pyrazolo[4,3-c]pyridin-1-yl]-3-[4-(6-morpholin-4-yl-1H-pyrrolo[3,2-c]pyridin-3- piperidin-1-yl]-propan-2-ol 6-Morpholin-4-yl-3-piperidin-4-yl-1H-pyrrolo[3,2-c]pyridine (281 mg, 0.98 mmol) and 5-methanesulfonyl-1-oxiranylmethyl-3-(4-trifluoromethyl-phenyl)-4,5,6,7-tetrahydro-1H-pyrazolo[4,3-c]pyridine (591 mg, 1.47 mmol) were set stirring in $^i$PrOH (10 mL) at 80° C. After 16 h the mixture was cooled and concentrated. The residue was purified by column chromatography (silica, 0–10% (2 N NH$_3$ in MeOH)/CH$_2$Cl$_2$) to obtain 468 mg (69%) of a white solid. TLC (silica, 10% (2 N NH$_3$ in MeOH)/CH$_2$Cl$_2$): R$_f$=0.62. MS (electrospray): exact mass calculated for C$_{33}$H$_{40}$F$_3$N$_7$O$_4$S, 687.28; m/z found, 688.3 [M$^+$+H]. $^1$H NMR (CDCl$_3$, 400 MHz): 8.56 (s, 1H), 8.40 (br s, 1H), 7.69 (d, J=8.41 Hz, 2H), 7.63 (d, J=8.41 Hz, 2H), 6.73 (br s, 1H), 6.46 (s, 1H), 4.51 (dd, J=14.28 Hz, 8.80 Hz, 2H), 4.21–4.10 (m, 2H), 4.03–3.95 (m, 1H), 3.82 (t, J=4.11 Hz, 4H), 3.71–3.54 (m, 2H), 3.36 (t, J=4.89 Hz, 4H), 3.10–2.97 (m, 2H), 2.93–2.86 (m, 2H), 2.84 (s, 3H), 2.82–2.72 (m, 1H), 2.50–2.37 (m, 3H), 2.20–2.10 (m, 1H), 2.04–1.95 (m, 2H), 1.80–1.60 (m, 2H).

Example 10

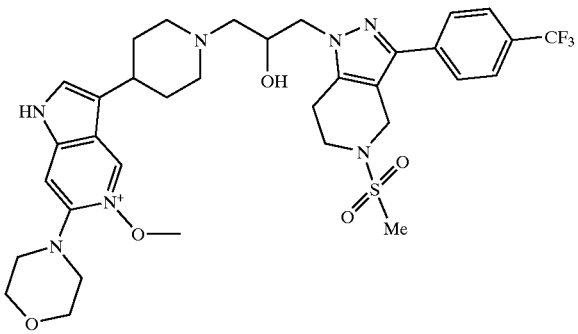

1-[5-Methanesulfonyl-3-(4-trifluoromethyl-phenyl)-4,5,6,7-tetrahydro-pyrazolo[4,3-c]pyridin-1-yl]-3-[4-(6-morpholin-4-yl-5-oxy-1 H-pyrrolo[3,2-c]pyridin-3-yl)-piperidin-1-yl]-propan-2-ol A. 6-Morpholin-4-yl-1H-pyrrolo[3,2-c]pyridine 5-oxide A solution of 4-(5-methyl-4-nitro-1-oxy-pyridin-2-yl)-morpholine (480 mg, 2 mmol) in DMF (5 mL) was treated with DMF-dimethylacetal (533 µL, 4 mmol) and the reaction mixture was stirred at 100° C. for 4 h. All volatiles were removed under reduced pressure. The red powder was treated with ammonium formate (1.26 g, 20 mmol) and 10% Pd—C (212 mg). The reaction mixture was stirred at 65° C. for 30 min. The reaction mixture was then filtered through a pad of celite and concentrated to obtain a yellow solid. Column chromatography (silica, 5% MeOH/CH$_2$Cl$_2$) provided 130 mg (30% for two steps) of a yellow solid. TLC (silica, 10% MeOH/CH$_2$Cl$_2$): R$_f$=0.28. MS (electrospray): exact mass calculated for C$_{11}$H$_{13}$N$_3$O$_2$, 219.10; m/z found, 220.1 [M+H]$^+$. $^1$H NMR (CDCl$_3$, 400 MHz): 8.42 (br s, 1H), 7.25 (s, 1H), 7.14 (s, 1H), 6.82 (s, 1H), 6.35 (s, 1H), 3.79 (t, J=4.70 Hz, 4H), 3.18 (t, J=4.70 Hz, 4H).

B. 4-(6-Morpholin-4-yl-5-oxy-1H-pyrrolo[3,2-c]pyridin-3-yl)-3,6-dihydro-2H-pyridine-1-carboxylic acid tert-butyl ester 6-Morpholin-4-yl-1H-pyrrolo[3,2-c]pyridine 5-oxide (130 mg, 0.59 mmol), 4-oxo-piperidine-1-carboxylic acid tert-butyl ester (237 mg, 1.19 mmol) and potassium hydroxide (133 mg, 2.37 mmol) were added in MeOH (8 mL) and heated to reflux for 16 h. The reaction mixture was then cooled to room temperature and poured into ice water (30 mL). The mixture was extracted with 10% MeOH/CH$_2$Cl$_2$ (5×10 mL). The organic extracts was dried over Na$_2$SO$_4$ and concentrated. The residue was purified by column chromatography (silica, 0–5% MeOH/CH$_2$Cl$_2$) to obtain 140 mg (59%) of the desired product. TLC (silica, 10% MeOH/CH$_2$Cl$_2$): R$_f$=0.55. MS (electrospray): exact mass calculated for C$_{21}$H$_{28}$N$_4$O$_4$, 400.21; m/z found, 401.2 (M$^+$+H).

C. 4-(6-Morpholin-4-yl-5-oxy-1H-pyrrolo[3,2-c]pyridin-3-yl)-piperidine-1-carboxylic acid tert-butyl ester 4-(6-Morpholin-4-yl-5-oxy-1H-pyrrolo[3,2-c]pyridin-3-yl)-3,6-dihydro-2H-pyridine-1-carboxylic acid tert-butyl ester (140 mg, 0.35 mmol) in EtOH (20 mL) containing PtO$_2$ (50 mg) was placed on a Parr hydrogenator at 60 psi H$_2$. After 18 h mixture was filtered through celite and evaporated to give a white solid. Column chromatography (silica, 0–5% (2 N NH$_3$ in MeOH)/CH$_2$Cl$_2$) provided 56 mg (40%) of a white solid. TLC (silica, 5% MeOH/CH$_2$Cl$_2$): R$_f$=0.13. MS (electrospray): exact mass calculated for C$_{21}$H$_{30}$N$_4$O$_4$, 402.23; m/z found, 403.2 (M$^+$+H). $^1$H NMR (CDCl$_3$, 400 MHz): 11.63 (br s, 1H), 8.58 (s, 1H), 6.97 (br s, 1H), 6.69 (s, 1H), 4.26–4.08 (m, 2H), 3.73 (t, J=4.30 Hz, 4H), 3.17 (t, J=4.50 Hz, 4H), 2.92–2.74 (m, 3H), 1.91 (d, J=11.93 Hz, 2H), 1.62–1.50 (m, 2H), 1.43 (s, 9H).

D. 6-Morpholin-4-yl-3-piperidin-4-yl-1H-pyrrolo[3,2-c]pyridine 5-oxide 4-(6-Morpholin-4-yl-5-oxy-1H-pyrrolo[3,2-c]pyridin-3-yl)-piperidine-1-carboxylic acid tert-butyl ester (56 mg, 0.14 mmol) was set stirring in 1:1 TFA/CH$_2$Cl$_2$. After 45 min the mixture was evaporated. The residue was dissolved in MeOH (10 mL) and neutralized with DOWEX 550A OH anion exchange resin to pH 8. The resin was then filtered off and MeOH was removed under reduced pressure to give 42 mg (100%) of a yellow solid. MS (electrospray): exact mass calculated for C$_{16}$H$_{22}$N$_4$O$_2$, 302.17; m/z found, 303.1 [M$^+$+H].

E. 1-[5-Methanesulfonyl-3-(4-trifluoromethyl-phenyl)-4,5,6,7-tetrahydro-pyrazolo[4,3-c]pyridin-1-yl]-3-[4-(6-morpholin-4-yl-5-oxy-1H-pyrrolo[3,2-c]pyridin-3-yl)-piperidin-1-yl]-propan-2-ol 6-Morpholin-4-yl-3-piperidin-4-yl-1H-pyrrolo[3,2-c]pyridine 5-oxide (42 mg, 0.14 mmol) and 5-methanesulfonyl-1-oxiranylmethyl-3-(4trifluoromethyl-phenyl)-4,5,6,7-tetrahydro-1H-pyrazolo[4,3-c]pyridine (84 mg, 0.21 mmol) were set stirring in $^i$PROH (5 mL) at 80° C. After 6 h the mixture was cooled and concentrated. The residue was purified by column chromatography (silica, 0–10% (2 N NH$_3$ in MeOH)/CH$_2$Cl$_2$) to obtain 5.1 mg (5%) of a white solid. TLC (silica, 10% (2 N NH$_3$ in MeOH)/CH$_2$Cl$_2$): R$_f$=0.54. MS (electrospray): exact mass calculated for C$_{33}$H$_{40}$F$_3$N$_7$O$_5$S, 703.28; m /z found, 704.3 [M$^+$+H]. $^1$H NMR (CDCl$_3$, 400 MHz): 8.60 (s, 1H), 7.71 (d, J=8.41 Hz, 2H), 7.66 (d, J=8.41 Hz, 2H), 7.27 (s, 1H), 6.95 (s, 1H), 6.70 (s, 1H), 4.55 (dd, J=14.48 Hz, 3.13 Hz, 2H), 4.23–4.11 (m, 2H), 4.05–3.97 (m, 1H), 3.84 (t, J=4.30 Hz, 4H), 3.72–3.60 (m, 2H), 3.23 (t, J=4.30 Hz, 4H), 3.12–2.98 (m, 2H), 2.97–2.89 (m, 2H), 2.88 (s, 3H), 2.73–2.63 (m, 1H), 2.51–2.36 (m, 3H), 2.17–2.08 (m, 1H), 1.99–1.90(m, 2H), 1.78–1.58 (m, 2H).

Example 11

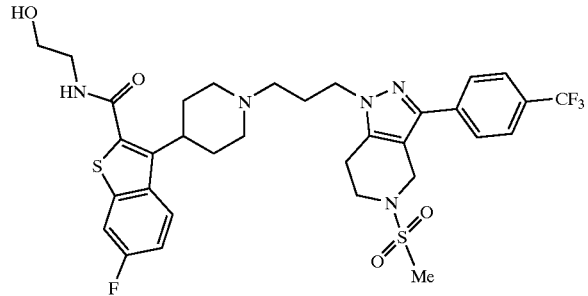

6-Fluoro-3-(1-{3-[5-methanesulfonyl-3-(4-trifluoromethyl-phenyl)-4,5,6,7-tetrahydro-pyrazolo[4,3-c]pyridin-1-yl]-propyl}-piperidin-4-yl)benzo[b]thiophene-2-carboxylic acid (2-hydroxy-ethyl)-amide A. 1-[4-(2,4-Difluoro-benzoyl)-piperidin-1-yl]-ethanone A stirred solution of 10 g (58.5 mmol) of 1-acetylpiperidine-4-carboxylic acid in anhydrous dichloroethane (35 mL) was treated with 5.1 mL (70.2 mmol) of thionyl chloride in 7 mL of dichloroethane and then heated to 60° C. for 30 min. Another flask containing a suspension of 8.02 mL (81.8 mmol) of 1,3-difluorobenzene and 17.9 g (134 mmol) of aluminum chloride in 55 mL of dichloroethane was prepared, to this was added the previously prepared acid chloride suspension in portions. The resulting suspension was refluxed for 4 h, cooled and then poured over ice and HCl. The acidic solution was extracted with CH$_2$Cl$_2$ (3×300 mL) and the combined organic extracts were washed with brine, dried over Na$_2$SO$_4$, and concentrated. The crude product was recrystallized from hexanes to afford 9.5 g (61%) of the desired product as a white solid. MS (electrospray): exact mass calculated for C$_{14}$H$_{15}$F$_2$NO$_2$, 267.11; m/z found, 268.1 [M+H]$^+$, $^1$H NMR (CDCl$_3$, 400 MHz): 7.87 (dt, J=8.41, 6.65 Hz 1H), 6.98 (m, 1H), 6.88 (ddd, J=10.96, 8.61, 2.35 Hz, 1H), 4.55 (m, 1H), 3.87 (m, 1H), 3.32 (dtt, J=10.76, 3.91, 1.37 Hz, 1H), 3.19 (ddd, J=13.89, 11.93, 2.93 Hz, 1H), 2.79 (ddd, J=13.89, 12.24, 2.93 Hz, 1H), 2.10 (s, 3H), 1.95 (br d, J=12.91 Hz, 2H), 1.72 (br m, 1H), 1.56 (br m, 1H).

B. 3-(1-Acetyl-piperidin-4-yl)-6-fluoro-benzo[b]thiophene-2-carboxylic acid methyl ester To a stirred solution of 33.6 g (0.126 mol) of 1-[4-(2,4-difluoro-benzoyl)-piperidin-1-yl]-ethanone and 13 mL (145 mol) of methyl thioglycolate in 320 mL dry THF was added 5.8 g (145 mol) of 60% sodium hydride in mineral oil in portions. The reaction mixture was heated to reflux overnight, allowed to cool to room temperature and the solvent removed under reduced pressure. The residue was then partitioned between 300 mL of CH$_2$Cl$_2$ and 200 mL of water. The aqueous layer was further extracted with CH$_2$Cl$_2$ (2×500 mL). The combined organic layers were washed with brine, dried over Na$_2$SO$_4$, and concentrated to give a residue which was then triturated with hexanes/EtOAc to give 27.5 g (65%) of the desired product as a white solid. MS (electrospray): exact mass calculated for C$_{17}$H$_{18}$FNO$_3$S, 335.1; m/z found, 336.1 [M+H]$^+$. $^1$H NMR (DMSO-d$_6$, 400 MHz, a mixture of amide rotamers): 7.12 (m, 2H), 6.92 (dt, J=8.41, 1.77 Hz, 1H), 4.43 (d, J=3.79 Hz, 1H), 4.43–4.36 (m, 1H), 3.82 (bt, J=14.65 Hz, 1H), 3.57 (s, 3H), 2.92–2.79 (m, 1H), 2.38–2.34 (m, 1H), 1.94 (s, 1.5H), 1.93 (s, 1.5H), 1.86–1.72 (m, 1H), 1.47–1.38 (m, 1H), 1.38–1.27 (m, 0.5H), 1.27–1.16 (m, 1H), 1.15–1.03 (m, 0.5H).

C. 6-Fluoro-3-piperidin-4-yl-benzo[b]thiophene-2-carboxylic acid methyl ester hydrochloride salt A solution of 24.4 g (66.8 mmol) of 3-(1-acetyl-piperidin-4-yl)-6-fluoro-benzo[b]thiophene-2-carboxylic acid methyl ester in 400 mL of MeOH and 50 mL of concentrated HCl was heated a reflux for 2 days. When the solution was allowed to cool to room temperature the white precipitate was filtered, washed with methanol and dried to give 17.9 g (74%) of product as a white powder. MS (electrospray): exact mass calculated for C$_{15}$H$_{16}$FNO$_2$S, 293.09; m/z found, 294.1 [M+H]$^+$. $^1$H NMR (DMSO-d$_6$, 400 MHz): 9.38 (brs, 1H), 9.02 (brs, 1H), 8.60 (dd, J=9.19, 5.09 Hz, 1H), 7.98 (dd, J=9.00, 2.54 Hz, 1H), 7.36 (dt, J=9.00, 2.54 Hz, 1H), 4.37 (br t, J=12.72 Hz, 1H), 3.87 (s, 3H), 3.40 (br d, J=11.93 Hz, 2H), 3.02 (q, J=11.35 Hz, 2H), 2.61 (dq, J=13.30, 3.72 Hz, 2H), 1.77 (br d, J=12.91 Hz, 2H).

D. 3-[5-Methanesulfonyl-3-(4-trifluoromethyl-phenyl)-4,5,6,7-tetrahydro-pyrazolo[4,3-c]pyridin-1-yl]-propan-1-ol Cs$_2$CO$_3$ (33.74 g, 103.5 mmol) was added to a solution of 5-methanesulfonyl-3-(4-trifluoromethyl-phenyl)-4,5,6,7-tetrahydro-1H-pyrazolo[4,3-c]pyridine (29.8 g, 86.3 mmol) in anhydrous DMF (70 mL) and stirred for 25 min. 3-Bromo-1-propanol (8.6 mL, 13.2 g, 94.9 mmol) was added and stirred under N$_2$ at room temperature for 18 h. Water (500 mL) was added to the reaction and stirred for 5 min. The precipitated material was filtered out and washed with water (4×100 mL) and dried. The crude material (31.0 g) was taken up in anhydrous DMF (65 mL) and Cs$_2$CO$_3$ (33.74 g, 103.5 mmol) was added, and stirred for 10 min.

Then 3-bromo-1-propanol (8.6 mL, 13.2 g, 94.9 mmol) and MeOH (6.0 mL, 4.75 g, 148 mmol) were added and stirring continued under $N_2$ at rt for 15 h. Water (500 mL) was added to the reaction and stirred for 10 min. The precipitated material was filtered and washed with water (3×100 mL). The filter cake was dissolved in $CH_2Cl_2$ (200 mL) and washed with brine (50 mL), dried ($Na_2SO_4$), and concentrated. The solid was triturated with $Et_2O$ (200 mL), filtered, then washed with $Et_2O$, and dried to furnish 16.0 g of the desired compound. The mother liquor was chromatographed (silica, 0–10% acetone/EtOAc) to obtain an additional 3.0 g of the title compound. The combined yield was 54.6%. MS (electrospray): exact mass calculated for $C_{17}H_{20}F_3N_3O_3S$, 403.12; m/z found, 404.0 [M+H]$^+$. $^1$H NMR (400 MHz, CDCl$_3$): 7.71 (d, J=8.2 Hz, 2H), 7.66 (d, J=8.5 Hz, 2H), 4.55 (s, 2H), 4.23 (t, J=6.5 Hz, 2H), 3.70–3.63 (m, 4H), 2.90 (s, 3H), 2.90 (t, J=5.1 Hz, 2H), 2.62 (t, J=5.9 Hz, 1H), 2.06 (q, J=6.1 Hz, 2H).

E. 3-[5-Methanesulfonyl-3-(4-trifluoromethyl-phenyl)-4,5, 6,7-tetrahydro-pyrazolo[4,3-c]pyridin-1-yl]-propionaldehyde Dess-Martin periodinane (3.45 g, 8.2 mmol) was added to a solution of 3-[5-methanesulfonyl-3-(4-trifluoromethyl-phenyl)-4,5,6,7-tetrahydro-pyrazolo[4,3-c]pyridin-1-yl]-propan-1-ol (3.0 g, 7.4 mmol) in $CH_2Cl_2$ (20 mL) at 0° C. under $N_2$. After 15 min, the reaction was allowed to warm to room temperature and stirred for another 1.5 h. The reaction was diluted with $Et_2O$ (60 mL) and 20% aq. $NaHCO_3$ (35 mL) was added slowly (caution! rapid gas evolution). Then $Na_2S_2O_3$ was added and stirred at room temperature for 30 min. The layers were separated and the aqueous portion was extracted with $Et_2O$ (2×30 mL). The combined organic extracts were washed with brine, dried ($Na_2SO_4$) and concentrated. MPLC (silica, 1–10% MeOH/$CH_2Cl_2$) afforded 2.53 g of the desired aldehyde in 85% yield. MS (electrospray): exact mass calculated for $C_{17}H_{18}F_3N_3O_3S$, 401.11; m/z found, 402.1 [M+H]. $^1$H NMR (400 MHz, CDCl$_3$): 9.82 (s, 1H), 7.63 (d, J=8.4 Hz, 2H), 7.58 (d, J=8.4 Hz, 2H), 4.68 (s, 2H), 4.25 (t, J=6.1 Hz, 2H), 3.63 (t, J=5.8 Hz, 4H), 3.14 (t, J=6.1 Hz, 2H), 2.92 (t, J=5.8 Hz, 2H), 2.81 (s, 3H).

F. 6-Fluoro-3-(1-{3-[5-methanesulfonyl-3-(4-trifluoromethyl-phenyl)-4,5,6,7-tetrahydro-pyrazolo[4,3-c]pyridin-1-yl]-propyl}-piperidin-4-yl)benzo[b]thiophene-2-carboxylic acid methyl ester To a stirred solution of 410 mg (1.25 mmol) of 6-fluoro-3-piperidin-4-yl-benzo[b]thiophene-2-carboxylic acid methyl ester hydrochloride salt in 10 mL of dichloromethane and 0.18 mL (1.25 mmol) of triethylamine was added 500 mg of 3-[5-methanesulfonyl-3-(4-trifluoromethyl-phenyl)-4,5,6,7-tetrahydro-pyrazolo[4,3-c]pyridin-1-yl]-propionaldehyde (1.25 mmol) and 2 g of $NaHCO_3$. The mixture was stirred for 4 h before the portion wise addition of 792 mg (3.73 mmol) sodium triacetoxyborohydride. The reaction was stirred at room temperature for 3 h before quenching with 20 mL of water. The aqueous phase was extracted with $CH_2Cl_2$ (3×50 mL). The combined organic layers were then washed with brine, dried over $Na_2SO_4$, and concentrated. The crude product was purified by column chromatography (silica, 0–5% MeOH/$CH_2Cl_2$) to afford 650 mg (77%) of a white solid. MS (electrospray): exact mass calculated for $C_{32}H_{34}F_4N_4O_4S_2$: 678.20; m/z found, 679.2 [M+H]$^+$. $^1$H NMR (CDCl$_3$, 400 MHz): 7.74 and 7.66 (A and B of AB quartet, J=8.22 Hz, 4H), 7.50 (dd, J=8.41, 2.54 Hz 1H), 7.14 (t, J=8.22 Hz, 1H), 4.56 (s, 2H), 4.17 (m, 3H), 3.91 (s, 3H), 3.70 (t, J=5.67 Hz, 2H), 3.03 (br m, 2H), 3.00 (t, J=5.67 Hz, 2H), 2.90 (s, 3H), 2.40 (br m, 4H), 2.13 (br m, 4H), 1.76 (br d, J=11.15 Hz, 4H).

G. 6-Fluoro-3-(1-{3-[5-methanesulfonyl-3-(4-trifluoromethyl-phenyl)-4,5,6,7-tetrahydro-pyrazolo[4,3-c]pyridin-1-yl]-propyl}-piperidin-4-yl)benzo[b]thiophene-2-carboxylic acid To a stirred solution of 635 mg (0.94 mmol) of 6-fluoro-3-(1-{3-[5-methanesulfonyl-3-(4-trifluoromethyl-phenyl)-4,5,6,7-tetrahydro-pyrazolo[4,3-c]pyridin-1-yl]-propyl}-piperidin-4-yl)-benzo[b]thiophene-2-carboxylic acid methyl ester in 10 mL of THF was treated a solution of 53 mg (0.94 mmol) of KOH in 0.5 mL of water. This was stirred overnight, after the hydrolysis was deemed complete 1 mL of 1 N HCl solution was added. This was then extracted with EtOAc (3×30 mL). The combined organic layers were then washed with brine, dried over $Na_2SO_4$, and concentrated to yield 622 mg (100%) of a white solid. MS (electrospray): exact mass calculated for $C_{31}H_{32}F_4N_4O_4S_2$: 664.18; m/z found, 665.2 [M+H]$^+$. $^1$H NMR (DMSO-d$_6$, 400 MHz): 8.12 (dd, J=8.81, 5.28 Hz, 1H), 7.83 and 7.76 (A and B of AB quartet, J=8.41 Hz, 4H), 7.17 (br t, J=8.61 Hz, 1H), 4.47 (s, 2H), 4.29 (brs, 1H), 4.16 (t, J=7.04 Hz, 2H), 3.53 (t, J=5.67 Hz, 2H), 3.28 (br m, 4H), 3.00 (s, 3H), 2.96 (m, 2H), 2.73 (br s, 2H), 2.52 (br m, 2H), 2.13 (br m, 2H), 1.76 (br m, 2H).

H. 6-Fluoro-3-(1-{3-[5-methanesulfonyl-3-(4-trifluoromethyl-phenyl)-4,5,6,7-tetrahydro-pyrazolo[4,3-c]pyridin-1-yl ]-propyl}-piperidin-4-yl)benzo[b]thiophene-2-carboxylic acid (2-hydroxy-ethyl)-amide A stirred solution of 20 mg (0.03 mmol) of 6-fluoro-3-(1-{3-[5-methanesulfonyl-3-(4-trifluoromethyl-phenyl)-4,5, 6,7-tetrahydro-pyrazolo[4,3-c]pyridin-1-yl]-propyl}-piperidin-4-yl)-benzo[b]thiophene-2-carboxylic acid in 0.3 mL of dry DMF was treated with 14 mg (0.036 mmol) of HBTU and 8 μL (0.045 mmol) of DIEA. The solution was stirred for 5 min before the addition of 0.01 mL (0.15 mmol) of ethanol amine. The reaction was stirred at room temperature for 30 min then partitioned between EtOAc (30 mL) and saturated $NaHCO_3$ (20 mL). The aqueous layer was further extracted with EtOAc (2×20 mL). The combined organic layers were then washed with brine, dried over $Na_2SO_4$, and concentrated. Purification by column chromatography (silica, 5–10% of 2 N $NH_3$ in MeOH/$CH_2Cl_2$) yielded 16 mg (76%) of a white solid. MS (electrospray): exact mass calculated for $C_{33}H_{37}F_4N_5O_4S_2$: 707.22; m/z found, 708.2 [M+H]$^+$. $^1$H NMR (CDCl$_3$, 400 MHz): 7.97 (br s, 1H), 7.73 and 7.66 (A and B of AB quartet, J=8.41 Hz, 4H), 7.49 (dd, J=8.41, 2.35 Hz, 1H), 7.15 (dt, J=8.61, 2.54 Hz, 1H), 6.41 (t, J=5.67 Hz, 1H), 4.56 (s, 2H), 4.16 (t, J=7.04 Hz, 2H), 3.84 (dd, J=5.28, 4.70 Hz, 2H), 3.70 (t, J=5.67 Hz, 2H), 3.62 (m, 2H), 3.58 (br s, 1H), 3.05 (br m, 2H), 2.97 (t, J=5.67 Hz, 2H), 2.91 (s, 3H), 2.40 (br m, 4H), 2.13 (br m, 4H), 1.84 (br d, J=12.32 Hz, 2H).

Example 12

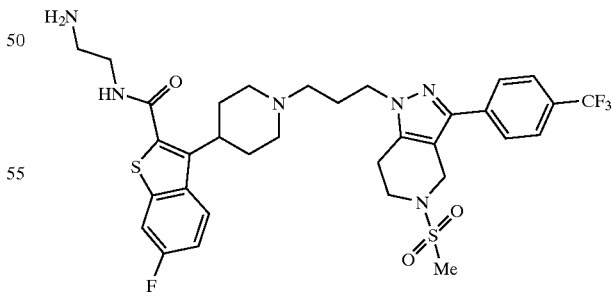

6-Fluoro-3-(1-{3-[5-methanesulfonyl-3-(4-trifluoromethyl-phenyl)-4,5,6,7-tetrahydro-pyrazolo[4,3-c]pyridin-1-yl]-propyl}-piperidin-4-yl)benzo[b]thiophene-2-carboxylic acid (2-amino-ethyl)-amide A stirred solution of 300 mg (0.43 mmol) 6-fluoro-3-(1-{3-[5-methanesulfonyl-3-(4-trifluoromethyl-phenyl)-4,5,6, 7-tetrahydro-pyrazolo[4,3-c]pyridin-1-yl]-propyl}-piperidin-4-yl)-benzo[b]thiophene-2-carboxylic acid in 5 mL of dry DMF was treated with 812 mg (2.14 mmol) of HBTU and 0.75 mL (4.28 mmol) of DIEA. The solution was stirred for 5 min before the addition of 0.28 mL (4.28 mmol) of ethylenediamine. The reaction was stirred at room temperature for 30 min then partitioned between EtOAc (30 mL) and saturated sodium bicarbonate (20 mL). The aqueous layer was further extracted with EtOAc (2×20 mL). The combined organic layers were then washed with brine, dried over Na$_2$SO$_4$, and concentrated. Purification by column chromatography (silica, 5–10% of (2 N NH$_3$ in MeOH)/CH$_2$Cl$_2$) afforded 200 mg (66%) of a clear oil. MS (electrospray): exact mass calculated for C$_{33}$H$_{38}$F$_4$N$_6$O$_3$S$_2$: 706.24; m/z found, 707.2 [M+H]$^+$. $^1$H NMR (CD$_3$OD, 400 MHz): 8.14 (m, 1H), 7.84 and 7.72 (A and B of AB quartet, J=8.41 Hz, 4H), 7.68 (m, 1H), 7.21 (dt, J=8.81, 2.74 Hz, 1H), 4.54 (s, 2H), 4.27 (t, J=6.26 Hz, 2H), 4.00–3.90 (m, 2H), 3.76–3.61 (m, 8H), 3.28–3.23 (br m, 1H), 3.19–3.09 (br m, 3H), 2.98 (s, 3H), 2.97–2.93 (m, 2H), 2.67 (br m, 2H), 2.52–2.37 (m, 3H), 2.02 (br d, J=13.89 Hz, 2H).

Example 13

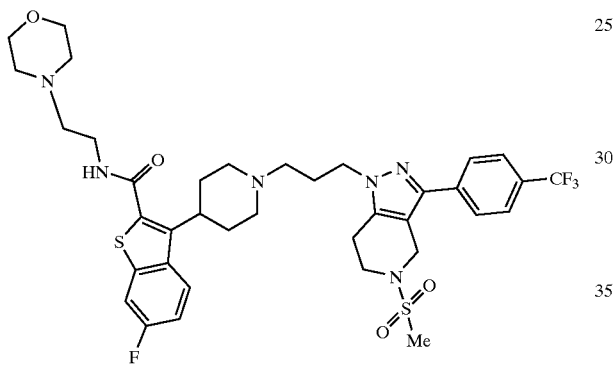

6-Fluoro-3-(1-{3-[5-methanesulfonyl-3-(4-trifluoromethyl-phenyl)-4,5,6,7-tetrahydro-pyrazolo[4,3-c]pyridin-1-yl]-propyl}-piperidin -4-yl)benzo[b]thiophene-2-carboxylic acid (2-morpholin -4-yl-ethyl)-amide A stirred solution of 20 mg (0.03 mmol) of 6-fluoro-3-(1-{3-[5-methanesulfonyl-3-(4-trifluoromethyl-phenyl )-4,5,6,7-tetrahydro-pyrazolo[4,3-c]pyridin -1-yl]-propyl}-piperidin-4-yl)-benzo[b]thiophene-2-carboxylic acid in 0.3 mL of dry DMF was treated with 14 mg (0.036 mmol) of HBTU and 8 μL (0.045 mmol) of DIEA. The solution was stirred for 5 min before the addition of 20 μL (0.15 mmol) of 4-(2-aminoethyl)morpholine. The reaction was stirred at room temperature for 30 min then partitioned between EtOAc (30 mL) and saturated NaHCO$_3$ (20 mL). The aqueous layer was further extracted with EtOAc (2×20 mL). The combined organic layers were then washed with brine, dried over Na$_2$SO$_4$, and concentrated. Purification by column chromatography (silica, 5–10% of (2 N NH$_3$ in MeOH)/CH$_2$Cl$_2$) afforded 15 mg (65%) of a white solid. MS (electrospray), exact mass calculated for C$_{37}$H$_{44}$F$_4$N$_6$O$_4$S$_2$: 776.28; m/z found, 777.3 [M+H]$^+$. $^1$H NMR (CDCl$_3$, 400 MHz): 8.07 (br s, 1H), 7.73 and 7.66 (A and B of AB quartet, J=8.41 Hz, 4H), 7.50 (dd, J=8.41, 2.35 Hz, 1H), 7.14 (dt, J=8.61, 2.54 Hz, 1H), 6.64 (t, J=4.70 Hz, 1H), 4.56 (s, 2H), 4.16 (t, J=6.85 Hz, 2H), 3.80–3.67 (m, 7H), 3.53 (q, J=5.48 Hz, 2H), 3.03 (br m, 2H), 2.98 (t, J=5.67 Hz, 2H), 2.90 (s, 3H), 2.60 (t, J5.87 Hz, 2H), 2.38 (br m, 4H), 2.12 (br m, 4H), 1.86–1.73 (br m, 3H).

Example 14

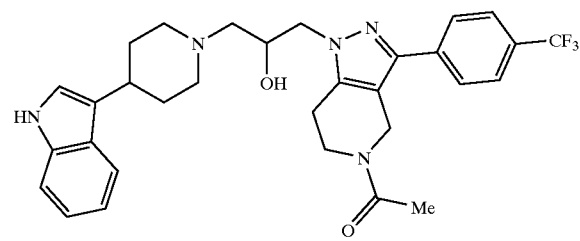

1-[1-{2-Hydroxy-3-[4-(1H-indol-3-yl)-piperidin-1-yl]-propyl}-3-(4trifluoromrthyl-phenyl)-1,4,6,7-tetrahydro-pyrazolo[4,3-c]pyridin-5-yl]-ethanone Example 15

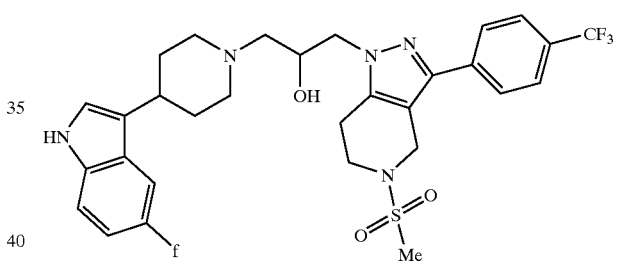

1-[4-(5-Fluoro-1H-indol-3-yl)-piperidin-1-yl]-3-[5-methanesulfonyl-3-(4-trifluoromethyl-phenyl)-4,5,6,7-tetrahydro-pyrazolo[4,3-c]pyridin-1-yl]-propan-2-ol Example 16

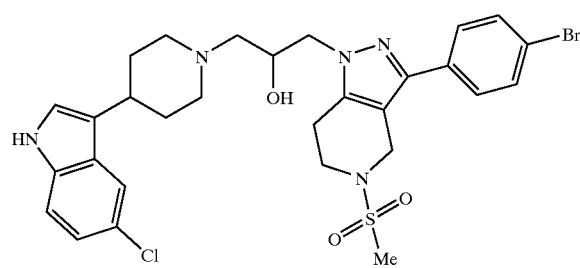

1-[3-(4-Bromo-phenyl)-5-methanesulfonyl-4,5,6,7-tetrahydro-pyrazolo[4,3-c]pyridin-1-yl]-3-[4-(5-chloro-1H-indol-3-yl)-piperidin-1-yl]-propan-2-ol Example 17

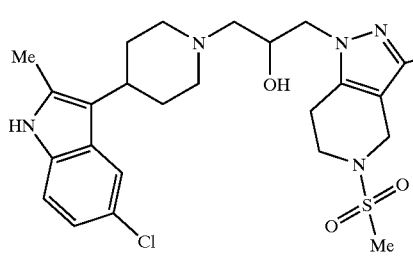

1-[3-(4-Bromo-phenyl)-5-methanesulfonyl-4,5,6,7-tetrahydro-pyrazolo[4,3-c]pyridin-1-yl]-3-[4-(5-chloro-2-methyl-1H-indol-3-yl)-piperidin-1-yl]-propan-2-ol Example 18

1-[5-Methanesulfonyl-3-(4-trifluoromethyl-phenyl)-4,5,6,7-tetrahydro-pyrazolo[4,3-c]pyridin-1-yl]-3-[4-(5-methyl-1H-indol-3-yl)-piperidin-1-yl]-propan-2-ol Example 19

3-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1H-indole-5-carbonitrile Example 20

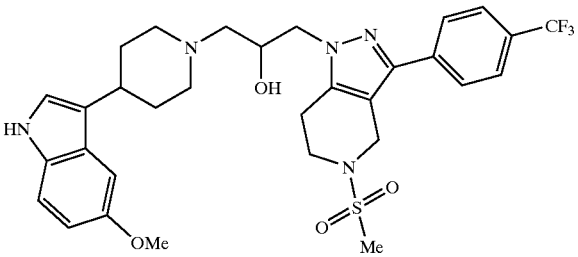

1-[5-Methanesulfonyl-3-(4-trifluoromethyl-phenyl)-4,5,6,7-tetrahydro-pyrazolo[4,3-c]pyridin-1-yl]-3-[4-(5-methoxy-1H-indol-3-yl)-piperidin-1-yl]-propan-2-ol Example 21

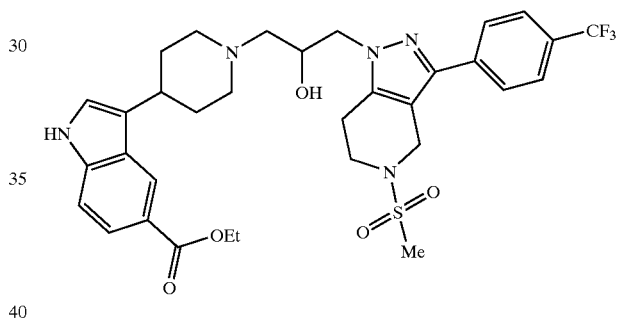

3-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1H-indole-5-carboxylic acid ethyl ester Example 22

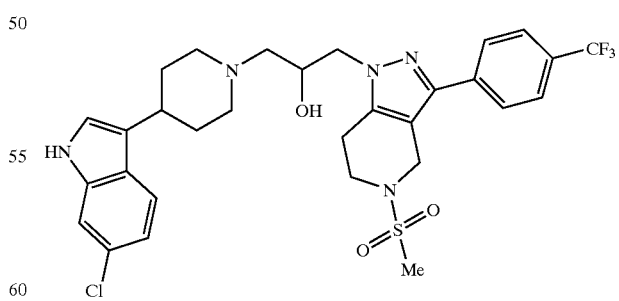

1-[4-(6-Chloro-1H-indol-3-yl)-piperidin-1-yl]-3-[5-methanesulfonyl-3-(4-trifluoromethyl-phenyl)-4,5,6,7-tetrahydro-pyrazolo[4,3-c]pyridin-1-yl]-propan-2-ol

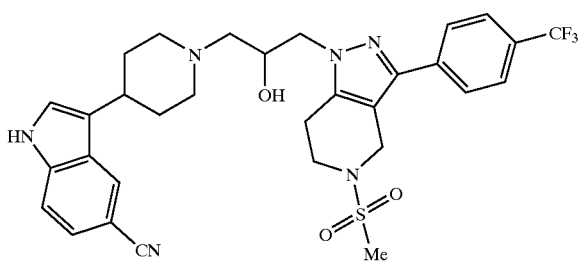

Example 23

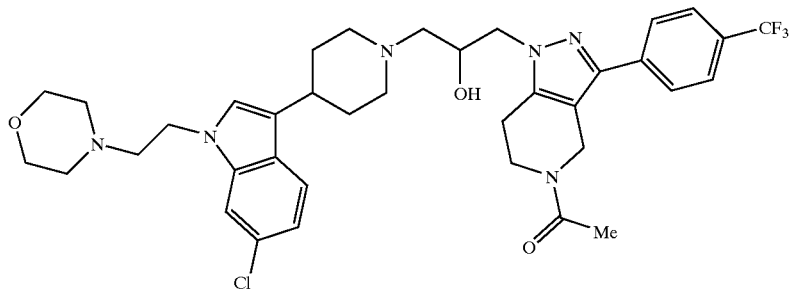

1-[1-(3-{4-[6-Chloro-1-(2-morpholin-4-yl-ethyl)-1H-indol-3-yl]-piperidin-1-yl}-2-hydroxy-propyl)-3-(4-trifluoromethyl-phenyl)-1,4,6,7-tetrahydro-pyrazolo[4,3-c]pyridin-5-yl]-ethanone Example 24

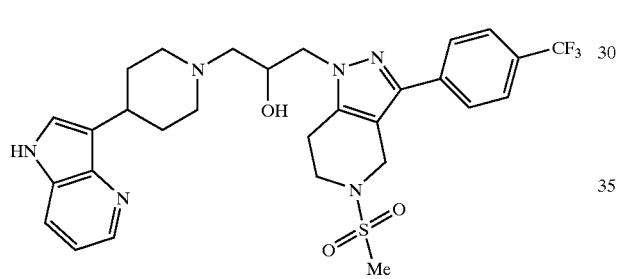

1-[5-Methanesulfonyl-3-(4-trifluoromethyl-phenyl)-4,5,6,7-tetrahydro-pyrazolo[4,3-c]pyridin-1-yl]-3-[4-(1H-pyrrolo[3,2-b]pyridin-3-yl)-piperidin-1-yl]-propan-2-ol Example 25

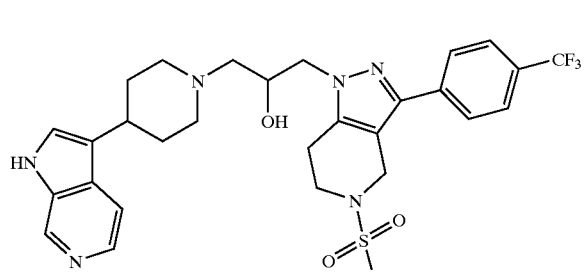

1-[5-Methanesulfonyl-3-(4-trifluoromethyl-phenyl)-4,5,6,7-tetrahydro-pyrazolo[4,3-c]pyridin-1-yl]-3-[4-(1H-pyrrolo[2,3-c]pyridin-3-yl)-piperidin-1-yl]-propan-2-ol Example 26

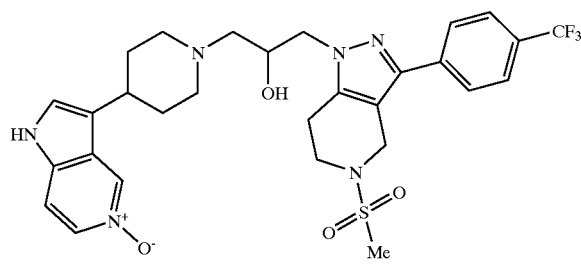

1-[5-Methanesulfonyl-3-(4-trifluoromethyl-phenyl)-4,5,6,7-tetrahydro-pyrazolo[4,3-c]pyridin-1-yl]-3-[4-(5-oxy-1H-pyrrolo[3,2-c]pyridin-3-yl)-piperidin-1-yl]-propan-2-ol Example 27

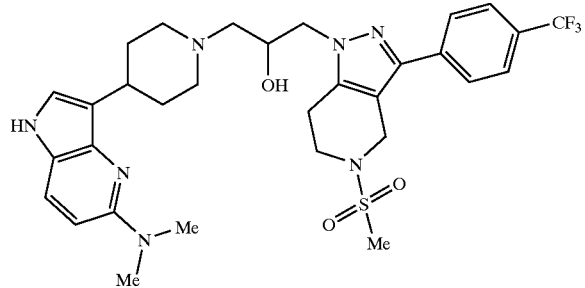

1-[4-(5-Dimethylamino-1H-pyrrolo[3,2-b]pyridin-3-yl)-piperidin-1-yl]-3-[5-methanesulfonyl-3-(4-trifluoromethyl-phenyl)-4,5,6,7-tetrahydro-pyrazolo[4,3-c]pyridin-1-yl]-propan-2-ol Example 28

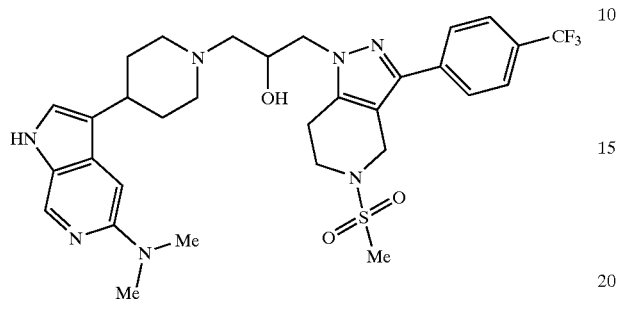

1-[4-(5-Dimethylamino-1H-pyrrolo[2,3-c]pyridin-3-yl)-piperidin-1-yl]-3-[5-methanesulfonyl-3-(4-trifluoromethyl-phenyl)-4,5,6,7-tetrahydro-pyrazolo[4,3-c]pyridin-1-yl]-propan-2-ol Example 29

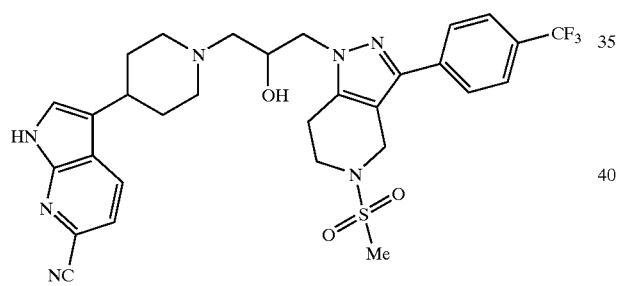

3-(1-{2-Hydroxy-3-[5-methanesulfonyl-3-(4-trifluoromethyl-phenyl)4,5,6,7-tetrahydro-pyrazolo[4,3-c]pyridin-1-yl]-propyl}-piperidin-4-yl)-1H-pyrrolo[2,3-b]pyridine-6-carbonitrile Example 30

1-[5-Methanesulfonyl-3-(4-trifluoromethyl-phenyl)-4,5,6,7-tetrahydro-pyrazolo[4,3-c]pyridin-1-yl]-3-{4-[1-(2-morpholin-4-yl-ethyl)-1H-pyrrolo[2,3-b]pyridin-3-yl]-piperidin-1-yl}-propan-2-ol Example 31

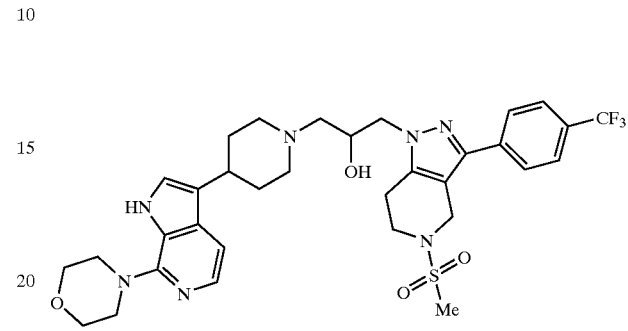

1-[5-Methanesulfonyl-3-(4-trifluoromethyl-phenyl)-4,5,6,7-tetrahydro-pyrazolo[4,3-c]pyridin-1-yl]-3-[4-(7-morpholin-4-yl-1H-pyrrolo[2,3-c]pyridin-3-yl)-piperidin-1-yl]-propan-2-ol Example 32

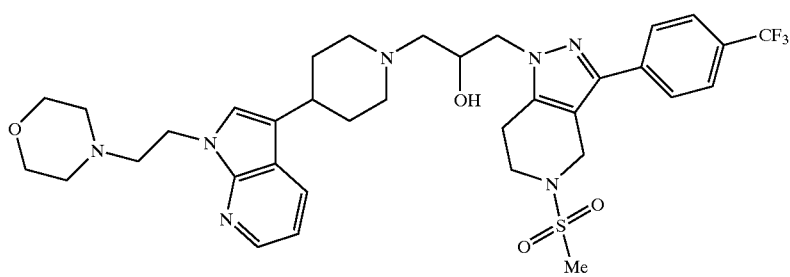

61

1-[4-(6-Fluoro-2-hydroxymethyl-benzo[b]thiophen-3-yl)-piperidin-1-yl]-3-[5-methanesulfonyl-3-(4-trifluoromethyl-phenyl)-4,5,6,7-tetrahydro-pyrazolo[4,3-c]pyridin-1-yl]-propan-2-ol

Example 33

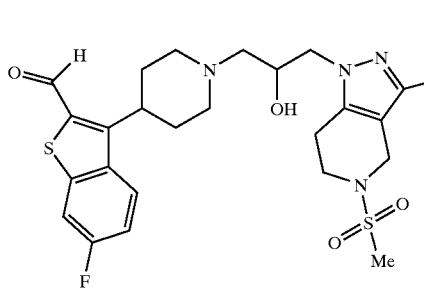

6-Fluoro-3-(1-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-benzo[b]thiophene-2-carbaldehyde

Example 34

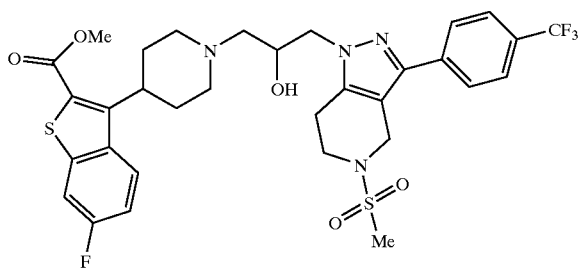

6-Fluoro-3-(1-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-benzo[b]thiophene-2-carboxylic acid methyl ester

Example 35

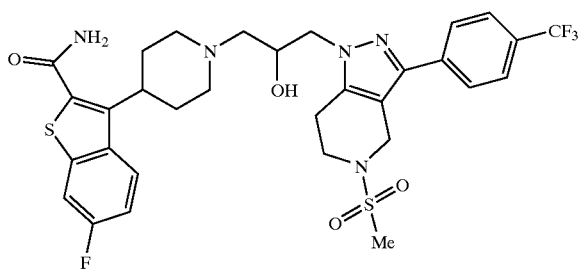

62

6-Fluoro-3-(1-{3-[5-methanesulfonyl-3-(4-trifluoromethyl-phenyl)-4,5,6,7-tetrahydro-pyrazolo[4,3-c]pyridin-1-yl]-propyl}-piperidin-4-yl)benzo[b]thiophene-2-carboxylic acid amide

Example 36

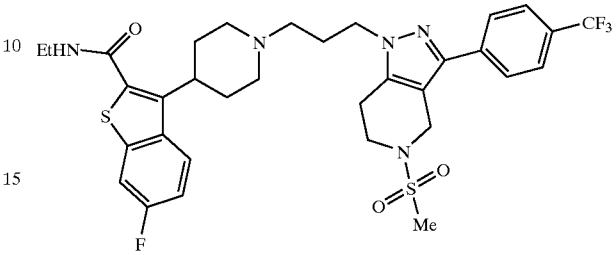

6-Fluoro-3-(1-{3-[5-methanesulfonyl-3-(4-trifluoromethyl-phenyl)-4,5,6,7-tetrahydro-pyrazolo[4,3-c]pyridin-1-yl]-propyl}-piperidin-4-yl)benzo[b]thiophene-2-carboxylic acid ethylamide

Example 37

Cathepsin S Inhibition Assay

Recombinant human cathepsin S (CatS) was expressed in the baculovirus system and purified in one step with a thiopropyl-sepharose column. 10-L yielded ~700 mg of CatS and N-terminal sequencing confirmed identity. The assay is run in 100 mM sodium acetate pH 5.0 containing 1 mM DTT and 100 mM NaCl. The substrate for the assay is (Aedens)EKARVLAEAA(Dabcyl)K-amide The $K_m$ for the substrate is around 5 $\mu$M but the presence of substrate inhibition makes kinetic analysis difficult. With 20 $\mu$M substrate the assay rate is linear over the range of 1–8 ng CatS in 100 $\mu$l reaction. Using 2 ng/well of CatS, the production of product is linear and yields ~7-fold signal after 20 min with only 20% loss of substrate. Primary assays are run by quenching the reaction after 20 min with 0.1% SDS and then measuring the fluorescence. For other assays, measurements are taken every min for 20 min. The rate is calculated from the slope of the increase and the percent inhibition is calculated from this (See Tables 1 and 2 below).

TABLE 1

| EXAMPLE | IC$_{50}$ ($\mu$M) |
|---------|--------------------|
| 1       | 0.07               |
| 2       | 0.03               |
| 3       | 0.05               |
| 4       | 0.09               |
| 5       | 0.03               |
| 6       | 0.03               |
| 7       | 0.05               |
| 8       | 0.03               |
| 9       | 0.02               |
| 10      | 0.02               |
| 11      | 0.02               |
| 12      | 0.05               |
| 13      | 0.05               |

TABLE 2

| EXAMPLE | IC$_{50}$ ($\mu$M) |
|---|---|
| 14 | 0.07 |
| 15 | 0.04 |
| 16 | 0.06 |
| 17 | 0.03 |
| 18 | 0.06 |
| 19 | 0.02 |
| 20 | 0.02 |
| 21 | 0.04 |
| 22 | 0.03 |
| 23 | 0.08 |
| 24 | 0.13 |
| 25 | 0.05 |
| 26 | 0.09 |
| 27 | 0.10 |
| 28 | 0.07 |
| 29 | 0.08 |
| 30 | 0.02 |
| 31 | 0.07 |
| 32 | 0.14 |
| 33 | 0.08 |
| 34 | 0.13 |
| 35 | 0.03 |
| 36 | 0.04 |

Example 38
Ex vivo Inhibition by Cathepsin S Inhibitors of the Allergenic Response The following assay demonstrates that cathepsin S inhibitors block the response of human T cells to crude allergen extracts.

Materials and Methods

Reagents. Glycerinated crude allergen extracts of house dust mites (*Dermataphagoides pteronyssinus, Dermataphagoides farinae*) and ragweed [*Ambrosia trifida* (giant), *Ambrosia artemisiifolia* (short)] were purchased from Hollister-Stier Laboratories (Minneapolis, Minn.). Concanavalin A (ConA) was purchased from Calbiochem (La Jolla, Calif.).

Donors. All allergic donors were prescreened for their specific allergies using RAST tests. The HLA class II haplotypes of these donors were determined using PCR.

Cell culture. Human peripheral blood mononuclear cells (PBMC) were purified from blood of allergic donors using Ficoll-Hypaque gradient followed by washes with phosphate buffered saline (PBS). PBMC were cultured in triplicate or duplicate at 0.5–1.0×10$^6$ cells/well with titrated doses of allergen extracts, in the presence or absence of a known cathepsin S inhibitor, LHVS (morpholinurea-leucine-homo-phenylalanine-vinylsulfonephenyl) (Palmer et al. (1995), J. Med. Chem. 38:3193 and Riese et al. (1996), Immunity 4:357). Serial diluted stock solutions of LHVS were first made in 100% DMSO and then diluted 1:15 in 40% Hydroxypropynyl cyclodextrin (HPCD). Three microliters of LHVS in HPCD was added into PBMC cultures (200 $\mu$L/well). After 6 days of culture, 1 $\mu$Ci/well of $^3$H-thymidine (TdR) was added. Eighteen hours later, cells were harvested using a Filtermate Harvester (Packard) and counted for $^3$H-TdR incorporation on Topcount (Packard).

Inhibition of T cell Proliferative Responses to House Dust Mites

About 10% of most populations are allergic to house dust mites (HDM) of the genus Dermatophagoides with *Dermatophagoides pteronyssinus* (Der p) and *D. farinae* (Der f) being the two major species present in varying proportions in most countries. The major clinical manifestations are asthma and perennial rhinitis.

Effect of cathepsin S inhibition on activation of HDM allergen-specific CD4 T cells was tested in an ex vivo human T cell-proliferation assay. Culturing PBMC with crude extracts from either Der p or Der f, resulted in strong proliferation (FIG. 1A). This proliferation consisted primarily of allergen-specific CD4 T cells. When cathepsin S activity was blocked by a specific cathepsin S inhibitor, LHVS (cf. Riese et al. (1996) Immunity 4:357) the proliferation was strongly inhibited (FIG. 1B). Inhibition by LHVS was specific for responses induced by HDM extracts since T cell proliferative responses induced by ConA, a pan-T cell mitogen, were not affected. Furthermore, this inhibition was observed for all four HDM-allergic donors tested regardless of the different HLA class II haplotypes (DR4; DR7, 15; DR11, 15; and DR4, 11).

This system is very similar to an in vivo situation. The allergic subject would be exposed to a crude mixture of allergens that would lead to the proliferation of T cells and an allergic response. The observation of inhibition of CD4 T cell activation by a cathepsin S inhibitor shows that such inhibitors can be effective in treating a generalized population of patients allergic to house dust mites.

Inhibition of T cell Proliferative Responses to Ragweed

About 10% of population in US are allergic to ragweed pollen, making it one of the most important allergens in terms of clinical diseases. Allergens from pollens are a common precipitant of rhinitis and asthma in this population.

Figure 2:
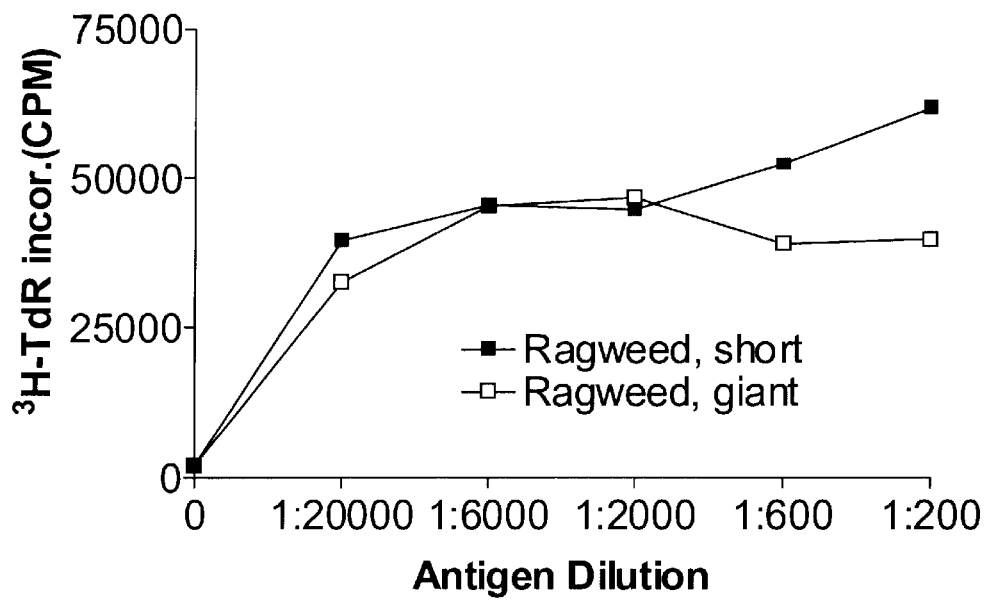
FIG. 2 is shows the inhibition of human T cell proliferative responses to ragweeds but not ConA by LHVS. Top panel.
Figure 2:
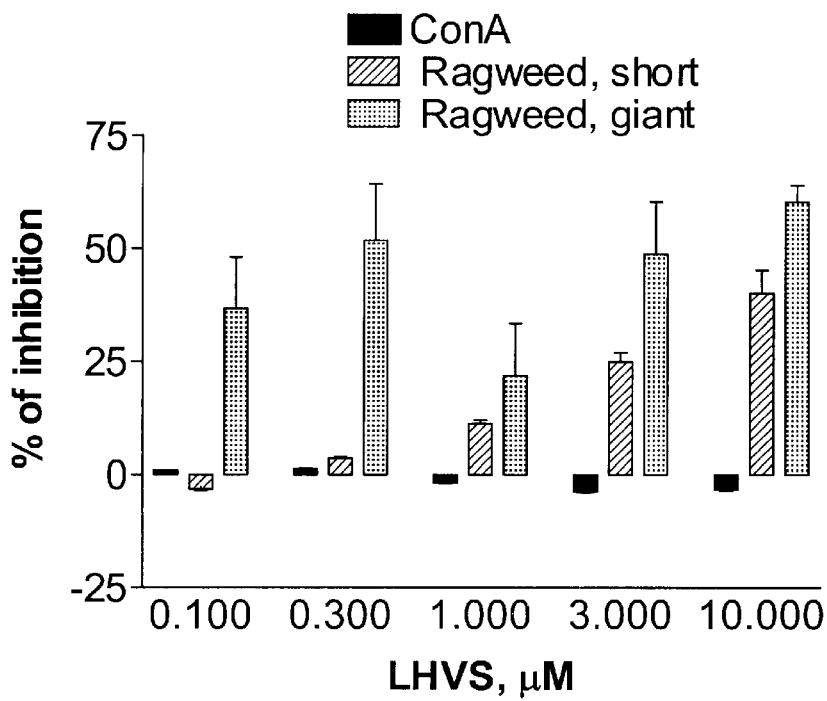

The effect of cathepsin S inhibition on activation of ragweed allergen-specific CD4 T cells was tested in an ex vivo human T cell-proliferation assay. Culturing PBMC with crude extracts from both short and giant ragweed resulted in strong proliferation (FIG. 2A). This proliferation consisted mainly of allergen-specific CD4 T cells. When cathepsin S activity was blocked by a specific cathepsin S inhibitor, LHVS (cf. Riese et al. (1996) Immunity 4:357) the proliferation was strongly inhibited (FIG. 2B). Inhibition by LHVS was specific for responses induced by ragweed since T cell proliferative responses induced by ConA, a pan-T cell mitogen, were not affected. Furthermore, this inhibition was observed for the two ragweed-allergic donors tested regardless of the different HLA class II haplotypes (DR7, 15 and DR4, 11).

This system is very similar to an in vivo situation. The allergic subject would be exposed to a crude mixture of allergens that would lead to the proliferation of T cells and an allergic response. The observation of inhibition of CD4 T cell activation by a cathepsin S inhibitor shows that such inhibitors can be effective in treating a generalized population of patients allergic to ragweed.

Example 39
Monitoring Cathepsin S Inhibition in Human Blood

The effect of in vivo administration of cathepsin S inhibitors, in a clinical trial setting, can be monitored by measuring accumulation of an intermediate degradation product of invariant chain (Ii), i.e. the p10Ii fragment, in blood of dosed subjects. After administration of a cathepsin inhibitor for a certain period of time, for example, between 0.01 and 50 mg/kg/day, to result in a blood concentration of between 1 nM–10 $\mu$M, for 16–30 h, blood is drawn and white blood cells are purified, e.g. either by lysis of red blood cells or by a Ficoll-Hypaque gradient centrifugation. Whole cell lysates of WBC are then made and analyzed by either a Western blot assay or an ELISA assay. For the Western blot assay, cell lysates are first resolved on SDS-PAGE gels. After transferring to nitrocellulose membranes, Ii and its intermediate degradation products, including the p10Ii, can be detected using a mouse mAb against Ii, e.g. Pin1.1, or rabbit polyclonal antibodies or a mouse monoclonal antibody specific for the p10Ii fragment or against the entire p10Ii fragment. For ELISA assay, a pair of antibodies against Ii, including Pin1.1, and a rabbit polyclonal antibody against C-terminal of p10Ii, can be used. The same assay can also be applied to monitor the effect of cathepsin S inhibitors in vivo in animal studies, for example in monkeys, dogs, pigs, rabbits, guinea pigs, and rodents.

In the present example PBMC from human blood were incubated with the cathepsin S inhibitor, LHVS (morpholinurea-leucine-homo-phenylalanine-vinylsulfonephenyl, also referred to as 4-morpholinecarboxamide, N-[(1S)-3-methyl-1-[[[(1S,2E)-1-(2-phenylethyl)-3-(phenylsulfonyl)-2-propenyl]amino]carbonyl]butyl]-. This compound has been described in U.S. Pat. No. 5,976,858 and in Palmer et al. (1995) J. Med. Chem. 38:3193 and Riese et al. (1996) Immunity 4:357. After incubation for 24 h the samples were run using standard SDS-PAGE protocols, transferred to nitrocellulose membranes and probed with an antibody that recognizes the invariant chain including the p10Ii fragment. In the presence of LHVS the p10Ii fragment was seen, representing a block in the degradation of Ii due to inhibition of cathepsin S.

Example 40
Monitoring in vivo Inhibition of Allergenic Response by Cathepsin S Inhibitors To demonstrate the efficacy of cathepsin S inhibitors for suppressing allergic responses in vivo, allergic volunteers are dosed with cathepsin S inhibitors to levels where invariant chain degradation is inhibited. Allergens are deposited subcutaneously, and the size of the cutaneous reactions are determined at 15 min, 6 h and 24 h. Skin biopsies are performed at 24 h. The immediate weal and flare response is not mediated by a T cell response and is not expected to be influenced by cathepsin S inhibitors, while the late phase induration (noticeable at 6 hours, more pronounced at 24 hours) is characterized by activation and infiltration of CD4 T cells (as well as of eosinophils) and should be inhibited by administration of inhibitors of cathepsin S. The skin biopsies are used to determine the cellular composition in the induration, and cathepsin S treated subjects are expected to have fewer activated CD4 T cells present than placebo-treated subjects.

References for these procedures are provided in Eberlein-Konig et al. (1999) Clin. Exp. Allergy 29:1641–1647 and in Gaga et al. (1991) J. Immunol. 147:816–822.

As controls for the experiment, prednisone and cyclosporine A will be used. Prednisone will inhibit both the immediate and the late phase responses, while cyclosporin A will inhibit only the late phase response.

F. OTHER EMBODIMENTS

The features and advantages of the invention are apparent to one of ordinary skill in the art. Based on this disclosure, including the summary, detailed description, background, examples, and claims, one of ordinary skill in the art will be able to make modifications and adaptations to various conditions and usages. These other embodiments are also within the scope of the invention.

What is claimed is:

1. A method for treating a subject with an allergic condition, said method comprising administering to the subject a therapeutically effective amount of a pharmaceutical composition comprising a compound of formula (I):

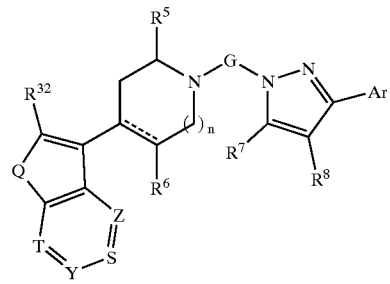

wherein:
the dashed line adjacent C—$R^6$ is absent or an $sp^2$ bond;
Y is nitrogen or $R^{20}C$;
Z is nitrogen or $R^{21}C$;
T is nitrogen or $R^2C$;
S is nitrogen or $R^3C$;
provided between 0 and 3 of S, T, Y, and Z are nitrogen; and further provided that one of S, T, Y, and Z can be =$N^+$—$O^-$ where the remaining three are not nitrogen;

$R^{20}$ is selected from hydrogen, halogen, $C_{1-5}$ alkoxy, hydroxy, $C_{1-5}$ alkyl, cyano, nitro, $C_{1-5}$ haloalkyl, $R^aR^bN$, $R^aR^bNC=O$, $C_{2-8}$ acyl, 4–7 membered heterocyclyl, (4–7 membered heterocyclyl)-$C_{1-5}$ alkylene, phenyl, (phenyl)$C_{1-5}$ alkylene, $R^{14}OC=O$, $R^{14}S$, $R^4SO$, and $R^{14}SO_2$;

$R^{21}$ is selected from hydrogen, halogen, $C_{1-5}$ alkoxy, hydroxy, $C_{1-5}$ alkyl, cyano, nitro, $C_{1-5}$ haloalkyl, $R^cR^dN$, $R^cR^dNC=O$, $C_{2-8}$ acyl, 4–7 membered heterocyclyl, (4–7 membered heterocyclyl)-$C_{1-5}$ alkylene, phenyl, (phenyl)$C_{1-5}$ alkylene, $R^{15}OC=O$, $R^{15}S$, $R^{15}SO$ and $R^{15}SO_2$;

$R^2$ is selected from hydrogen, halogen, $C_{1-5}$ alkoxy, hydroxy, $C_{1-5}$ alkyl, cyano, nitro, $C_{1-5}$ haloalkyl, $R^eR^fN$, $R^eR^fNC=O$, $C_{2-8}$ acyl, 4–7 membered heterocyclyl, (4–7 membered heterocyclyl)-$C_{1-5}$ alkylene, phenyl, (phenyl)$C_{1-5}$ alkylene, $R^{16}OC=O$, $R^{16}S$, $R^{16}SO$ and $R^{16}SO_2$;

$R^3$ is selected from hydrogen, halogen, $C_{1-5}$ alkoxy, hydroxy, $C_{1-5}$ alkyl, cyano, nitro, $C_{1-5}$ haloalkyl, $R^gR^hN$, $C_{2-8}$ acyl, 4–7 membered heterocyclyl, (4–7 membered heterocyclyl)-$C_{1-5}$ alkylene, phenyl, (phenyl)$C_{1-5}$ alkylene, $R^{17}OC=O$, $R'''R''NC=O$, $R'''R''NSO_2$, $R^{17}S$, $R^{17}SO$ and $R^{17}SO_2$;

$R^5$ and $R^6$ are independently selected from hydrogen and $C_{1-5}$ alkyl;

$R^7$ and $R^8$ independently are hydrogen, $C_{1-5}$ alkyl, $C_{1-5}$ alkenyl, $C_{1-5}$ alkoxy, $C_{1-5}$ alkylthio, halogen, or 4–7 membered carbocyclyl or heterocyclyl; alternatively, $R^7$ and $R^8$ can be taken together to form an optionally substituted 5- to 7-membered carbocyclic or heterocyclic ring, which ring may be unsaturated or aromatic; said ring being optionally substituted with between 1 and 3 substituents independently selected from halo, hydroxy, cyano, nitro, amino, $R'$, $R'O$—, $R'S$—, $R'O$ ($C_{1-5}$ alkylene)-, $R'O(C=O)$—, $R'(C=O)$—, $R'(C=S)$—, $R'(C=O)O$—, $R'O(C=O)(C=O)$—, $R'SO_2$, $NHR''(C=NH)$—, $NHR''SO_2$—, and $NHR''(C=O)$—;

$R'$ is $C_{1-6}$ alkyl, phenyl, benzyl, phenethyl, or $C_{2-5}$ heterocyclyl, ($C_{1-5}$ heterocyclyl)$C_{1-6}$ alkylene, $NH_2$, mono- or di($C_{1-6}$ alkyl)N—, or $R^{49}OR^{50}$—, wherein $R^{49}$ is H, $C_{1-5}$ alkyl, $C_{2-5}$ alkenyl, phenyl, benzyl, phenethyl, $C_{1-5}$ heterocyclyl, or ($C_{1-5}$ heterocyclyl)$C_{1-6}$ alkylene and $R^{50}$ is $C_{1-5}$ alkylene, phenylene, or divalent $C_{1-5}$ heterocyclyl; and $R^u$ can be H in addition to the values for $R^t$;

$R^c$ is hydrogen, $C_{1-5}$ alkyl, phenyl, $C_{2-5}$ heterocyclyl, $C_{2-8}$ acyl, aroyl, $R^{10}OC=O$—, $R^iR^jNC=O$, $R^{10}SO$—, $R^{10}SO_2$—, and $R^iR^jNSO_2$;

$R^e$ is hydrogen, $C_{1-5}$ alkyl, phenyl, $C_{2-5}$ heterocyclyl, $C_{2-8}$ acyl, aroyl, $R^{40}OC=O$, $R^{43}R^{44}NC=O$, $R^{40}SO$, $R^{40}SO_2$, and $R^{43}R^{44}NSO_2$;

$R^m$ is hydrogen, $C_{1-5}$ alkyl, phenyl, $C_{2-5}$ heterocyclyl, $C_{2-8}$ acyl, aroyl, $R^{41}OC=O$, $R^{45}R^{46}NC=O$, $R^{41}SO$, $R^{41}SO_2$, and $R^{45}R^{46}NSO_2$;

$R^o$ is hydrogen, $C_{1-5}$ alkyl, phenyl, $C_{2-5}$ heterocyclyl, $C_{2-8}$ acyl, aroyl, $R^{42}OC=O$, $R^{47}R^{48}NC=O$, $R^{42}SO$, $R^{42}SO_2$, and $R^{47}R^{48}NSO_2$;

each of $R^d$, $R^f$, $R^n$, and $R^p$ is independently selected from hydrogen, $C_{1-5}$ alkyl, phenyl, and $C_{2-5}$ heterocyclyl; in addition, $R^c$ and $R^d$, $R^e$ and $R^f$, $R^m$ and $R^n$, or $R^o$ and $R^p$, independently, can be taken together to form an optionally substituted 4- to 7-membered heterocyclic ring, which ring may be saturated, unsaturated or aromatic;

each of $R^9$, $R^{10}$, $R^{11}$, $R^{14}$, $R^{15}$, $R^{16}$, $R^{17}$, $R^{40}$, $R^{41}$, and $R^{42}$ is independently $C_{1-5}$ alkyl, phenyl, or $C_{2-5}$ heterocyclyl;

each of $R^i$ and $R^j$, $R^k$ and $R^l$, $R^{43}$ and $R^{44}$, $R^{45}$ and $R^{46}$, $R^{47}$ and $R^{48}$ are independently hydrogen, $C_{1-5}$ alkyl, $C_{3-5}$ alkenyl, phenyl, or $C_{2-5}$ heterocyclyl; in addition, $R^i$ and $R^j$, and $R^k$ and $R^l$, $R^{43}$ and $R^{44}$, $R^{45}$ and $R^{46}$, and $R^{47}$ and $R^{48}$, independently, can be taken together to form an optionally substituted 4- to 7-membered heterocyclic ring, which ring may be saturated, unsaturated or aromatic;

$R^9$ is hydrogen, $C_{1-5}$ alkyl, phenyl, or $C_{2-5}$ heterocyclyl, $C_{2-8}$ acyl, aroyl, $R^9OC=O$, $R^{18}R^{19}NC=O$, $R^9SO$, $R^9SO_2$, or $R^{18}R^{19}NSO_2$;

$R^h$ is hydrogen, $C_{1-5}$ alkyl, phenyl, or $C_{2-5}$ heterocyclyl; alternatively, $R^g$ and $R^h$ can be taken together to form an optionally substituted 4- to 7-membered heterocyclic ring, which ring may be saturated, unsaturated or aromatic;

$R^{18}$ and $R^{19}$ independently are hydrogen, $C_{1-5}$ alkyl, phenyl, or $C_{2-5}$ heterocyclyl; alternatively, $R^{18}$ and $R^{19}$ can be taken together to form an optionally substituted 4- to 7-membered heterocyclic ring, which ring may be saturated, unsaturated or aromatic;

n is 0, 1 or 2;

G is $C_{3-6}$ alkenediyl or $C_{3-6}$ alkanediyl, optionally substituted with hydroxy, halogen, $C_{1-5}$ alkyl, $C_{1-5}$ alkoxy, oxo, hydroximino, $CO_2R^k$, $NR^kR^l$, (L)—$C_{1-4}$ alkylene-, $R^kR^lNCO_2$, [(L)—$C_{1-5}$ alkylene]amino, $N_3$, or (L)—$C_{1-5}$ alkoxy;

L is amino, mono- or di-$C_{1-5}$ alkylamino, pyrrolidinyl, morpholinyl, piperidinyl, homopiperidinyl, or piperazinyl, wherein available ring nitrogens can be optionally substituted with $C_{1-5}$ alkyl, benzyl, $C_{2-5}$ acyl, $C_{1-5}$ alkylsulfonyl, or $C_{1-5}$ alkoxycarbonyl;

Ar represents a monocyclic or bicyclic aryl or heteroaryl ring, optionally substituted with between 1 and 3 substituents independently selected from halogen, $C_{1-5}$ alkoxy, $C_{1-5}$ alkyl, $C_{2-5}$ alkenyl, cyano, azido, nitro, $R^{22}R^{23}N$, $R^{22}S$, $R^{22}SO$, $R^{22}SO_2$, $R^{22}OC=O$, $R^{22}R^{23}NC=O$, $C_{1-5}$ haloalkyl, $C_{1-5}$ haloalkoxy, $C_{1-5}$ haloalkylthio, and $C_{1-5}$ alkylthio;

$R^{22}$ is hydrogen, $C_{1-5}$ alkyl, $C_{3-5}$ alkenyl, phenyl, benzyl, $C_{2-5}$ heterocyclyl, $C_{2-8}$ acyl, aroyl, $R^{11}OC=O$, $R^{24}R^{25}NC=O$, $R^{11}S$, $R^{11}SO$, $R^{11}SO_2$, or $R^{24}R^{25}NSO_2$;

$R^{23}$ is hydrogen, $C_{1-5}$ alkyl, phenyl, benzyl, or $C_{2-5}$ heterocyclyl; alternatively, $R^{22}$ and $R^{23}$ can be taken together to form an optionally substituted 4- to 7-membered heterocyclic ring, which ring may be saturated, unsaturated or aromatic;

$R^{24}$ and $R^{25}$ are independently hydrogen, $C_{1-5}$ alkyl, phenyl, benzyl, or $C_{1-5}$ heteroaryl; alternatively, $R^{24}$ and $R^{25}$ can be taken together to form an optionally substituted 4- to 7-membered carbocyclic or heterocyclic ring, which ring may be saturated, unsaturated or aromatic;

$R^{32}$ is hydrogen, $C_{1-5}$ alkyl, cyano, $C_{1-5}$ hydroxyalkyl, $C_{2-8}$ acyl, —(C=O)$NR^vR^x$, CHO, or $C_{1-6}$ alkoxycarbonyl, wherein each of $R^v$ and $R^x$ is independently selected from H, $C_{1-5}$ alkyl, $C_{1-5}$ hydroxyalkyl, $C_{1-5}$ heterocyclyl, ($C_{1-5}$ heterocyclyl) $C_{1-5}$ alkylene, $C_{1-5}$ aminoalkylene, $C_{3-8}$ acyloxy, CHO, $C_{1-6}$ alkoxycarbonyl, and cyano;

Q is $NR^{33}$, S, or O;

$R^{33}$ represents hydrogen, $C_{1-5}$ alkyl, phenyl, benzyl, phenethyl, $C_{2-5}$ heterocyclyl, ($C_{2-5}$ heterocyclyl)$C_{1-5}$ alkylene, $C_{2-8}$ acyl, aroyl, $R^{35}OC=O$, $R^{36}R^{37}NC=O$, $R^{35}SO$, $R^{35}S$, $R^{35}SO_2$ and $R^{36}R^{37}NSO_2$;

$R^{35}$ is selected from hydrogen, $C_{1-5}$ alkyl, phenyl, benzyl, phenethyl, and $C_{2-5}$ heteroaryl;

$R^{36}$ and $R^{37}$ are each independently selected from hydrogen, $C_{1-5}$ alkyl, phenyl, or $C_{2-5}$ heteroaryl; alternatively, $R^{36}$ and $R^{37}$ can be taken together to form an optionally substituted 4- to 7-membered ring heterocyclic ring, which ring may be saturated, unsaturated or aromatic;

wherein each of the above hydrocarbyl or heterocarbyl groups, unless otherwise indicated, and in addition to any specified substituents, is optionally and independently substituted with between 1 and 3 substituents selected from methyl, halomethyl, hydroxymethyl, halo, hydroxy, amino, nitro, cyano, $C_{1-5}$ alkyl, $C_{1-5}$ alkoxy, —COOH, $C_{2-6}$ acyl, [di($C_{1-4}$ alkyl)amino]$C_{2-5}$ alkylene, [di($C_{1-4}$ alkyl)amino] $C_{2-5}$ alkyl-NH—CO—, and $C_{1-5}$ haloalkoxy;

or a pharmaceutically acceptable salt, amide, or ester thereof; or a stereoisomeric form thereof.

2. A method of claim 1, wherein $R^{20}$ and $R^{21}$ are independently selected from hydrogen, halogen, $C_{1-5}$ alkoxy, $C_{1-5}$ alkyl, cyano, nitro, 4–7 membered heterocyclyl, and $R^oR^pN$ or $R^cR^dN$, respectively.

3. A method of claim 1, wherein

Y is nitrogen or $R^{20}C$;

Z is nitrogen or $R^{21}C$;

T is nitrogen or $R^2C$;

S is nitrogen or $R^3C$;

provided between 0 and 2 of S, T, Y, and Z are nitrogen;

$R^2$ is hydrogen, halogen, hydroxy, $C_{1-5}$ alkoxy, $C_{1-5}$ alkyl, 5- to 6-membered heterocyclyl, or $R^eR^fN$;

$R^3$ is hydrogen, halogen, $C_{1-5}$ alkoxy, hydroxy, $C_{1-5}$ alkyl, , 5- to 6-membered heterocyclyl, or $R^gR^hN$;

$R^5$ and $R^6$ are each H;

R[7] and R[8] independently are taken together to form an optionally substituted 5- to 7-membered unsaturated heterocyclic ring;

each of R[a], R[e], R[m], and R[o] is independently selected from hydrogen, $C_{1-5}$ alkyl, $C_{2-8}$ acyl, ($C_{1-5}$ alkyl)OC=O, and the respective RRNC=O, RSO, RSO$_2$, and RRNSO$_2$ groups;

each of R[b], R[f], R[n], and R[p], is independently selected from hydrogen and $C_{1-5}$ alkyl;

each of R[9], R[11], R[14], R[15], R[16], R[17], R[40], R[41] and R[42] is independently $C_{1-5}$ alkyl;

each of R[c], R[d], R[i], R[j], R[43], R[44], R[45], R[46], R[47], R[k] and R[l] are independently are hydrogen or $C_{1-5}$ alkyl;

R[g] is hydrogen, or $C_{1-5}$ alkyl, $C_{2-8}$ acyl, R[9]OC=O, R[18]R[19]NC=O, R[9]SO, R[9]SO$_2$, or R[18]R[19]NSO$_2$;

R[h] is hydrogen or $C_{1-5}$ alkyl; alternatively, R[g] and R[h] can be taken together to form an optionally substituted 4- to 7-membered carbocyclic or heterocyclic ring, which ring may be saturated, unsaturated or aromatic;

R[18] and R[19] independently are hydrogen or $C_{1-5}$ alkyl;

n is 0 or 1;

G is $C_{3-4}$ alkenediyl or $C_{3-4}$ alkanediyl, optionally substituted with hydroxy, halogen, $C_{1-5}$ alkyloxy, oxo, hydroximino, CO$_2$R[k], R[k]R[l]NCO$_2$, N$_3$, or (L)—$C_{1-5}$ alkoxy;

L is amino, mono- or di-$C_{1-5}$ alkylamino, pyrrolidinyl, morpholinyl, piperidinyl homopiperidinyl, or piperazinyl, available ring nitrogens being optionally with $C_{1-5}$ alkyl, benzyl, $C_{2-5}$ acyl, or $C_{1-5}$ alkyloxycarbonyl;

R[20] and R[21] are independently selected from hydrogen, halogen, $C_{1-5}$ alkoxy, $C_{1-5}$ alkyl, cyano, nitro, and R[o]R[p]N;

alternatively, R[3] and R[20] or R[3] and R[21] can be taken together to form an optionally substituted 5- or 6-membered carbocyclic or heterocyclic ring, which ring may be saturated, unsaturated or aromatic;

Ar represents a monocyclic or bicyclic aryl or heteroaryl ring, optionally substituted with hydrogen, halogen, $C_{1-5}$ alkoxy, $C_{1-5}$ alkyl, cyano, nitro, R[22]R[23]N, R[24]SO$_2$, R[24]OC=O, R[25]R[26]NC=O, CF$_3$, OCF$_3$, SCF$_3$, or $C_{1-5}$ alkylthio;

R[22] is hydrogen, $C_{1-5}$ alkyl, phenyl, benzyl, phenethyl, $C_{2-5}$ heteroaryl, $C_{2-8}$ acyl, aroyl, R[24]OC=O, R[25]R[26]NC=O, R[24]SO, R[24]SO$_2$, or R[25]R[2]NSO$_2$;

R[23] is hydrogen or $C_{1-5}$alkyl;

alternatively, R[22] and R[23] can be taken together to form an optionally substituted 4- to 7-membered carbocyclic or heterocyclic ring, which ring may be saturated, unsaturated or aromatic;

R[24] is hydrogen or $C_{1-5}$ alkyl;

R[25] and R[26] are independently hydrogen or $C_{1-5}$ alkyl;

or, alternatively, R[25] and R[26] can be taken together to form an optionally substituted 4- to 7-membered carbocyclic or heterocyclic ring, which ring may be saturated, unsaturated or aromatic;

R[32] is hydrogen, $C_{1-5}$ alkyl, $C_{1-5}$ hydroxyalkyl, CHO, $C_{2-6}$ acyl, $C_{1-6}$ alkoxycarbonyl, or —(C=O)NR[y]R[x], wherein each of R[y]R[x] is independently selected from H, $C_{1-5}$ alkyl, $C_{1-5}$ hydroxyalkyl, $C_{3-8}$ acyloxy, (amino) $C_{1-6}$ alkylene, ($C_{1-5}$ heterocyclyl)$C_{1-5}$ alkylene, or $C_{1-6}$ alkoxycarbonyl;

Q is NR[33] or S;

R[33] represents hydrogen, $C_{1-5}$ alkyl, phenyl, benzyl, ($C_{2-5}$ heterocyclyl)$C_{1-5}$ alkylene, $C_{2-8}$ acyl, aroyl, R[35]OC=O, R[36]R[37]NC=O, R[35]SO$_2$ and R[36]R[37]NSO$_2$;

R[35] is selected from hydrogen and $C_{1-5}$ alkyl;

R[36] and R[37] are each independently selected from hydrogen and $C_{1-5}$ alkyl.

4. A method of claim 1, wherein one of R[5] and R[6] is H,

R[7] and R[8] are taken together to form an optionally substituted 6-membered carbocyclic or heterocyclic ring; and Ar represents a monocyclic ring, optionally substituted with 1 to 2 substituents selected from halogen, $C_{1-5}$ alkyl, cyano, nitro, R[22]R[23]N, CF$_3$ and OCF$_3$.

5. A method of claim 4, wherein R[22] and R[23] taken together are independently morpholinyl, piperidyl, or pyrrolidinyl, optionally substituted.

6. A method of claim 1, wherein said compound is selected from:

1-[4-(5-Chloro-1H-indol-3-yl)-piperidin-1-yl]-3-[5-methanesulfonyl-3-(4-trifluoromethyl-phenyl)-4,5,6,7-tetrahydro-pyrazolo[4,3-c]pyridin-1-yl]-propan-2-ol;

1-[4-(7-Chloro-1H-indol-3-yl)-piperidin-1-yl]-3-[5-methanesulfonyl-3-(4-trifluoromethyl-phenyl)-4,5,6,7-tetrahydro-pyrazolo[4,3-c]pyridin-1-yl]-propan-2-ol;

1-[4-(5-Chloro-2-methyl-1H-indol-3-yl)-piperidin-1-yl]-3-[5-methanesulfonyl-3-(4-trifluoromethyl-phenyl)-4,5,6,7-tetrahydro-pyrazolo[4,3-c]pyridin-1-yl]-propan-2-ol;

1-{4-[6-Chloro-1-(2-morpholin-4-yl-ethyl)-1H-indol-3-yl]-piperidin-1-yl}-3-[5-methanesulfonyl-3-(4-trifluoromethyl-phenyl)-4,5,6,7-tetrahydro-pyrazolo[4,3-c]pyridin-1-yl]-propan-2-ol;

1-[5-Methanesulfonyl-3-(4-trifluoromethyl-phenyl)-4,5,6,7-tetrahydro-pyrazolo[4,3-c]pyridin-1-yl]-3-[4-(1H-pyrrolo[3,2-c]pyridin-3-yl)-piperidin-1-yl]-propan-2-ol;

1-[5-Methanesulfonyl-3-(4-trifluoromethyl-phenyl)-4,5,6,7-tetrahydro-pyrazolo[4,3-c]pyridin-1-yl]-3-[4-(1H-pyrrolo[2,3-b]pyridin-3-yl)-piperidin-1-yl]-propan-2-ol;

1-[5-Methanesulfonyl-3-(4-trifluoromethyl-phenyl)-4,5,6,7-tetrahydro-pyrazolo[4,3-c]pyridin-1-yl]-3-[4-(5-morpholin-4-yl-1H-pyrrolo[2,3-c]pyridin-3-yl)-piperidin-1-yl]-propan-2-ol;

1-[4-(6-Dimethylamino-1H-pyrrolo[3,2-c]pyridin-3-yl)-piperidin-1-yl]-3-[5-methanesulfonyl-3-(4-trifluoromethyl-phenyl)-4,5,6,7-tetrahydro-pyrazolo[4,3-c]pyridin-1-yl]-propan-2-ol;

1-[5-Methanesulfonyl-3-(4-trifluoromethyl-phenyl)-4,5,6,7-tetrahydro-pyrazolo[4,3-c]pyridin-1-yl]-3-[4-(6-morpholin-4-yl-1H-pyrrolo[3,2-c]pyridin-3-yl)-piperidin-1-yl]-propan-2-ol;

1-[5-Methanesulfonyl-3-(4-trifluoromethyl-phenyl)-4,5,6,7-tetrahydro-pyrazolo[4,3-c]pyridin-1-yl]-3-[4-(6-morpholin-4-yl-5-oxy-1H-pyrrolo[3,2-c]pyridin-3-yl)-piperidin-1-yl]-propan-2-ol;

6-Fluoro-3-(1-{3-[5-methanesulfonyl-3-(4-trifluoromethyl-phenyl)-4,5,6,7-tetrahydro-pyrazolo[4,3-c]pyridin-1-yl]-propyl}-piperidin-4-yl)benzo[b]thiophene-2-carboxylic acid (2-hydroxy-ethyl)-amide;

6-Fluoro-3-(1-{3-[5-methanesulfonyl-3-(4-trifluoromethyl-phenyl)-4,5,6,7-tetrahydro-pyrazolo[4,3-c]pyridin-1-yl]-propyl}-piperidin-4-yl)benzo[b]thiophene-2-carboxylic acid (2-amino-ethyl)-amide; and 6-Fluoro-3-(1-{3-[5-methanesulfonyl-3-(4-trifluoromethyl-phenyl)-4,5,6,7-tetrahydro-pyrazolo[4,3-c]pyridin-1-yl]-propyl}-piperidin-4-yl)benzo[b]thiophene-2-carboxylic acid (2-morpholin-4-yl-ethyl)-amide.

7. A method of claim 1, wherein said compound is selected from:

1-[1-{2-Hydroxy-3-[4-(1H-indol-3-yl)-piperidin-1-yl]-propyl}-3-(4-trifluoromethyl-phenyl)-1,4,6,7-tetrahydro-pyrazolo[4,3-c]pyridin-5-yl]-ethanone;

1-[4-(5-Fluoro-1H-indol-3-yl)-piperidin-1-yl]-3-[5-methanesulfonyl-3-(4-trifluoromethyl-phenyl)-4,5,6,7-tetrahydro-pyrazolo[4,3-c]pyridin-1-yl]-propan-2-ol;

1-[3-(4-Bromo-phenyl)-5-methanesulfonyl-4,5,6,7-tetrahydro-pyrazolo[4,3-c]pyridin-1-yl]-3-[4-(5-chloro-1H-indol-3-yl)-piperidin-1-yl]-propan-2-ol;

1-[3-(4-Bromo-phenyl)-5-methanesulfonyl-4,5,6,7-tetrahydro-pyrazolo[4,3-c]pyridin-1-yl]-3-[4-(5-chloro-2-methyl-1H-indol-3-yl)-piperidin-1-yl]-propan-2-ol;

1-[5-Methanesulfonyl-3-(4-trifluoromethyl-phenyl)-4,5,6,7-tetrahydro-pyrazolo[4,3-c]pyridin-1-yl]-3-[4-(5-methyl-1H-indol-3-yl)-piperidin-1-yl]-propan-2-ol;

3-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1H-indole-5-carbonitrile;

1-[5-Methanesulfonyl-3-(4-trifluoromethyl-phenyl)-4,5,6,7-tetrahydro-pyrazolo[4,3-c]pyridin-1-yl]-3-[4-(5-methoxy-1H-indol-3-yl)-piperidin-1-yl]-propan-2-ol;

3-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1H-indole-5-carboxylic acid ethyl ester;

1-[4-(6-Chloro-1H-indol-3-yl)-piperidin-1-yl]-3-[5-methanesulfonyl-3-(4-trifluoromethyl-phenyl)-4,5,6,7-tetrahydro-pyrazolo[4,3-c]pyridin-1-yl]-propan-2-ol;

1-[1-(3-{4-[6-Chloro-1-(2-morpholin-4-yl-ethyl)-1H-indol-3-yl]-piperidin-1-yl}-2-hydroxy-propyl)-3-(4-trifluoromethyl-phenyl)-1,4,6,7-tetrahydro-pyrazolo[4,3-c]pyridin-5-yl]-ethanone;

1-[5-Methanesulfonyl-3-(4-trifluoromethyl-phenyl)-4,5,6,7-tetrahydro-pyrazolo[4,3-c]pyridin-1-yl]-3-[4-(1H-pyrrolo[3,2-b]pyridin-3-yl)-piperidin-1-yl]-propan-2-ol;

1-[5-Methanesulfonyl-3-(4-trifluoromethyl-phenyl)-4,5,6,7-tetrahydro-pyrazolo[4,3-c]pyridin-1-yl]-3-[4-(1H-pyrrolo[2,3-c]pyridin-3-yl)-piperidin-1-yl]-propan-2-ol;

1-[5-Methanesulfonyl-3-(4-trifluoromethyl-phenyl)-4,5,6,7-tetrahydro-pyrazolo[4,3-c]pyridin-1-yl]-3-[4-(5-oxy-1H-pyrrolo[3,2-c]pyridin-3-yl)-piperidin-1-yl]-propan-2-ol;

1-[4-(5-Dimethylamino-1H-pyrrolo[3,2-b]pyridin-3-yl)-piperidin-1-yl]-3-[5-methanesulfonyl-3-(4-trifluoromethyl-phenyl)-4,5,6,7-tetrahydro-pyrazolo[4,3-c]pyridin-1-yl]-propan-2-ol;

1-[4-(5-Dimethylamino-1H-pyrrolo[2,3-c]pyridin-3-yl)-piperidin-1-yl]-3-[5-methanesulfonyl-3-(4-trifluoromethyl-phenyl)-4,5,6,7-tetrahydro-pyrazolo[4,3-c]pyridin-1-yl]-propan-2-ol;

3-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1H-pyrrolo[2,3-b]pyridine-6-carbonitrile;

1-[5-Methanesulfonyl-3-(4-trifluoromethyl-phenyl)-4,5,6,7-tetrahydro-pyrazolo[4,3-c]pyridin-1-yl]-3-{4-[1-(2-morpholin-4-yl-ethyl)-1H-pyrrolo[2,3-b]pyridin-3-yl]-piperidin-1-yl}-propan-2-ol;

1-[5-Methanesulfonyl-3-(4-trifluoromethyl-phenyl)-4,5,6,7-tetrahydro-pyrazolo[4,3-c]pyridin-1-yl]-3-[4-(7-morpholin-4-yl-1H-pyrrolo[2,3-c]pyridin-3-yl)-piperidin-1-yl]-propan-2-ol;

1-[4-(6-Fluoro-2-hydroxymethyl-benzo[b]thiophen-3-yl)-piperidin-1-yl]-3-[5-methanesulfonyl-3-(4-trifluoromethyl-phenyl)-4,5,6,7-tetrahydro-pyrazolo[4,3-c]pyridin-1-yl]-propan-2-ol;

6-Fluoro-3-(1-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-benzo[b]thiophene-2-carbaldehyde;

6-Fluoro-3-(1-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-benzo[b]thiophene-2-carboxylic acid methyl ester;

6-Fluoro-3-(1-{3-[5-methanesulfonyl-3-(4-trifluoromethyl-phenyl)-4,5,6,7-tetrahydro-pyrazolo[4,3-c]pyridin-1-yl]-propyl}-piperidin-4-yl)benzo[b]thiophene-2-carboxylic acid amide;

and 6-Fluoro-3-(1-{3-[5-methanesulfonyl-3-(4-trifluoromethyl-phenyl)-4,5,6,7-tetrahydro-pyrazolo[4,3-c]pyridin-1-yl]-propyl}-piperidin-4-yl)benzo[b]thiophene-2-carboxylic acid ethylamide.

8. A method of claim 1, wherein said compound is selected from:

1-{4-[6-Chloro-1-(2-morpholin-4-yl-ethyl)-1H-indol-3-yl]-piperidin-1-yl}-3-[5-methanesulfonyl-3-(4-trifluoromethyl-phenyl)-4,5,6,7-tetrahydro-pyrazolo[4,3-c]pyridin-1-yl]-propan-2-ol;

6-Fluoro-3-(1-{3-[5-methanesulfonyl-3-(4-trifluoromethyl-phenyl)-4,5,6,7-tetrahydro-pyrazolo[4,3-c]pyridin-1-yl]-propyl}-piperidin-4-yl)benzo[b]thiophene-2-carboxylic acid (2-morpholin-4-yl-ethyl)-amide;

1-[5-Methanesulfonyl-3-(4-trifluoromethyl-phenyl)-4,5,6,7-tetrahydro-pyrazolo[4,3-c]pyridin-1-yl]-3-[4-(5-oxy-1H-pyrrolo[3,2-c]pyridin-3-yl)-piperidin-1-yl]-propan-2-ol; and 1-[5-Methanesulfonyl-3-(4-trifluoromethyl-phenyl)-4,5,6,7-tetrahydro-pyrazolo[4,3-c]pyridin-1-yl]-3-[4-(6-morpholin-4-yl-1H-pyrrolo[3,2-c]pyridin-3-yl)-piperidin-1-yl]-propan-2-ol.

9. A method of claim 1, wherein said pharmaceutical composition is formulated in a dosage amount appropriate for the treatment of an allergic condition.

\* \* \* \* \*